(12) United States Patent
Himmelsbach et al.

(10) Patent No.: US 8,809,376 B2
(45) Date of Patent: Aug. 19, 2014

(54) INDANYLOXYDIHYDROBENZOFURANYL-ACETIC ACIDS

(71) Applicants: Frank Himmelsbach, Mittelbiberach (DE); Matthias Eckhardt, Biberach an der Riss (DE); Elke Langkopf, Biberach an der Riss (DE); Stefan Peters, Biberach an der Riss (DE)

(72) Inventors: Frank Himmelsbach, Mittelbiberach (DE); Matthias Eckhardt, Biberach an der Riss (DE); Elke Langkopf, Biberach an der Riss (DE); Stefan Peters, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/869,144

(22) Filed: Apr. 24, 2013

(65) Prior Publication Data

US 2013/0289074 A1 Oct. 31, 2013

(30) Foreign Application Priority Data

Apr. 30, 2012 (EP) .................................... 12166095

(51) Int. Cl.
*A61K 31/44* (2006.01)
*C07D 307/87* (2006.01)

(52) U.S. Cl.
USPC ......... 514/337; 514/469; 549/462; 546/284.1

(58) Field of Classification Search
USPC ................ 514/337, 469; 549/462; 546/284.1
See application file for complete search history.

(56) References Cited

U.S. PATENT DOCUMENTS

| 7,799,782 | B2 * | 9/2010 | Munson et al. ............ 514/234.5 |
| 2006/0258722 | A1 | 11/2006 | Yasuma et al. |
| 2012/0302566 | A1 | 11/2012 | Himmelsbach et al. |
| 2013/0196998 | A1 | 8/2013 | Stoit et al. |

FOREIGN PATENT DOCUMENTS

| EP | 1559422 A1 | 8/2005 |
| EP | 1630152 A1 | 3/2006 |
| EP | 2006271 A2 | 12/2008 |
| EP | 2289868 A1 | 3/2011 |
| WO | 2008001931 A2 | 1/2008 |
| WO | 2009157418 A1 | 12/2009 |
| WO | 2010045258 A2 | 4/2010 |
| WO | 2010143733 A1 | 12/2010 |
| WO | 2012072691 A1 | 6/2012 |

OTHER PUBLICATIONS

Mikami, et al., "Discovery of Phenylpropanoic Acid Derivatives Containing Polar Functionalities as Potent and Orally Bioavailable G Protein-Coupled Receptor 40 Agonists for the Treatment of Type 2 Diabetes", Journal of Medicinal Chemistry, 2012, V. 55, No. 8, p. 3756-3776.
International Search Report and written opinion for PCT/EP 2013/058840 mailed Aug. 22, 2013.
Mikami, Satoshi et al. "Discovery of Phenylpropanoic Acid Derivatives Containing Polar Functionalities as Potent and Orally Bioavailable G Protein-Coupled Receptor 40 Agonists for the Treatment of Type 2 Diabetes" Journal of Medicinal Chemistry (2012) 55, 3756-3776.
Negoro, Nobuyuki et al. "Identification of Fused-Ring Alkanoic Acids with Improved Pharmacokinetic Profiles that Act as G Protein-Coupled Receptor 40/ Free Fatty Acid Receptor 1 Agonists" Journal of Medicinal Chemistry, (2012) 55, pp. 1538-1552.
International Search Report for PCT/EP2013/056312 mailed on May 27, 2013.
Itoh, et al., Free fatty acids regulate insulin secretion from pancreatic b cells through GPR40, Letters to Nature, 2003, vol. 422, p. 173-176.
Briscoe, et al., "The Orphan G Protein-coupled Receptor GPR40 is activated by Medium and Long Chain Fatty Acids", Journal of Biological Chemistry, vol. 278, No. 13, 2003, p. 11303-11311.
Kotarsky, et al., "A human cell surface receptor activated by free fatty acids and thiazolidine drugs", Biochemical and Biophysical Research Communications, vol. 301, No. 2, 2003, p. 406-410.
Song et al., "Synthesis and Biological Evaluation of 3-Aryl-3-(4-phenoxy)-propionic Acid as a Novel Series of G Protein-Coupled Receptor 40 Agonists", Journal of Medicinal Chemistry, vol. 50, 2007, p. 2807-2817.
Tan, et al., "Selective Small-Molecule Agonists of G Protein-coupled Receptor 40 Promote Glucose-Dependent Insulin Secretion and Reduce Blood Glucose in Mice", Diabetes, vol. 57, 2008, p. 2211.

* cited by examiner

*Primary Examiner* — REi-tsang Shiao
(74) *Attorney, Agent, or Firm* — Michael P. Morris; Timothy X. Witkowski

(57) ABSTRACT

The present invention relates to compounds of general formula I,

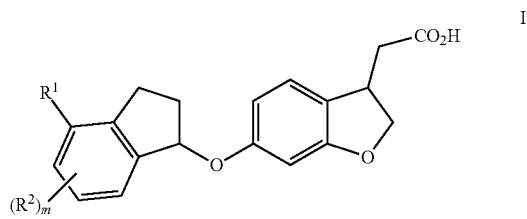

wherein the groups $R^1$, $R^2$ and m are defined as in claim 1, which have valuable pharmacological properties, in particular bind to the GPR40 receptor and modulate its activity. The compounds are suitable for treatment and prevention of diseases which can be influenced by this receptor, such as metabolic diseases, in particular diabetes type 2.

12 Claims, No Drawings

INDANYLOXYDIHYDROBENZOFURANYL-ACETIC ACIDS

This application claims priority to European Patent Application No. 12 166 095.5, filed Apr. 30, 2012, the contents of which are hereby incorporated by reference in its entirety.

FIELD OF THE INVENTION

The present invention relates to novel indanyloxydihydrobenzofuranylacetic acids, that are agonists of the G-protein coupled receptor 40 (GPR40, also known as free fatty acid receptor FFAR 1), to processes for their preparation, to pharmaceutical compositions containing these compounds and to their medical use for the prophylaxis and/or treatment of diseases which can be influenced by the modulation of the function of GPR40. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

The free fatty acid receptor GPR40 (also referred to as either FFAR, FFAR1, or FFA1) is a cell-surface receptor and a member of the gene superfamily of G-protein coupled receptors, which was first identified as a so-called orphan receptor, i.e. a receptor without a known ligand, based on the predicted presence of seven putative transmembrane regions in the corresponding protein (Sawzdargo et al. (1997) Biochem. Biophys. Res. Commun. 239: 543-547). GPR40 is found to be highly expressed in several particular cell types: the pancreatic β cells and insulin-secreting cell lines, as well as in enteroendocrine cells, taste cells, and is reported to be expressed in immune cells, splenocytes, and in the human and monkey brain. Meanwhile, fatty acids of varying chain lengths are thought to represent the endogenous ligands for GPR40, activation of which is linked primarily to the modulation of the Gq family of intra-cellular signaling G proteins and concomitant induction of elevated calcium levels, although activation of Gs- and Gi-proteins to modulate intra-cellular levels of cAMP have also been reported. GPR40 is activated especially by long-chain FFA, particularly oleate, as well as the PPAR-gamma agonist rosiglitazone.

It has been recognized that the fatty acids that serve as activators for GPR40 augment the elevated plasma glucose-induced secretion of insulin through GPR40 receptors that are expressed in the insulin secreting cells (Itoh et al. (2003) Nature 422: 173-176; Briscoe et al. (2003) J. Biol. Chem. 278: 11303-11311; Kotarsky et al. (2003) Biochem. Biophys. Res. Commun. 301: 406-410). Despite initial controversy, the use of GPR40 agonist appears to be the appropriate for increasing insulin release for the treatment of diabetes (see e.g. Diabetes 2008, 57, 2211; J. Med. Chem. 2007, 50, 2807). Typically, long term diabetes therapy leads to the gradual diminution of islet activity, so that after extended periods of treatment Type 2 diabetic patients need treatment with daily insulin injections instead. GPR40 agonists may have the potential to restore or preserve islet function, therefore, GPR40 agonists may be beneficial also in that that they may delay or prevent the diminution and loss of islet function in a Type 2 diabetic patient.

It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Further studies indicating that the GPR40 modulatory role on the release of incretins from the enteroendocrine cells, including CCK, GLP-1, GIP, PYY, and possibly others, suggest that GPR40 modulators may contribute to enhanced insulin release from the pancreatic beta cells also indirectly by e.g. a synergistic effect of GLP-1 and possibly GIP on the insulin release, and the other release incretins may also contribute to an overall beneficial contribution of GPR40 modulation on metabolic diseases. The indirect contributions of GPR40 modulation on insulin release through the elevation of plasma levels of incretins may be further augmented by the coadministration of inhibitors of the enzymes responsible for the incretin degradation, such as inhibitors of DPP-4.

Insulin imbalances lead to conditions such as type II diabetes mellitus, a serious metabolic disease. The modulation of the function of GPR40 in modulating insulin secretion indicates the therapeutic agents capable of modulating GPR40 function could be useful for the treatment of disorders such as diabetes and conditions associated with the disease, including insulin resistance, obesity, cardiovascular disease and dyslipidemia.

OBJECT OF THE PRESENT INVENTION

The object of the present invention is to provide new compounds, hereinafter described as compounds of formula I, in particular new indanyloxydihydrobenzofuranylacetic acids, which are active with regard to the G-protein-coupled receptor GPR40, notably are agonists of the G-protein-coupled receptor GPR40.

A further object of the present invention is to provide new compounds, in particular new indanyloxydihydrobenzofuranylacetic acids, which have an activating effect on the G-protein-coupled receptor GPR40 in vitro and/or in vivo and possess suitable pharmacological and pharmacokinetic properties to use them as medicaments.

A further object of the present invention is to provide effective GPR40 agonists, in particular for the treatment of metabolic disorders, for example diabetes, dyslipidemia and/or obesity.

A further object of the present invention is to provide methods for treating a disease or condition mediated by the activation the G-protein-coupled receptor GPR40 in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

GPR40 modulators are known in the art, for example, the compounds disclosed in WO 2004041266 (EP 1559422), WO 2007033002 and WO 2009157418. The indanyloxydihydrobenzofuranylacetic acids of the present invention may provide several advantages, such as enhanced potency, high metabolic and/or chemical stability, high selectivity and tolerability, enhanced solubility, and the possibility to form stable salts.

SUMMARY OF THE INVENTION

In a first aspect the invention relates to a compound of formula I

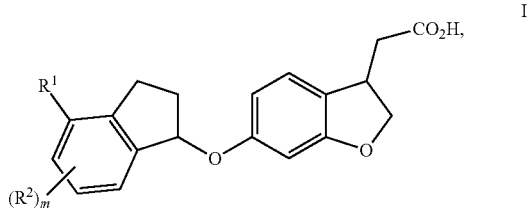

wherein
$R^1$ is selected from the group $R^1$-G1 consisting of phenyl-$CH_2$— and heteroaryl-$CH_2$—,
  wherein phenyl and heteroaryl are optionally substituted with 1 to 5 $R^3$ groups, and both —$CH_2$— moieties are optionally substituted with 1 or 2 $H_3C$— groups,
  wherein heteroaryl is a 5-membered heteroaromatic ring which contains 1 —NH-group, 1-O—, or —S— atom, or
    a 5-membered heteroaromatic ring which contains 1 —NH— group, 1-O— or —S-atom and additionally 1 or 2 =N— atoms, or
    a 6-membered heteroaromatic ring which contains 1, 2 or 3 =N— atoms;
$R^2$ is selected from the group $R^2$-G1 consisting of F, Cl, Br, NC—, $F_2HC$—, $F_3C$—, $F_2HC$—O—, and $F_3C$—O—;
$R^3$ is selected from the group $R^3$-G1 consisting of F, Cl, Br, I, NC—, $C_2N$—, $H_2N$—, $C_{1-4}$-alkyl-NH—, $(C_{1-4}$-alkyl$)_2$N—, $C_{1-4}$-alkyl, $C_{2-4}$-alkenyl, $C_{2-4}$-alkinyl, HO—, HO—$C_{1-4}$-alkyl, $C_{1-4}$-alkyl-O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl-, and $C_{3-6}$-cycloalkyl-O—,
  wherein any alkyl and cycloalkyl group or submoiety is optionally substituted with 1 to 5 fluorine atoms, preferably with 1 to 3 fluorine atoms; and
m is an integer selected from 1 and 2;
wherein in any definition mentioned hereinbefore and if not specified otherwise, any alkyl group or sub-group may be straight-chained or branched,
the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, $R^1$-G1 defines genus 1 of the substituent $R^1$.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR40 in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR40 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the G-protein-coupled receptor GPR40.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$, $R^3$, and m are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

According to one embodiment the group $R^1$ is selected from the group $R^1$-G2 consisting of phenyl-$CH_2$— and heteroaryl-$CH_2$, wherein the phenyl ring is optionally substituted with 1 to 5 groups independently selected from $R^3$, the heteroaryl ring is optionally substituted with 1 to 3 groups independently selected from $R^3$, and both —$CH_2$— moieties are optionally substituted with 1 or 2 $H_3C$— groups, and wherein heteroaryl is a 5-membered heteroaromatic ring which contains 1 —NH-group, 1 —O— or —S— atom and additionally 1 or 2 =N— atoms, or a 6-membered heteroaromatic ring which contains 1 or 2 =N— atoms.

$R^1$-G3:

According to one embodiment the group $R^1$ is selected from the group $R^1$-G3 consisting of

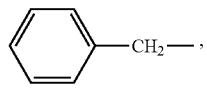 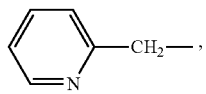

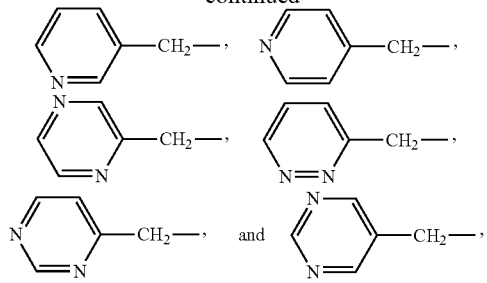

wherein the phenyl group and each heteroaromatic group is optionally substituted with 1 to 3 groups independently selected from $R^3$, and each —$CH_2$— moiety is optionally substituted with 1 or 2 $H_3C$— groups.

$R^1$-G4:

In another embodiment the group $R^1$ is selected from the group $R^1$-G4 consisting of

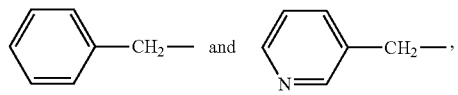

wherein the phenyl and pyridyl group are optionally substituted with 1 to 3 groups independently selected from $R^3$, and both —$CH_2$— moieties are optionally substituted with 1 or 2 $H_3C$— groups.

$R^1$-G4a:

In another embodiment the group $R^1$ is selected from the group $R^1$-G4a consisting of

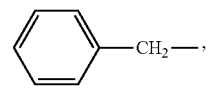

wherein the phenyl group is optionally substituted with 1 to 3 groups independently selected from $R^3$, and the —$CH_2$— moiety is optionally substituted with 1 or 2 $H_3C$-groups.

$R^1$-G4b:

In another embodiment the group $R^1$ is selected from the group $R^1$-G4b consisting of

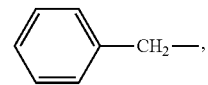

wherein the phenyl group is optionally substituted with 1 to 3 groups independently selected from $R^3$.

$R^1$-G5:

In another embodiment the group $R^1$ is selected from the group $R^1$-G5 consisting of

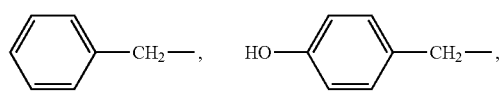

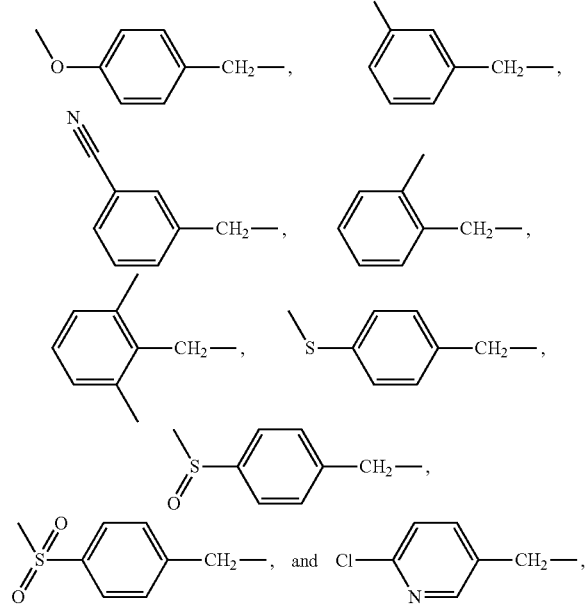

R¹-G5a:

In another embodiment the group R¹ is selected from the group R¹-G5a consisting of

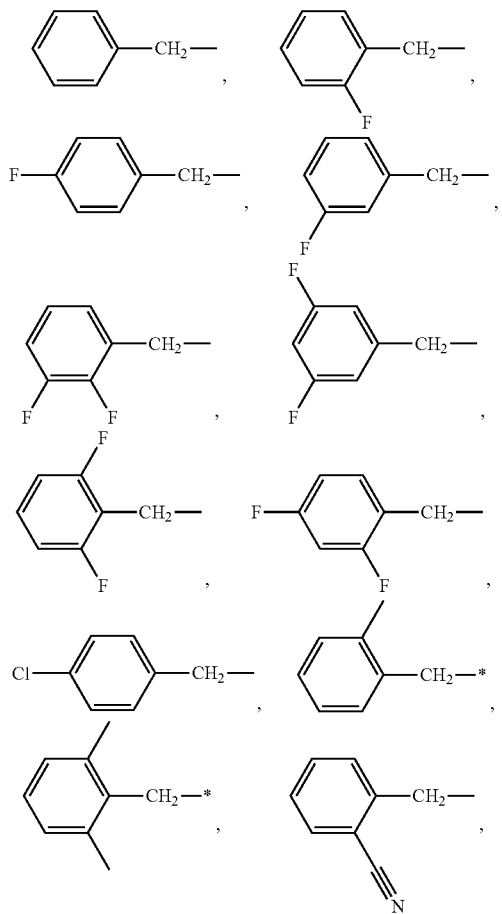

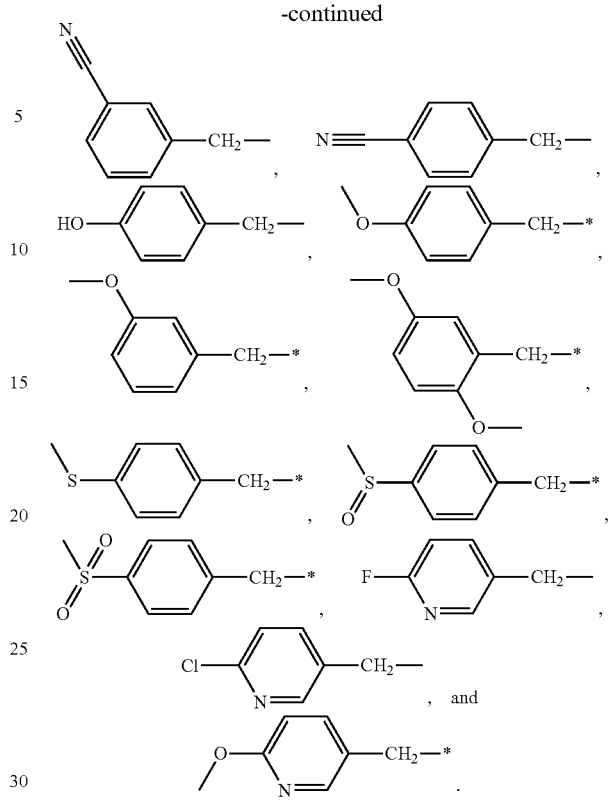

R²:
R²-G1:
The group R² is preferably selected from the group R²-G1 as defined hereinbefore.
R²-G2:
In another embodiment the group R² is selected from the group R²-G2 consisting of F, Cl, F₃C—, NC—, and F₃C—O—.
R²-G3:
In another embodiment the group R² is selected from the group R²-G3 consisting of F, F₃C—, and NC—.
R³:
R³-G1:
The group R³ is preferably selected from the group R³-G1 as defined hereinbefore.
R³-G2:
In another embodiment the group R³ is selected from the group R³-G2 consisting of F, Cl, Br, NC—, $C_{1-4}$-alkyl-NH—, $(C_{1-4}$-alkyl$)_2$N—, $C_{1-4}$-alkyl, F₂HC—, F₃C—, HO—, HO—$C_{1-4}$-alkyl, $C_{1-4}$-alkyl-O—, F₂HC—O—, F₃C—O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl-, and $C_{3-6}$-cycloalkyl-O—.
R³-G3:
In another embodiment the group R³ is selected from the group R³-G3 consisting of F, Cl, NC—, $C_{1-4}$-alkyl, F₂HC—, F₃C—, HO—, HO—$C_{1-4}$-alkyl, $C_{1-4}$-alkyl-O—, F₂HC—O—, F₃C—O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl-, and $C_{4-6}$-cycloalkyl-O—.
R³-G4:
In another embodiment the group R³ is selected from the group R³-G4 consisting of F, Cl, NC—, H₃C—, F₂HC—, F₃C—, HO—, HO—CH₂—, H₃C—O—, F₂HC—O—, $F_3C-O-$, $H_3C-O-CH_2-$, $H_3C-S-$, $H_3C-S(=O)-$, and $H_3C-S(=O)_2-$.

$R^3$-G5:

In another embodiment the group $R^3$ is selected from the group $R^3$-G5 consisting of $C_1$, $H_3C-$, $NC-$, $HO-$, $H_3C-O-$, $H_3C-S-$, $H_3C-S(=O)-$, and $H_3C-S(=O)_2-$.

$R^3$-G5a:

In another embodiment the group $R^3$ is selected from the group $R^3$-G5 consisting of F, Cl, $H_3C-$, $NC-$, $HO-$, $H_3C-O-$, $H_3C-S-$, $H_3C-S(=O)-$, and $H_3C-S(=O)_2-$.

m denotes 1 or 2, preferably 1.

The following preferred embodiments of compounds of the formula I are described using generic formulae I.1 to I.3, wherein any tautomers, solvates, hydrates and salts thereof, in particular the pharmaceutically acceptable salts thereof, are encompassed.

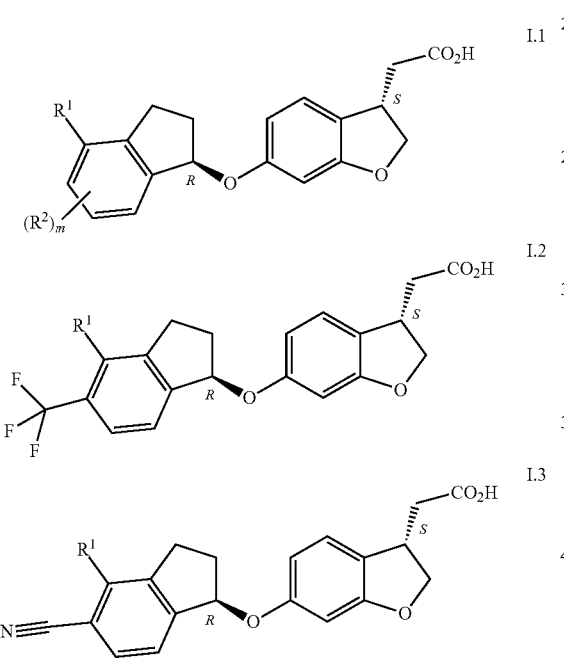

Examples of preferred subgeneric embodiments (E) according to the present invention are set forth in the following table, wherein each substituent group of each embodiment is defined according to the definitions set forth hereinbefore and wherein all other substituents of the formulas I and I.1 are defined according to the definitions set forth hereinbefore:

| E | R¹- | R²- | R³- | m |
|---|---|---|---|---|
| E-1 | R¹-G1 | R²-G1 | R³-G1 | 1, 2 |
| E-2 | R¹-G1 | R²-G1 | R³-G2 | 1, 2 |
| E-3 | R¹-G1 | R²-G1 | R³-G3 | 1, 2 |
| E-4 | R¹-G2 | R²-G1 | R³-G1 | 1, 2 |
| E-5 | R¹-G2 | R²-G1 | R³-G2 | 1, 2 |
| E-6 | R¹-G2 | R²-G1 | R³-G3 | 1, 2 |
| E-7 | R¹-G3 | R²-G1 | R³-G1 | 1, 2 |
| E-8 | R¹-G3 | R²-G1 | R³-G2 | 1, 2 |
| E-9 | R¹-G3 | R²-G1 | R³-G3 | 1, 2 |
| E-10 | R¹-G4a | R²-G1 | R³-G1 | 1, 2 |
| E-11 | R¹-G4a | R²-G1 | R³-G2 | 1, 2 |
| E-12 | R¹-G4a | R²-G1 | R³-G3 | 1, 2 |
| E-13 | R¹-G4a | R²-G1 | R³-G4 | 1, 2 |
| E-14 | R¹-G2 | R²-G2 | R³-G1 | 1, 2 |
| E-15 | R¹-G2 | R²-G2 | R³-G2 | 1, 2 |
| E-16 | R¹-G2 | R²-G2 | R³-G3 | 1, 2 |
| E-17 | R¹-G2 | R²-G2 | R³-G4 | 1, 2 |
| E-18 | R¹-G2 | R²-G2 | R³-G5 | 1, 2 |
| E-19 | R¹-G2 | R²-G3 | R³-G1 | 1, 2 |
| E-20 | R¹-G2 | R²-G3 | R³-G2 | 1, 2 |
| E-21 | R¹-G2 | R²-G3 | R³-G3 | 1, 2 |
| E-22 | R¹-G2 | R²-G3 | R³-G4 | 1, 2 |
| E-23 | R¹-G2 | R²-G3 | R³-G5 | 1, 2 |
| E-24 | R¹-G3 | R²-G2 | R³-G1 | 1, 2 |
| E-25 | R¹-G3 | R²-G2 | R³-G2 | 1, 2 |
| E-26 | R¹-G3 | R²-G2 | R³-G3 | 1, 2 |
| E-27 | R¹-G3 | R²-G2 | R³-G4 | 1, 2 |
| E-28 | R¹-G3 | R²-G2 | R³-G5 | 1, 2 |
| E-29 | R¹-G4a | R²-G2 | R³-G1 | 1, 2 |
| E-30 | R¹-G4a | R²-G2 | R³-G2 | 1, 2 |
| E-31 | R¹-G4a | R²-G2 | R³-G3 | 1, 2 |
| E-32 | R¹-G4a | R²-G2 | R³-G4 | 1, 2 |
| E-33 | R¹-G4a | R²-G2 | R³-G5 | 1, 2 |
| E-34 | R¹-G3 | R²-G3 | R³-G1 | 1, 2 |
| E-35 | R¹-G3 | R²-G3 | R³-G2 | 1, 2 |
| E-36 | R¹-G3 | R²-G3 | R³-G3 | 1, 2 |
| E-37 | R¹-G3 | R²-G3 | R³-G4 | 1, 2 |
| E-38 | R¹-G3 | R²-G3 | R³-G5 | 1, 2 |
| E-39 | R¹-G4a | R²-G3 | R³-G1 | 1, 2 |
| E-40 | R¹-G4a | R²-G3 | R³-G2 | 1, 2 |
| E-41 | R¹-G4a | R²-G3 | R³-G3 | 1, 2 |
| E-42 | R¹-G4a | R²-G3 | R³-G4 | 1, 2 |
| E-43 | R¹-G4a | R²-G3 | R³-G5 | 1, 2 |
| E-44 | R¹-G4b | R²-G3 | R³-G1 | 1, 2 |
| E-45 | R¹-G4b | R²-G3 | R³-G2 | 1, 2 |
| E-46 | R¹-G4b | R²-G3 | R³-G3 | 1, 2 |
| E-47 | R¹-G4b | R²-G3 | R³-G4 | 1, 2 |
| E-48 | R¹-G4b | R²-G3 | R³-G5 | 1, 2 |
| E-49 | R¹-G5 | R²-G1 | — | 1, 2 |
| E-50 | R¹-G5 | R²-G2 | — | 1, 2 |
| E-51 | R¹-G5a | R²-G3 | — | 1 |

Preferred are those compounds of formula I and I.1, wherein $R^1$ is selected from the group consisting of

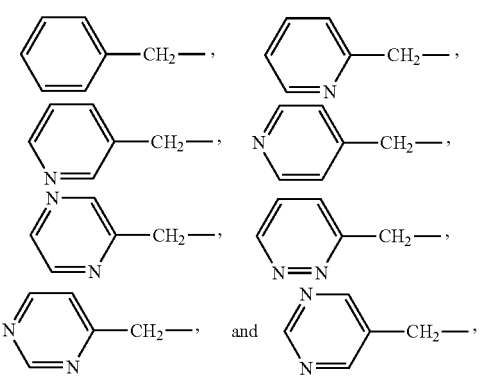

wherein the phenyl group and each heteroaromatic group is optionally substituted with 1 to 3 groups independently selected from $R^3$, and each $-CH_2-$ moiety is optionally substituted with 1 or 2 $H_3C-$ groups;

$R^2$ is selected from the group consisting of F, Cl, $F_3C-$, $NC-$, and $F_3C-O-$;

$R^3$ is selected from the group consisting of F, Cl, $NC-$, $C_{1-4}$-alkyl, $F_2HC-$, $F_3C-$, $HO-$, $HO-C_{1-4}$-alkyl, $C_{1-4}$-alkyl-O—, $F_2HC-O-$, $F_3C-O-$, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)_2—, $C_{3-6}$-cycloalkyl-, and $C_{4-6}$-cycloalkyl-O—; and m is 1 or 2, preferably 1; and the pharmaceutically acceptable salts thereof.

More preferred are those compounds of formula I and I.1, wherein
$R^1$ is

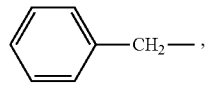

wherein the phenyl group is optionally substituted with 1 to 3 groups independently selected from $R^3$, and the —$CH_2$— moiety is optionally substituted with 1 or 2 $H_3C$— groups;
$R^2$ is selected from the group consisting of F, $F_3C$—, and NC—;
$R^3$ is selected from the group consisting of F, Cl, NC—, $C_{1-4}$-alkyl, $F_2HC$—, $F_3C$—, HO—, HO—$C_{1-4}$-alkyl, $C_{1-4}$-alkyl-O—, $F_2HC$—O—, $F_3C$—O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl-, and $C_{4-6}$-cycloalkyl-O—; and
m is 1 or 2, preferably 1; and the pharmaceutically acceptable salts thereof.

Particularly preferred are those compounds of formula I and I.1, wherein
$R^1$ is

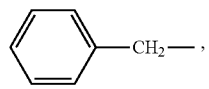

wherein the phenyl group is optionally substituted with 1 to 3 groups independently selected from $R^3$;
$R^2$ is selected from the group consisting of F, $F_3C$—, and NC—;
$R^3$ is selected from the group consisting of F, Cl, NC—, $C_{1-4}$-alkyl, $F_2HC$—, $F_3C$—, HO—, HO—$C_{1-4}$-alkyl, $C_{1-4}$-alkyl-O—, $F_2HC$—O—, $F_3C$—O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl-, and $C_{4-6}$-cycloalkyl-O—; and
m is 1 or 2, preferably 1; and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I are preferably accessed from a precursor 1 that bears the carboxylic acid function in a protected or masked form as sketched in Scheme 1; $R^1$, $R^2$, and m have the meanings as defined hereinbefore and hereinafter. Suited precursor groups for the carboxylic acid may be, e.g., a carboxylic ester, a carboxylic amide, cyano, an olefin, oxazole, or a thiazole. All these groups have been transformed into the carboxylic acid function by different means which are described in the organic chemistry literature and are known to the one skilled in the art. The preferred precursor group is a $C_{1-4}$-alkyl or benzyl carboxylate, each of which may be additionally mono- or polysubstituted with fluorine, methyl, and/or methoxy. These ester groups may be hydrolysed with an acid, such as hydrochloric acid or sulfuric acid, or more preferably an alkali metal hydroxide, such as lithium hydroxide, sodium hydroxide, or potassium hydroxide, to yield the carboxylic acid function; the hydrolysis is preferably conducted in aqueous solvents, such as water and tetrahydrofuran, 1,4-dioxane, alcohol, e.g. methanol, ethanol, and isopropanol, or dimethyl sulfoxide, at 0 to 120° C. A tert-butyl ester is preferably cleaved under acidic conditions, e.g. trifluoroacetic acid or hydrochloric acid, in a solvent such as dichloromethane, 1,4-dioxane, isopropanol, or ethyl acetate. A benzyl ester is advantageously cleaved using hydrogen in the presence of a transition metal, preferably palladium on carbon. Benzyl esters bearing electron donating groups, such as methoxy groups, on the aromatic ring may also be removed under oxidative conditions; ceric ammonium nitrate (CAN) or 2,3-dichloro-5,6-dicyanoquinone (DDQ) are two commonly used reagents for this approach.

Scheme 1

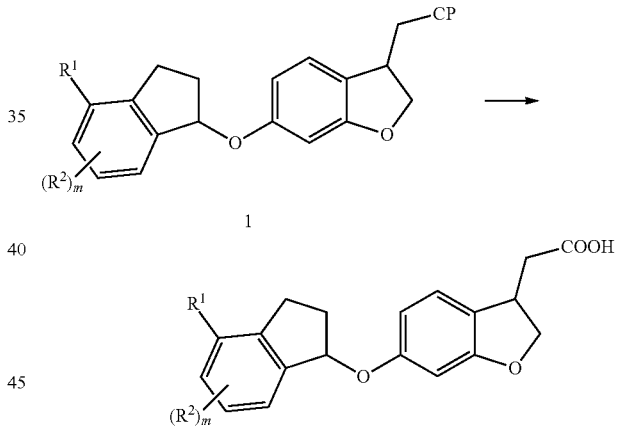

CP = masked or protected form of COOH, e.g., $CO_2C_{1-4}$-alkyl, $CO_2CH_2$aryl, $CON(C_{1-4}$-alkyl)$_2$, CN, CH=$CH_2$, thiazol-2-yl, oxazol-2-yl Compound 1, in turn, may be obtained from indane 2, which bears a leaving group, and phenol 3, which is decorated with the carboxylic acid precursor group (Scheme 2); $R^1$, $R^2$, and m in Scheme 2 have the meanings as defined hereinbefore and hereinafter. The leaving group LG in 2 is replaced with the O in 3 via a nucleophilic substitution; suited LG may be Cl, Br, I, methylsulfonyloxy, phenylsulfonyloxy, p-tolylsulfonyloxy, and trifluoromethylsulfonyloxy. The reaction is usually carried out in the presence of a base, such as triethylamine, ethyldiisopropylamine, 1,8-diazabicyclo[5.4.0]undecene, carbonates, e.g. $Li_2CO_3$, $Na_2CO_3$, $K_2CO_3$, and $Cs_2CO_3$, hydroxides, e.g. LiOH, NaOH, and KOH, alcoholates, e.g. NaOMe, NaOEt, and KOtBu, hydrides, e.g. NaH and KH, amides, e.g. $NaNH_2$, $KN(SiMe_3)_2$, and $LiN(iPr)_2$, and oxides, e.g. CaO and $Ag_2O$. Additives, such as silver salts, e.g. $AgNO_3$, $AgOSO_2CF_3$, and $Ag_2CO_3$, crown ethers, e.g.

12-crown-4, 15-crown-5, and 18-crown-6, hexamethylphosphorus triamide (HMPT), and 1,3-dimethyl-3,4,5,6-dihydro-2-pyrimidinone (DMPU), may be beneficial or even essential for the reaction to proceed. Preferred solvents are dimethylsulfoxide, N,N-dimethylformamide, N,N-dimethylacetamide, N-methylpyrrolidinone, acetonitrile, acetone, 1,4-dioxane, tetrahydrofuran, alcohol, e.g. ethanol or isopropanol, water, or mixtures thereof, while not all of the solvents can be combined with each additive and base mentioned above. Suited reaction temperatures range from −20 to 140° C.

Scheme 2

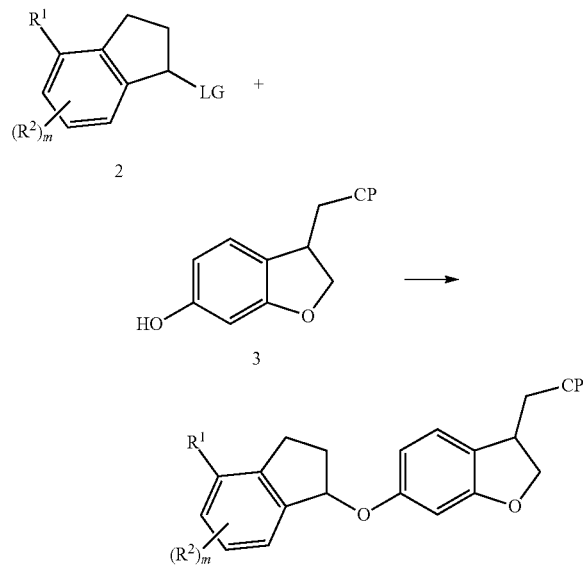

LG = leaving group, e.g., Cl, Br, I, OSO₂Me, OSO₂Ph, OSO₂Tol, OSO₂CF₃
CP = masked or protected form of COOH, e.g., CO₂C₁₋₄-alkyl, CO₂CH₂aryl, CON(C₁₋₄-alkyl)₂, CN, CH═CH₂, thiazol-2-yl, oxazol-2-yl An alternative reaction to combine building blocks 2 and 3 is the Mitsunobu reaction or variations thereof (Scheme 3); R¹, R², and m in Scheme 3 have the meanings as defined hereinbefore and hereinafter. The reaction is usually conducted with a phosphine and an azodicarboxylic ester or amide in tetrahydrofuran, 1,4-dioxane, diethyl ether, toluene, benzene, dichloromethane, or mixtures thereof, at −30 to 100° C. Phosphines often used are triphenylphosphine and tributylphosphine which are commonly combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide.

Scheme 3

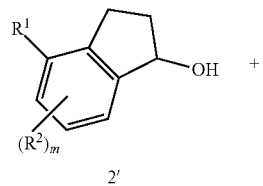

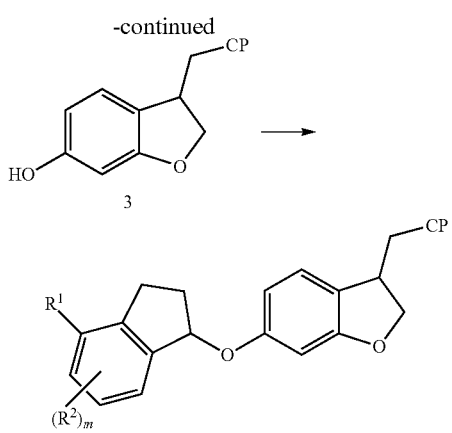

CP = masked or protected form of COOH, e.g., CO₂C₁₋₄-alkyl, CO₂CH₂aryl, CON(C₁₋₄-alkyl)₂, CN, CH═CH₂, thiazol-2-yl, oxazol-2-yl Intermediate 2' is conveniently obtained from indanone 4 which, in turn, may be prepared from phenylpropionic acid derivative 5 (Scheme 4); R¹, R², and m in Scheme 4 have the meanings as defined hereinbefore and hereinafter. For the intramolecular acylation (Friedel-Crafts acylation), 5→4, a considerable number of approaches has been reported. The reaction may be performed starting with a carboxylic acid, carboxylic ester, carboxylic anhydride, carboxylic chloride or a nitrile using a Lewis acid as catalyst. The following Lewis acids are some of the more often used ones: hydrobromic acid, hydroiodic acid, hydrochloric acid, sulfuric acid, phosphoric acid, P₄O₁₀, trifluoroacetic acid, methanesulfonic acid, toluenesulfonic acid, trifluoromethanesulfonic acid, ClSO₃H, Sc(OSO₂CF₃)₃, Tb(OSO₂CF₃)₃, SnCl₄, FeCl₃, AlBr₃, AlCl₃, SbCl₅, BCl₃, BF₃, ZnCl₂, montmorillonites, POCl₃, and PCl₅. The reaction may be conducted, e.g., in dichloromethane, 1,2-dichloroethane, nitrobenzene, chlorobenzene, carbon disulfide, mixtures thereof, or without an additional solvent in an excess of the Lewis acid, at 0 to 180° C. Carboxylic acids are preferably reacted in polyphosphoric acid at 0 to 120° C., while carboxylic chlorides are preferably reacted with AlCl₃ in dichloromethane or 1,2-dichloroethane at 0 to 80° C.

The subsequent reduction of the keto group in Scheme 4 is a standard transformation in organic synthesis, which may be accomplished with lithium borohydride, sodium borohydride, lithium aluminum hydride, or diisobutylaluminum hydride. While sodium borohydride is employed in aqueous or alcoholic solution at 0 to 60° C., the other reducing agents mentioned are preferably used in inert solvents, such as tetrahydrofuran, diethyl ether, dichloromethane, and toluene, at −80 to 60° C. The reduction of the keto group may also be conducted in a stereoselective fashion providing the alcohol in enantiomerically enriched or pure form. Suited chiral reducing agents are boranes combined with an enantiomerically pure [1,3,2]oxazaborol (Corey-Bakshi-Shibata reaction or Corey-Itsuno reaction) or formic acid, formates, hydrogen, or silanes in the presence of an enantiomerically pure transition metal catalyst. Typical reaction conditions for the former approach are borane (complexed with, e.g., dimethyl sulfide) and (R)- or (S)-3,3-diphenyl-1-methyltetrahydro-1H,3H-pyrrolo[1,2-c][1,3,2]oxazaborol in, e.g., dichloromethane, toluene, methanol, tetrahydrofuran, or mixtures thereof, at 0 to 60° C. Using a chiral transition metal catalyst, such as a ruthenium complex, e.g. chloro{[(1S,2S)-(−)-2-amino-1,2-diphenylethyl](4-toluenesulfonyl)-amido}-(mesitylene)ruthenium(II), may deliver the hydroxy compound with high enantiomeric excess using, e.g., formic acid in the presence of a base, e.g. triethylamine, in dichloromethane, at −20 to 60° C.

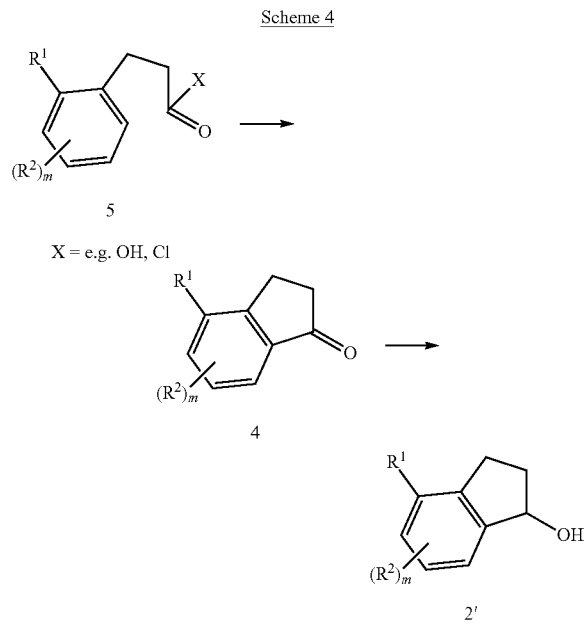

Scheme 4

X = e.g. OH, Cl

Alternatively, indanone 4 can be synthesized as described in Scheme 5; $R^1$, $R^2$, and m have the meanings as defined hereinbefore and hereinafter. Starting with benzene 6 and 3-halo-propionic acid or a derivative thereof or acrylic acid or a derivative thereof the required indanone 4 may be obtained via the combination of a Friedel-Crafts alkylation and acylation reaction in one pot or two separate reactions (eq. 1.)). These reactions are catalyzed by a Lewis acid, such as triflic acid, sulfuric acid, phosphoric acid, $AlCl_3$, $ZnCl_2$, and phosphorus pentoxide, and preferably conducted without additional solvent in an excess of the Lewis acid or in dichloromethane, 1,2-dichloroethane, cyclohexane, or carbon disulfide, at 0 to 140° C. A preferred combination comprises compound 6,3-chloro-propionyl chloride, and $AlCl_3$ in dichloromethane or 1,2-dichlorethane at 20 to 80° C.

Starting with ethynylbenzene 7 indanone 4 is accessible by a transition metal catalyzed reaction with carbon monoxide (eq. 2.)). Rhodium is a preferred catalyst basis which is combined with a phosphine, e.g. triphenylphosphine, and a base, e.g. triethylamine, and used in a solvent, preferably tetrahydrofuran, at high carbon monoxide pressure, preferably 50 to 150 bar, at 150 to 200° C. (see e.g. *J. Org. Chem.* 1993, 58, 5386-92).

Combination of 2-halo or pseudo-halo substituted styrene 8 and carbon monoxide in the presence of a transition metal also allows the preparation of indanone 4 (eq. 3.)). Palladium catalysts are preferred and used with carbon monoxide or molybdenum hexacarbonyl as carbon monoxide source. Preferred solvents are N,N-dimethylformamide, N,N-dimethylacetamide, N-methylpyrrolidone, and 1,4-dioxane which are preferably employed at 20 to 150° C. by conventional heating or microwave irradiation. Pyridine and tetrabutylammonium chloride are preferred additives for this transformation (see e.g. *J. Am. Chem. Soc.* 2003, 125, 4804-7 and *J. Org. Chem.* 2005, 70, 346-9).

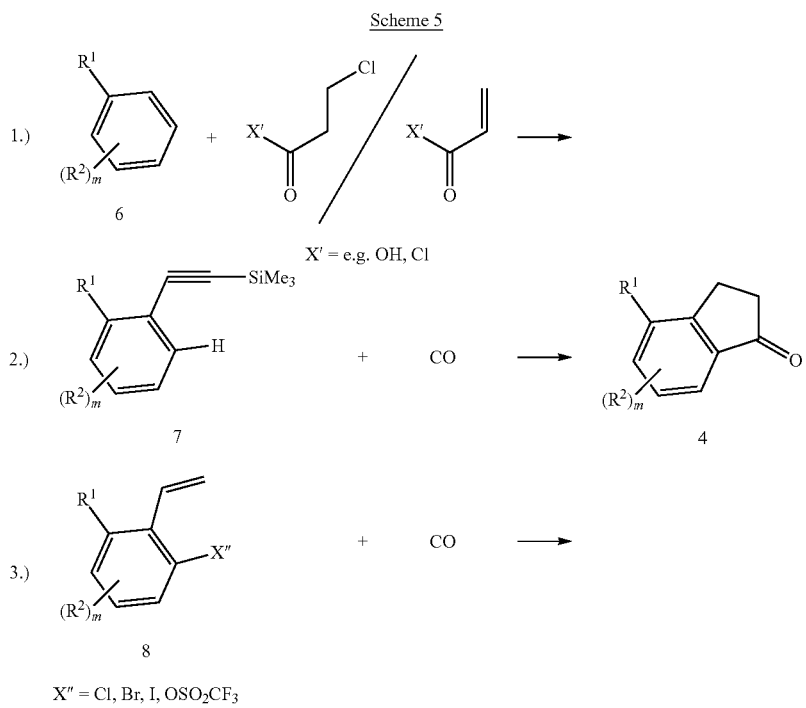

Scheme 5

X' = e.g. OH, Cl

X" = Cl, Br, I, $OSO_2CF_3$

Common synthetic routes to building block 3 are summarized in Scheme 6. 2-Iodo or bromo ether 9 can be transformed into indane 3 via addition of an in situ generated carbon anion or radical to the double bond and subsequent trapping of the cyclic anion by a proton and the cyclic radical by a hydride source (eq. 1.)). nBuLi, iPrMgCl, iPrMgCl*LiCl, Mg, Mg*LiCl, Zn, and Zn*LiCl are preferred reagents to convert the C—I or C—Br bond into a C-M bond (M=Li, MgI, ZnI etc.) with sufficient nucleophilicity to add to the double bond. The reactions with lithium and magnesium reagents are preferably conducted in hexanes, tetrahydrofuran, diethyl ether, 1,2-dimethoxyethane, toluene, or mixtures thereof, at −100 to 60° C. Zn is preferably used in tetrahydrofuran, dimethyl sulfoxide, N-methylpyrrolidinone, or mixtures thereof, at 0 to 100° C. Frequently employed reaction conditions for the radical pathway are, e.g., tributyltin hydride, azobisisobutyronitrile, in benzene, at 60 to 100° C. (see e.g. *J. Org. Chem.* 1987, 52, 4072-8); and NaH$_3$B(CN) in N,N-dimethylformamide under UV irradiation at 20 to 120° C. (see e.g. *Synlett* 2005, 2248-50).

Combination of allyl ether 10 with carbon monoxide is another possibility to obtain indane 3 (equation 2.)). The reaction is preferably conducted with a palladium catalyst in the presence of carbon monoxide or molybdenum hexacarbonyl as carbon monoxide source (see e.g. *Tetrahedron Lett.* 2010, 51, 2102-5).

Starting from benzofuran 11 or dihydrobenzofuran 12 indane 3 is yielded after reduction of the double bond. Hydrogen is the preferred reducing agent which is mainly employed in combination with a transition metal catalyst, such as palladium on carbon, Raney nickel, and PtO$_2$. N,N-dimethylformamide, tetrahydrofuran, ethyl acetate, alcohol, e.g. methanol and ethanol, acetic acid, water, or mixtures thereof are preferably used as solvent, at hydrogen pressures of 1 to 100 bar, and temperatures of 20 to 120° C. This reaction may also be carried out stereoselectively providing compound 3 in enantiomerically enriched or pure form.

The syntheses of the starting compounds in Scheme 6 comprise standard procedures used in organic synthesis. Intermediate 11 can, for example, be prepared as described in Scheme 7. Compound 11 may thus be obtained from compound 13 which, in turn, may be assembled from phenol 14 and ester 15. The latter transformation may be achieved in the presence of a Lewis acid, e.g. sulfuric acid, ZrCl$_4$, InCl$_3$, methanesulfonic acid, p-toluenesulfonic acid, HI, or amberlyst, in toluene, dichloromethane, acetic acid, ethanol, water, or without a solvent in an excess of the Lewis acid, at 0 to 120° C. Transformation of compound 13 into intermediate 11 is preferably accomplished under basic conditions with sodium hydroxide in an aqueous solution at 0 to 100° C.

Scheme 7

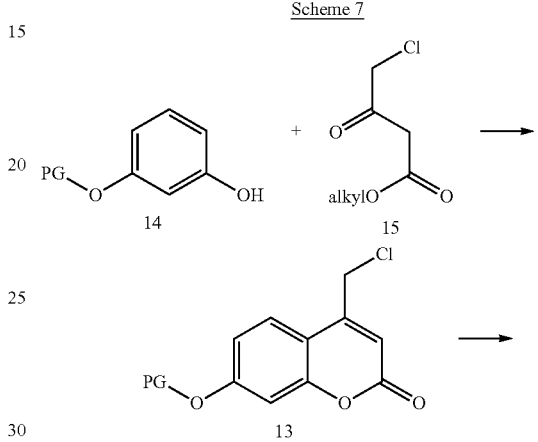

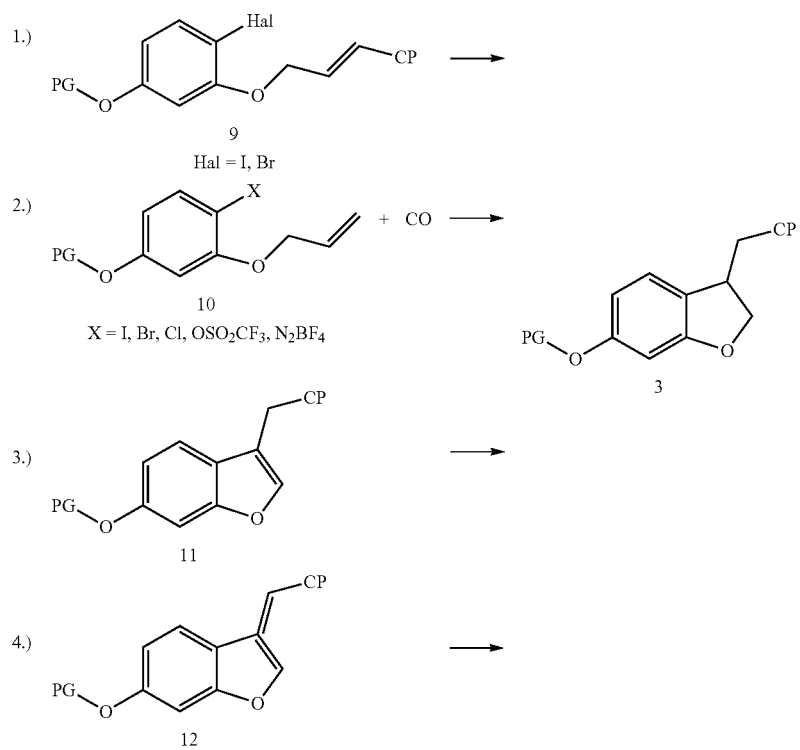

Scheme 6

PG = protective group, e.g., Me, Bn, allyl, tBuMe$_2$Si
CP = masked or protected form of COOH, e.g., CO$_2$C$_{1-4}$-alkyl, CO$_2$CH$_2$aryl, CON(C$_{1-4}$-alkyl)$_2$, CN, CH═CH$_2$, thiazol-2-yl, oxazol-2-yl -continued

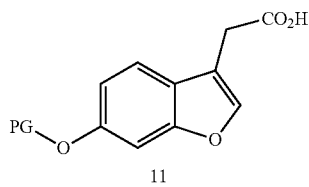

11

PG = protective group, e.g., Me, Bn, allyl, tBuMe$_2$Si

Residue $R^1$ may be attached to the benzo part of the compounds of the invention via a transition metal catalyzed reaction at almost any stage of the reaction sequence (Scheme 8); $R^1$, $R^2$, and m have the meanings as defined hereinbefore and hereinafter. $R^1$ is preferably used as nucleophilic reaction partner bearing a metal residue at the benzylic carbon atom; suited metal residues may be magnesium halides or pseudo halides, zinc halides or pseudo halides, boronic acid, boronic esters, and trifluoroborates. The benzo part is preferably employed as electrophilic reaction partner bearing a leaving group such as Cl, Br, I, triflate, mesylate, or tosylate. Suitable transition metal catalysts are derived from palladium, nickel, copper, or iron. The active catalyst may be an elemental form of the transition metal, such as palladium on carbon or nanoparticles of iron or palladium, or a salt of the transition metal, such as fluoride, chloride, bromide, acetate, triflate, or trifluoroacetate, which are preferably combined with ligands, such as phosphines, e.g. tri-tert-butylphosphine, tricyclohexylphosphine, optionally substituted biphenyl-dicyclohexyl-phosphines, optionally substituted biphenyl-di-tert-butyl-phosphines, 1,1'-bis(diphenylphosphino)-ferrocene, triphenylphosphine, tritolylphosphine, or trifurylphosphine, phosphites, 1,3-disubstituted imidazole carbenes, 1,3-disubstituted imidazolidine carbenes, dibenzylideneacetone, allyl, or nitriles. Depending on the reactvity of the nucleophile, the reaction may be conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, at −10 to 160° C. Additives such as halide salts, e.g. lithium chloride, potassium fluoride, tetrabutylammonium fluoride, hydroxide sources, such as potassium hydroxide, sodium or potassium carbonate, amines, such as triethylamine, diisopropylamine, and ethyldiisopropylamine, silver salts, such as silver triflate, and/or copper salts, such as copper iodide or chloride, may be beneficial or even essential for the reaction to proceed.

The reactivities of the reaction partners (reacting carbons) described may be reversed, i.e. compound 16 is the nucleophile bearing M and compound 17 is the electrophile bearing the leaving group, providing the same product under the same or similar conditions.

Scheme 8

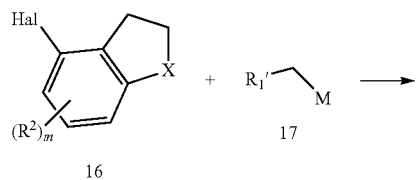

16

-continued

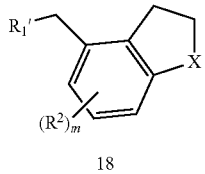

18

Hal = e.g., Cl, Br, I, OSO$_2$CF$_3$
M = e.g., MgCl/Br/I, ZnCl/Br/I, B(OH)$_2$, B(OCMe$_2$CMe$_2$O), BF$_3$K
$R^1$—CH$_2$ = $R^1$ or a precursor of it
X = e.g., C(=O), CH(OH), CH(O-protective group),

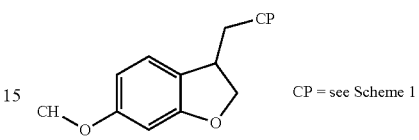

CP = see Scheme 1

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the G-protein-coupled receptor GPR40 with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

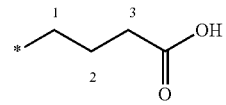

wherein the carboxy group is attached to the third carbon atom of the propyl group. The terms "1-methylpropyl-", "2,2-dimethylpropyl-" or "cyclopropylmethyl-" group represent the following groups:

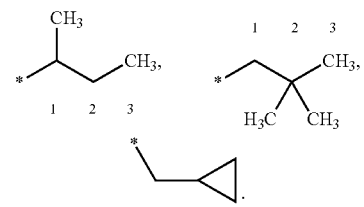

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —$CH$=$CH_2$, —$CH$=$CH$—$CH_3$, —$CH_2$—$CH$=$CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —$CH$=$CH$—, —$CH$=$CH$—$CH_2$—, —$CH_2$—$CH$=$CH$—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —$C$≡$CH$, —$C$≡$C$—$CH_3$, —$CH_2$—$C$≡$CH$.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —$C$≡$C$—, —$C$≡$C$—$CH_2$—, —$CH_2$—$C$≡$C$—.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cylcoalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyl denotes $C_{3-n}$-cylcoalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, unless specified otherwise, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl", unless specified otherwise, means a saturated or unsaturated mono-, bi-, tri- or spirocarbocyclic, preferably mono-, bi- or spirocyclic-ring system containing one or more heteroatoms selected from N, O or $S(O)_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or $S(O)_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

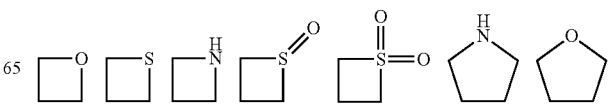

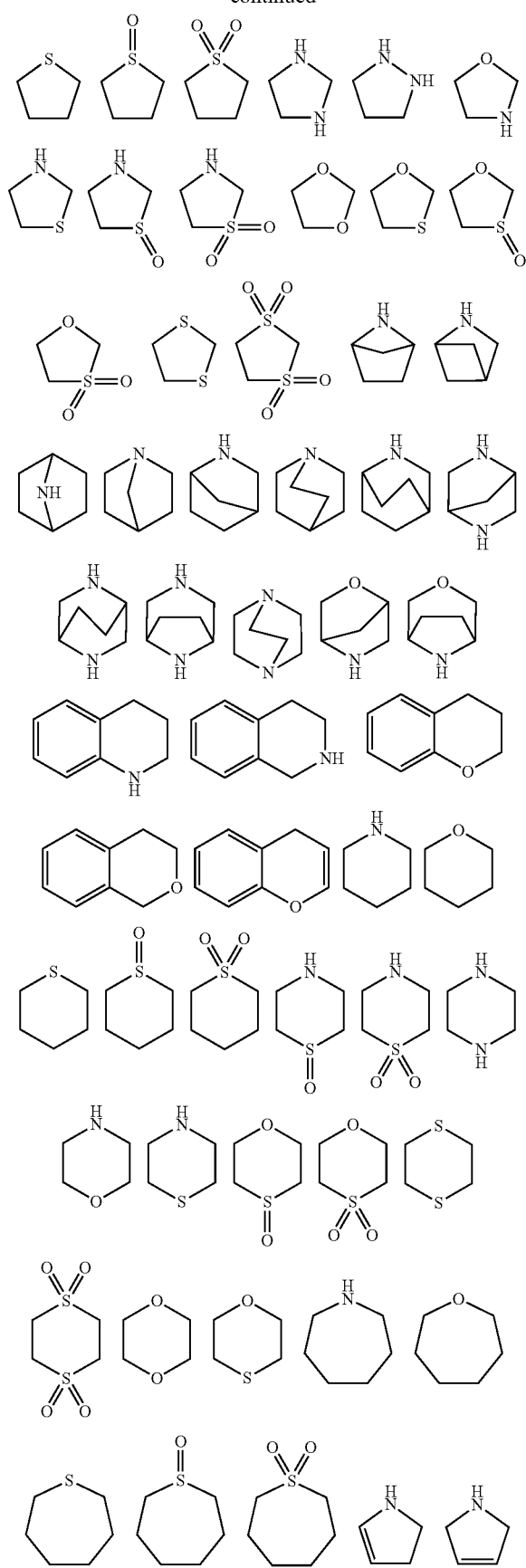
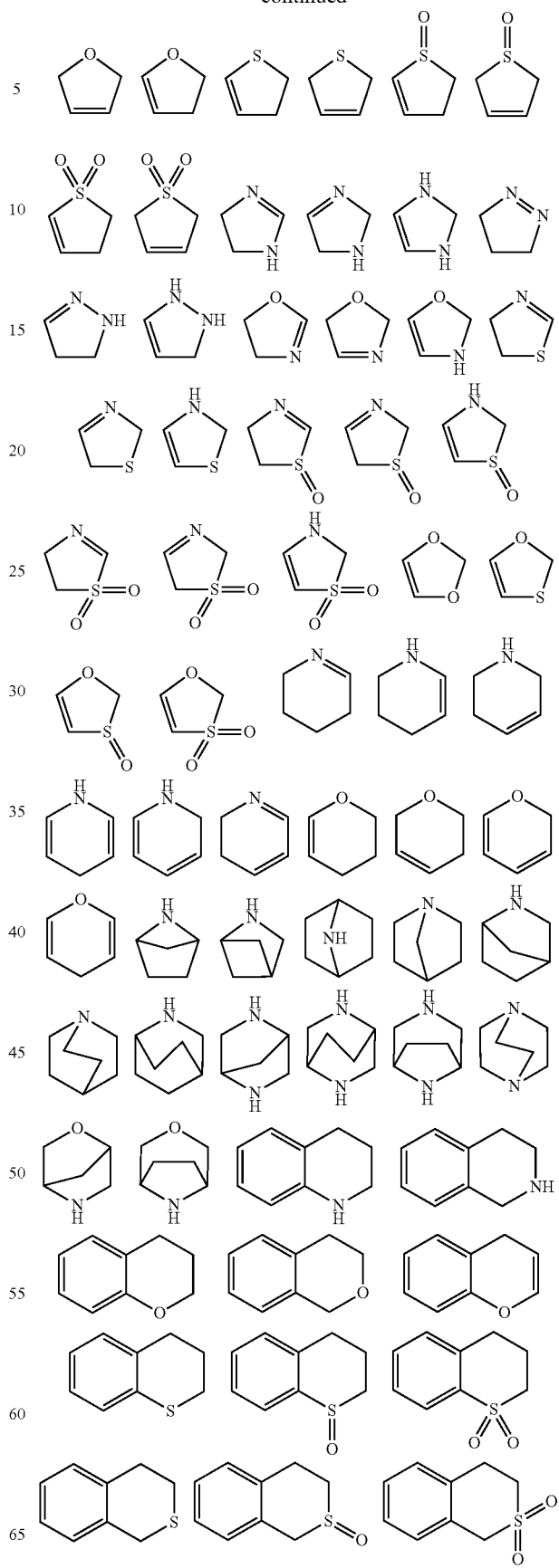

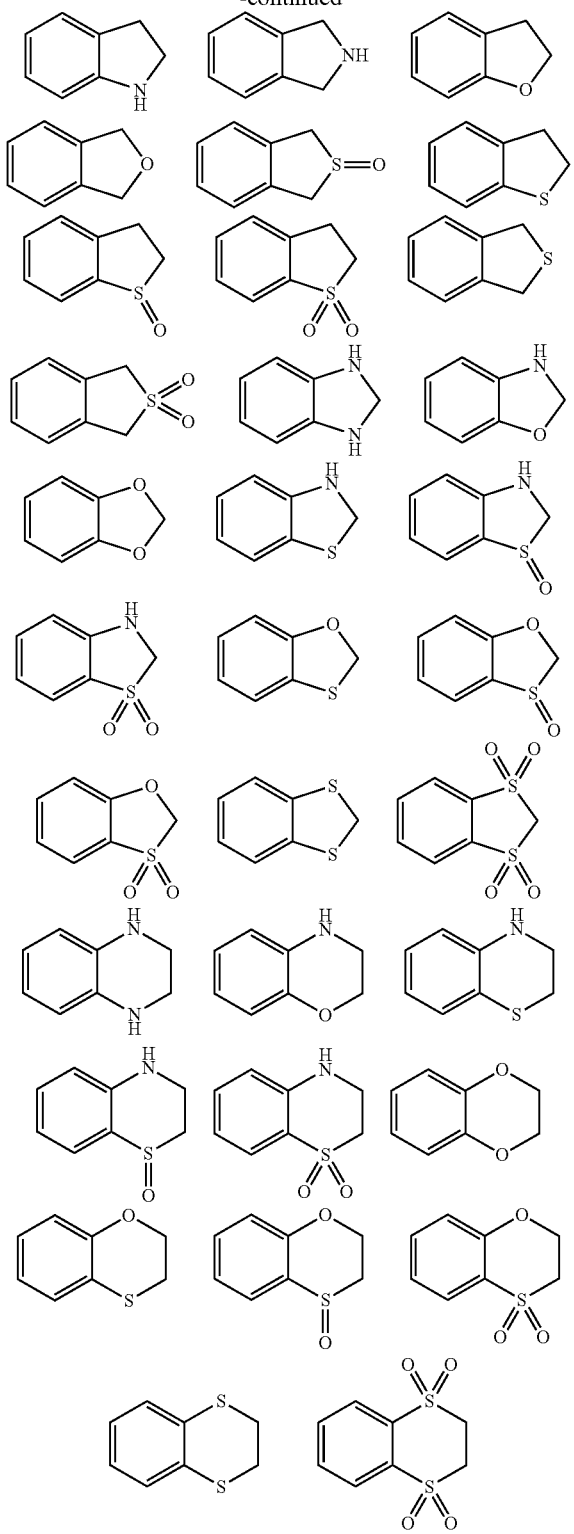

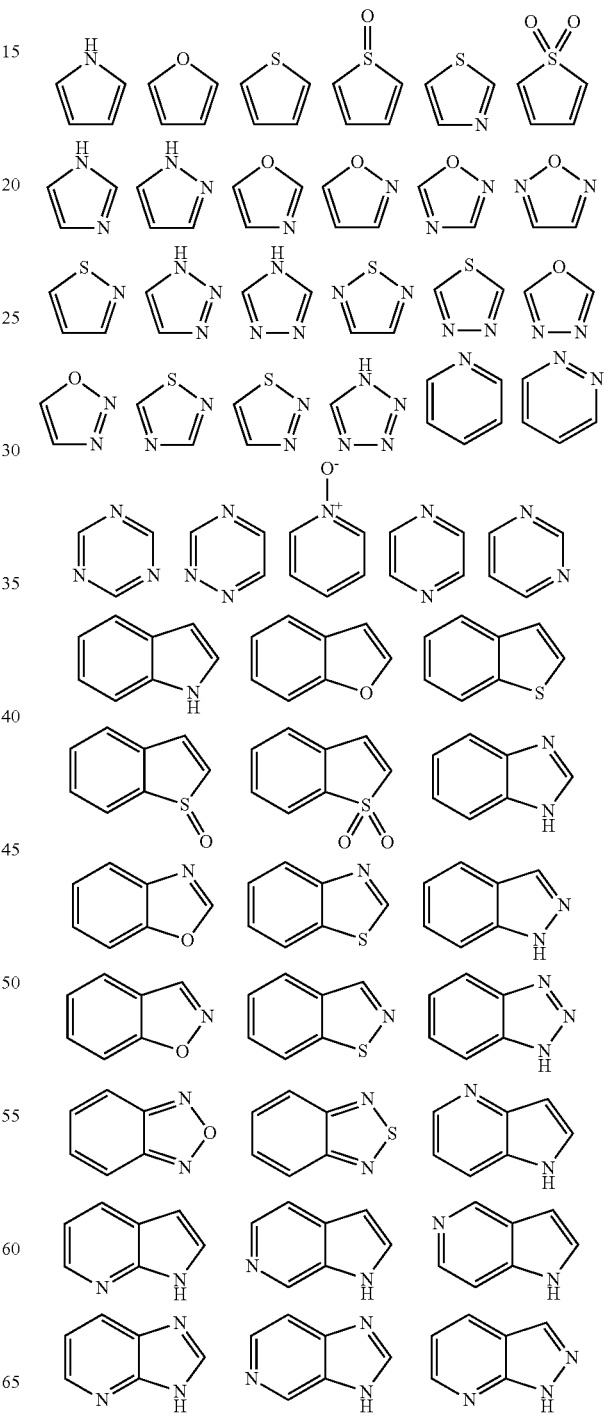

another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

The term "heteroaryl", unless specified otherwise, means a mono- or polycyclic, preferably mono- or bicyclic-ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with -continued

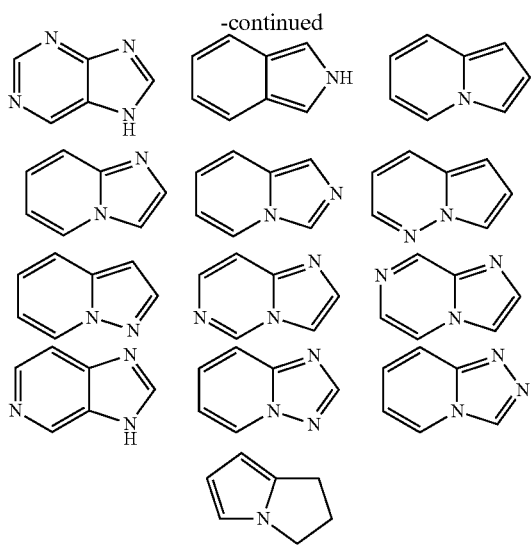

Many of the terms given above may be used repeatedly in the definition of a formula or group and in each case have one of the meanings given above, independently of one another.

Pharmacological Activity

The activity of the compounds of the invention may be demonstrated using the following assays:

Assay I:

$IP_1$ accumulation measurements using the IPOne assay system—1321N1 cells stably expressing human GPR40 receptor (Euroscreen, Belgium) are seeded 24 h before the assay in black clear-bottom collagen-coated 384-well plates in culture medium containing 10% FCS, 1% Na-Pyruvate and 400 μg/mL G418. $IP_1$ is assayed according to the Manufacturer's description (Cisbio Bioassays, France). In brief, the assay is started by substitution of the culture medium by stimulation buffer (Hepes 10 mM, $CaCl_2$ 1 mM, $MgCl_2$ 0.5 mM, KCl 4.2 mM, NaCl 146 mM and glucose 5.5 mM, pH 7.4) without LiCl. Cells are stimulated for 1 hour at 37° C., 10% $CO_2$ by addition of the compounds that are diluted in stimulation buffer containing LiCl yielding a final LiCl concentration of 50 mM. Assays are stopped by adding HTRF-conjugates (IP1-d2 and Anti-IP1 cryptate Tb) and lysis buffer, provided by the manufacturer. After an incubation time of 1 hour at room temperature plates are measured using an EnVision™, Perkin Elmer. The obtained fluorescence ratios at 665/615 nM are then used to calculate the $pEC_{50}$ values using GraphPad Prism 5 (Graphpad Software Inc, USA) by interpolation using an $IP_1$ reference curve and subsequent sigmoidal curve fitting allowing for a variable hill slope.

The compounds according to the invention typically have $EC_{50}$ values in the range from about 1 nM to about 10 μM, preferably less than 1 μM, more preferably less than 100 nM.

$EC_{50}$ values for compounds according to the invention determined in Assay I are shown in the following Table. The number of the compound corresponds to the number of the Example in the experimental section.

| Example | $EC_{50}$ [nM] | Example | $EC_{50}$ [nM] | Example | $EC_{50}$ [nM] | Example | $EC_{50}$ [nM] |
|---|---|---|---|---|---|---|---|
| 1 | 5 | 2 | 36 | 3 | 24 | 4 | 5 |
| 5 | 6 | 6 | 8 | 7 | 18 | 8 | 325 |
| 9 | 29 | 10 | 3 | 11 | 12 | 12 | 479 |
| 13 | 5 | 14 | 4 | 15 | 35 | 16 | 5 |

Assay II:

$IP_1$ accumulation measurements using the IPOne assay system—1321N1 cells stably expressing human GPR40 receptor (Euroscreen, Belgium) are seeded 24 h before the assay in white 384-well plates in culture medium containing 10% FCS, 1% Na-Pyruvate and 400 μg/mL G418. $IP_1$ is assayed according to the manufacturer's description (Cisbio Bioassays, France). In brief, the assay is started by substitution of the culture medium by stimulation buffer (Hepes 10 mM, $CaCl_2$ 1 mM, $MgCl_2$ 0.5 mM, KCl 4.2 mM, NaCl 146 mM, glucose 5.5 mM and LiCl 50 mM, pH 7.4). Cells are stimulated for 1 h at 37° C., 5% $CO_2$ by addition of the compounds that are diluted in stimulation buffer containing LiCl. Assays are stopped by adding HTRF-conjugates (IP1-d2 and Anti-IP1 cryptate Tb) and lysis buffer, provided by the manufacturer. After an incubation time of 1 h at room temperature plates are measured using an EnVision™, Perkin Elmer. The obtained fluorescence ratios at 665/615 nM are then used to calculate the $pEC_{50}$ values using Assay Explorer 3.3 Software (Accelrys, Inc.) by interpolation using an $IP_1$ reference curve and subsequent sigmoidal curve fitting allowing for a variable hill slope.

The compounds according to the invention typically have $EC_{50}$ values in the range from about 1 nM to about 10 μM, preferably less than 1 μM, more preferably less than 100 nM.

$EC_{50}$ values for compounds according to the invention determined in Assay II are shown in the following table. The number of the compound corresponds to the number of the Example in the experimental section.

| Example | $EC_{50}$ [nM] | Example | $EC_{50}$ [nM] | Example | $EC_{50}$ [nM] | Example | $EC_{50}$ [nM] |
|---|---|---|---|---|---|---|---|
| 17 | 24 | 18 | 27 | 19 | 23 | 20 | 589 |
| 21 | 15 | 22 | 6 | 23 | 11 | 24 | 12 |
| 25 | 2 | 26 | 2 | 27 | 5 | 28 | 5 |
| 29 | 3 | 30 | 2 | 31 | 2 | 32 | 8 |
| 33 | 2 | 34 | 4 | 35 | 2 | 36 | 2 |
| 37 | 4 | 38 | 1 | 40 | 5 | | |

In view of their ability to modulate the activity of the G-protein-coupled receptor GPR40, in particular an agonistic activity, the compounds of general formula I according to the invention, including the corresponding salts thereof, are theoretically suitable for the treatment of all those diseases or conditions which may be affected or which are mediated by the activation of the G-protein-coupled receptor GPR40.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR40 in a patient, preferably in a human.

In yet another aspect the present invention relates to a method for treating a disease or condition mediated by the activation of the G-protein-coupled receptor GPR40 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR40 embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:
- for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);
- for improving glycaemic control and/or reducing fasting plasma glucose, postprandial plasma glucose and/or the glycosylated haemoglobin HbA1c;
- for preventing, delaying, slowing or reversing the progression of disrupted glucose tolerance, insulin resistance and/or metabolic syndrome to type 2 diabetes;
- for preventing, delaying, slowing the progression of or treating a condition or a disease selected from among the complications of diabetes, such as for example retinopathy, nephropathy or neuropathies, diabetic foot, ulcers or macroangiopathies;
- for reducing weight or preventing weight gain or assisting weight loss;
- for preventing or treating the degradation of pancreatic beta cells and/or improving and/or restoring the functionality of pancreatic beta cells and/or restoring the functionality of pancreatic insulin secretion;
- for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR40, in particular diseases or conditions as described hereinbefore and hereinafter.

In yet another aspect the present invention relates a method for treating a disease or condition mediated by the activation of the G-protein-coupled receptor GPR40 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The terms "ambient temperature" and "room temperature" are used interchangeably and designate a temperature of about 20° C.

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm.

Analytical HPLC parameters employed for characterization of products (TFA denotes trifluoroacetic acid):

| Method: | 1 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [$H_2O$, 0.1% TFA] | % Solvent [Methanol] | Flow [mL/min] | Temperature [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method: | 2 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [$H_2O$, 0.1% TFA] | % Solvent [$CH_3CN$] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 3 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [$H_2O$, 0.1% TFA] | % Solvent [$CH_3CN$] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |

| Gradient/Solvent Time [min] | % Solvent [H₂O, 0.1% TFA] | % Solvent [CH₃CN] | Flow [mL/min] | Temperature [° C.] |
|---|---|---|---|---|
| 1.25 | 0 | 100 | 3 | 60 |
| 1.40 | 0 | 100 | 3 | 60 |

Method: 4
Device: Agilent 1200 with DA and MS detector
Column: Sunfire, 3 × 30 mm, 2.5 μm
Column Supplier: Waters

| Gradient/Solvent Time [min] | % Solvent [H₂O, 0.1% TFA] | % Solvent [CH₃CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 5
Device: Agilent 1100 with DA and MS detector
Column: XBridge C18, 4.6 × 30 mm, 3.5 μm
Column Supplier: Waters

| Gradient/Solvent Time [min] | % Solvent [H₂O, 0.1% HCOOH] | % Solvent [Methanol] | Flow [mL/min] | Temperature [° C.] |
|---|---|---|---|---|
| 0.0 | 50 | 50 | 4 | 60 |
| 0.15 | 50 | 50 | 4 | 60 |
| 1.7 | 0 | 100 | 4 | 60 |
| 2.25 | 0 | 100 | 4 | 60 |

Method: 6
Device: Agilent 1200 with DA and MS detector
Column: XBridge C18, 3.0 × 30 mm, 2.5 μm
Column Supplier: Waters

| Gradient/Solvent Time [min] | % Solvent [H₂O, 0.1% NH₄OH] | % Solvent [Acetonitrile] | Flow [mL/min] | Temperature [° C.] |
|---|---|---|---|---|
| 0.0 | 97.0 | 3.0 | 2.2 | 60 |
| 0.2 | 97.0 | 3.0 | 2.2 | 60 |
| 1.2 | 0.0 | 100.0 | 2.2 | 60 |
| 1.25 | 0.0 | 100.0 | 3.0 | 60 |
| 1.4 | 0.0 | 100.0 | 3.0 | 60 |

Method: 7
Device: Agilent 1200 with DA and MS detector
Column: XBridge C18, 3 × 30 mm, 2.5 μm
Column Supplier: Waters

| Gradient/Solvent Time [min] | % Solvent [H₂O, 0.1% NH₃] | % Solvent [CH₃CN] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 8
Device: Agilent 1200 with DA and MS detector
Column: Sunfire C18, 3 × 30 mm, 2.5 μm
Column Supplier: Waters

| Gradient/Solvent Time [min] | % Solvent [H₂O, 0.1% TFA] | % Solvent [CH₃CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 9
Device: Agilent 1200 with DA and MS detector
Column: Sunfire, 3 × 30 mm, 2.5 μm
Column Supplier: Waters

| Gradient/Solvent Time [min] | % Solvent [H₂O, 0.1% TFA] | % Solvent [CH₃CN] | Flow [ml/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

The Examples that follow are intended to illustrate the present invention without restricting it:

Intermediate 1

{(S)-6-[(R)-4-benzyl-5-cyano-indan-1-yloxy]-2,3-dihydro-benzofuran-3-yl}-acetic acid methyl ester

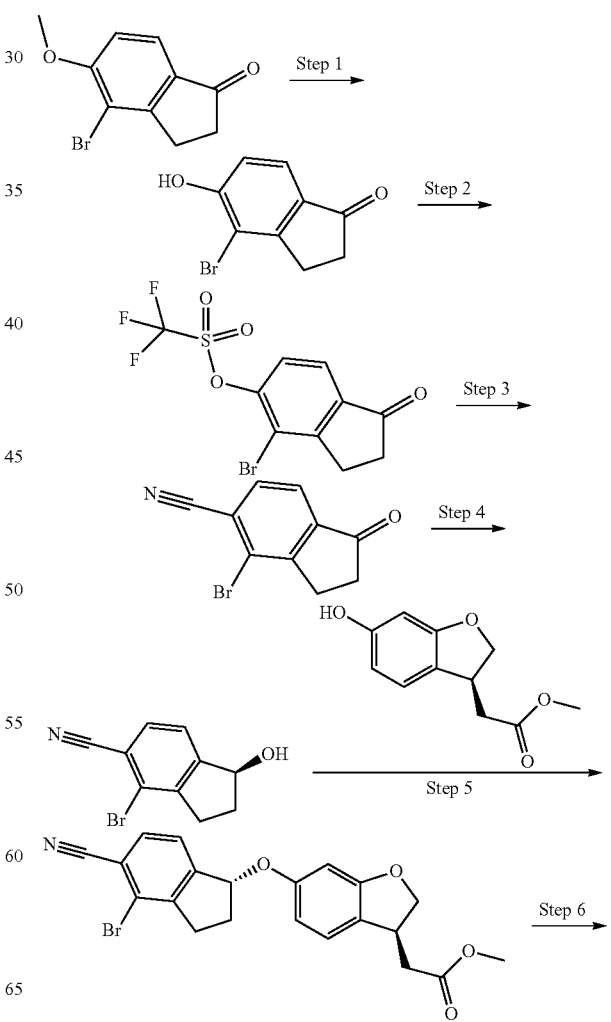

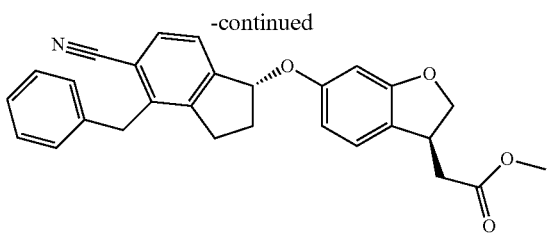

Step 1: 4-bromo-5-hydroxy-indan-1-one

Sodium methanethiolate (2.00 g) is added to a microwave vial charged with a stir bar, 4-bromo-5-methoxy-indan-1-one (1.58 g), and N,N-dimethylformamide (10 mL). The vial is sealed and the mixture is heated to 130° C. and stirred at this temperature for 2 h. After cooling to room temperature, the mixture is partitioned between ethyl acetate and 1 N aqueous HCl solution. The aqueous phase is separated and extracted with ethyl acetate. The combined organic phases are washed with brine and dried (MgSO$_4$). The solvents are evaporated and the residue is triturated with diethylether. The precipitate is filtered off and dried in vacuo to give the title compound. LC (method 1): $t_R$=0.84 min; Mass spectrum (ESI$^+$): m/z=227/229 (Br) [M+H]$^+$.

Step 2: trifluoro-methanesulfonic acid 4-bromo-1-oxo-indan-5-yl ester

Trifluoromethanesulfonic anhydride (4.0 mL) is added dropwise to a solution of 4-bromo-5-hydroxy-indan-1-one (5.0 g) and 2,6-dimethylpyridine (5.1 mL) in dichloromethane (50 mL) cooled to 0° C. The cooling bath is removed and the mixture is stirred for 2 h at room temperature. The solution is partitioned between saturated aqueous NH$_4$Cl solution and dichloromethane. The organic phase is separated, washed with brine, dried (MgSO$_4$), and concentrated. The residue is chromatographed on silica gel (cyclohexane/ethyl acetate 99:1→50:50) to give the title compound. LC (method 2): $t_R$=1.08 min; Mass spectrum (ESI$^+$): m/z=359/361 (Br) [M+H]$^+$.

Step 3: 4-bromo-1-oxo-indan-5-carbonitrile

Zn(CN)$_2$ (0.60 g) and 1,1'-bis(diphenylphosphino)-ferrocene (0.92 g) are added to a solution of trifluoro-methanesulfonic acid 4-bromo-1-oxo-indan-5-yl ester (5.90 g) in N,N-dimethylformamide (30 mL) at room temperature. The mixture is purged with Ar for 5 min prior to addition of tris(dibenzylideneacetone)dipalladium(0) (760 mg). The mixture is heated to 70° C. and stirred at this temperature for 1 h. After cooling to room temperature, ethyl acetate is added and the resulting mixture is washed with water and brine. The organic phase is dried (MgSO$_4$) and concentrated. The residue is chromatographed on silica gel (cyclohexane/ethyl acetate 99:1→50:50) to give the title compound. LC (method 2): $t_R$=0.88 min; Mass spectrum (ESI$^-$): m/z=234/236 (Br) [M−H]$^-$.

Step 4: (S)-4-bromo-1-hydroxy-indan-5-carbonitrile

Formic acid (1.8 mL) is added to a solution of triethylamine (5.7 mL) in dichloromethane (30 mL) chilled in an ice bath. 4-Bromo-1-oxo-indan-5-carbonitrile (3.20 g) is added and the flask is purged with Ar for 5 min. Chloro{[(1S,2S)-(−)-2-amino-1,2-diphenylethyl](4-toluenesulfonyl)amido}-(mesitylene)ruthenium(II) (0.40 g; alternatively, the catalyst is formed in situ from N-[(1S,2S)-2-amino-1,2-diphenylethyl]-4-methylbenzenesulfonamide and dichloro(p-cymene)-ruthenium(II) dimer) is added and the mixture is stirred at room temperature for 2 h. The mixture is diluted with dichloromethane and washed with water and brine and dried (MgSO$_4$). The solvent is evaporated and the residue is chromatographed on silica gel (cyclohexane/ethyl acetate 80:20→20:80) to give the title compound. LC (method 2): $t_R$=0.84 min; Mass spectrum (ESI$^+$): m/z=260/262 (Br) [M+Na]$^+$.

Step 5: {(S)-6-[(R)-4-bromo-5-cyano-indan-1-yloxy]-2,3-dihydro-benzofuran-3-yl}-acetic acid methyl ester A solution of di-tert-butyl azodicarboxylate (3.30 g) in tetrahydrofuran (5 mL) is added dropwise over 45 min to a solution of (S)-(6-hydroxy-2,3-dihydro-benzofuran-3-yl)-acetic acid methyl ester (for preparation see WO 2008001931; 2.10 g), (S)-4-bromo-1-hydroxy-indan-5-carbonitrile (2.40 g) and tri-n-butyl-phosphine (3.8 mL) in tetrahydrofuran (25 mL) at −10° C. The resulting solution is stirred for 30 min and then diluted with ethyl acetate. The resulting solution is washed with water and brine and dried (MgSO$_4$). The solvent is evaporated and the residue is chromatographed on silica gel (cyclohexane/ethyl acetate 99:1→70:30) to give the title compound. LC (method 2): $t_R$=1.15 min; Mass spectrum (ESI$^+$): m/z=428/430 (Br) [M+H]$^+$.

Step 6: {(S)-6-[(R)-4-benzyl-5-cyano-indan-1-yloxy]-2,3-dihydro-benzofuran-3-yl}-acetic acid methyl ester A flask charged with a stir bar, {(S)-6-[(R)-4-bromo-5-cyano-indan-1-yloxy]-2,3-dihydro-benzofuran-3-yl}-acetic acid methyl ester (0.10 g), and tetrahydrofuran (1 mL) is purged with Ar for 5 min. Benzylzinc bromide (0.5 mol/L in tetrahydrofuran, 1.5 mL) and tetrakis(triphenylphosphine) palladium (30 mg) are added and the mixture is heated to 60° C. The mixture is stirred at 60° C. overnight and then cooled to room temperature. Aqueous NH$_4$Cl solution is added and the resulting mixture is extracted with ethyl acetate. The combined extracts are dried (MgSO$_4$) and concentrated. The crude title compound is used without further purification. LC (method 4): $t_R$=1.23 min; Mass spectrum (ESI$^+$): m/z=462 [M+Na]$^+$.

Intermediate 2

{(S)-6-[(R)-4-Bromo-7-fluoro-indan-1-yloxy]-2,3-dihydro-benzofuran-3-yl}-acetic acid methyl ester

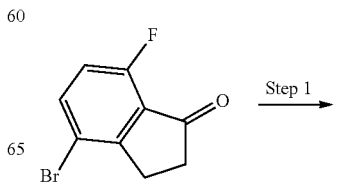

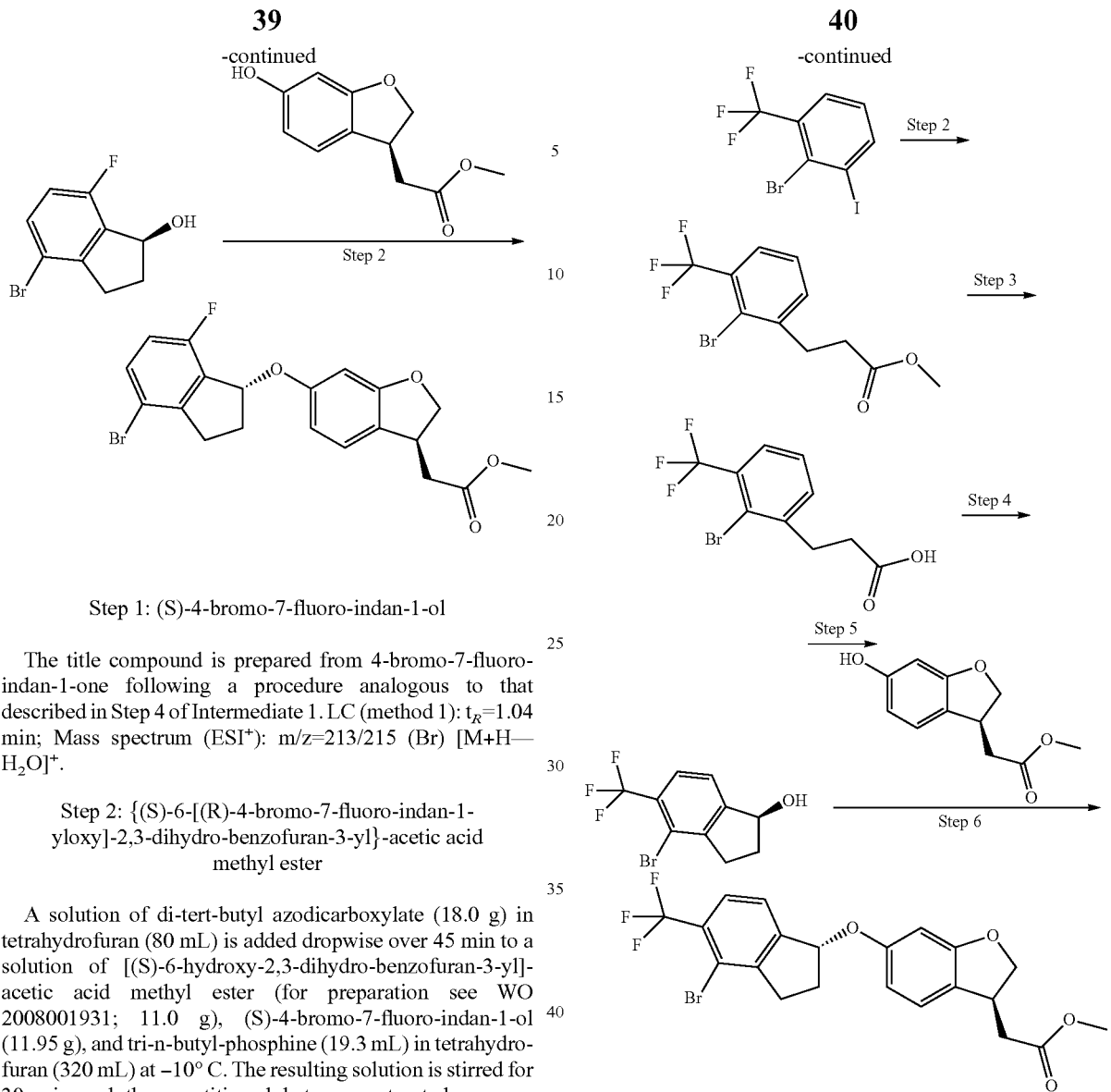

Step 1: (S)-4-bromo-7-fluoro-indan-1-ol

The title compound is prepared from 4-bromo-7-fluoro-indan-1-one following a procedure analogous to that described in Step 4 of Intermediate 1. LC (method 1): $t_R$=1.04 min; Mass spectrum (ESI$^+$): m/z=213/215 (Br) [M+H—H$_2$O]$^+$.

Step 2: {(S)-6-[(R)-4-bromo-7-fluoro-indan-1-yloxy]-2,3-dihydro-benzofuran-3-yl}-acetic acid methyl ester A solution of di-tert-butyl azodicarboxylate (18.0 g) in tetrahydrofuran (80 mL) is added dropwise over 45 min to a solution of [(S)-6-hydroxy-2,3-dihydro-benzofuran-3-yl]-acetic acid methyl ester (for preparation see WO 2008001931; 11.0 g), (S)-4-bromo-7-fluoro-indan-1-ol (11.95 g), and tri-n-butyl-phosphine (19.3 mL) in tetrahydrofuran (320 mL) at −10° C. The resulting solution is stirred for 30 min and then partitioned between saturated aqueous NaHCO$_3$ solution and dichloromethane. The aqueous phase is separated and extracted with dichloromethane. The combined organic phases are dried (MgSO$_4$) and concentrated. The residue is chromatographed on silica gel (cyclohexane/ethyl acetate 90:10→70:30) to give the title compound. LC (method 1): $t_R$=1.41 min; Mass spectrum (ESI$^+$): m/z=421/423 (Br) [M+H]$^+$.

Intermediate 3

{(S)-6-[(R)-4-Bromo-5-trifluoromethyl-indan-1-yloxy]-2,3-dihydro-benzofuran-3-yl}-acetic acid methyl ester

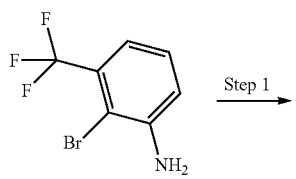

Step 1: 2-bromo-1-iodo-3-trifluoromethyl-benzene

An ice-cold solution of NaNO$_2$ (0.15 g) in water (0.5 mL) is added to a mixture of 2-bromo-3-trifluoromethyl-aniline (0.48 g), concentrated H$_2$SO$_4$ (2 mL), and water (1.8 mL) at ca. 5° C. The mixture is stirred in the cooling bath for 20 min and then poured into a solution of KI (0.56 g) and I$_2$ (0.56 g) in water (0.5 mL). After ceasing of gas evolution, the mixture is heated to 40° C. and stirred at this temperature for 1 h. The mixture is cooled to room temperature and aqueous Na$_2$SO$_3$ solution is added. The resulting mixture is extracted with ethyl acetate and the combined extracts are dried (Na$_2$SO$_4$) and concentrated. The solvent is evaporated and the residue is chromatographed (cyclohexane/ethyl acetate 95:5→90:10) to give the title compound.

Step 2: 3-(2-bromo-3-trifluoromethyl-phenyl)-propionic acid methyl ester

A microwave suited vial charged with a stir bar, 2-bromo-1-iodo-3-trifluoromethyl-benzene (4.04 g), N,N-diisopropylethylamine (4.0 mL), acrolein dimethyl acetal (1.76 g), tetrabutylammonium chloride (3.30 g), and dry N,N-dimethylformamide (10 mL) is purged with Ar for 5 min. Palladium(II) acetate (0.13 g) is added, the vial is sealed, and the mixture is stirred for 20 min at 120° C. in a microwave oven. After cooling to room temperature, the mixture is diluted with ethyl acetate and the resulting mixture is washed with 1 M aqueous HCl solution and brine and dried ($Na_2SO_4$). The solvent is evaporated and the residue is chromatographed (cyclohexane/ethyl acetate 90:10) to give the title compound.

Step 3:
3-(2-bromo-3-trifluoromethyl-phenyl)-propionic acid

The title compound is prepared from 3-(2-bromo-3-trifluoromethyl-phenyl)-propionic acid methyl ester following a procedure analogous to that described in Example 1. LC (method 5): $t_R$=0.93 min; Mass spectrum (ESI$^-$): m/z=295/297 (Br) [M–H]$^-$.

Step 4: 4-bromo-5-trifluoromethyl-indan-1-one 3-(2-Bromo-3-trifluoromethyl-phenyl)-propionic acid (3.25 g) in trifluoromethane-sulfonic acid (30 ml) is stirred at 75° C. for 2.5 h. After cooling to room temperature, the mixture is poured into water and the resulting mixture is extracted with ethyl acetate. The combined organic extract is washed with aqueous $NaHCO_3$ solution, dried ($Na_2SO_4$), and concentrated. The residue is chromatographed on silica gel (cyclohexane/ethyl acetate 90:10→80:20) to afford the title compound. LC (method 5): $t_R$=0.90 min.

Step 5: (S)-4-bromo-5-trifluoromethyl-indan-1-ol

The title compound is prepared from 4-bromo-5-trifluoromethyl-indan-1-one following a procedure analogous to that described in Step 4 of Intermediate 1. LC (method 5): $t_R$=0.94 min; Mass spectrum (ESI$^-$): m/z=279/281 (Br) [M–H]$^-$.

Step 6: {(S)-6-[(R)-4-bromo-5-trifluoromethyl-indan-1-yloxy]-2,3-dihydro-benzofuran-3-yl}-acetic acid methyl ester The title compound is prepared from [(S)-6-hydroxy-2,3-dihydro-benzofuran-3-yl]-acetic acid methyl ester and (S)-4-bromo-5-trifluoromethyl-indan-1-ol following a procedure analogous to that described in Step 2 of Intermediate 2. LC (method 5): $t_R$=1.62 min; Mass spectrum (ESI$^+$): m/z=471/473 (Br) [M+H]$^+$.

Intermediate 4

{(S)-6-[(R)-4-(6-Chloro-pyridin-3-ylmethyl)-5-cyano-indan-1-yloxy]-2,3-dihydro-benzofuran-3-yl}-acetic acid methyl ester

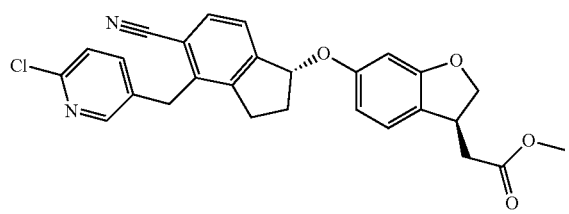 [SMILES: COC(=O)C[C@@H]1COc2cc(O[C@@H]3CCc4c3ccc(C#N)c4Cc3ccc(Cl)nc3)ccc21]

The title compound is prepared from {(S)-6-[(R)-4-bromo-5-cyano-indan-1-yloxy]-2,3-dihydro-benzofuran-3-yl}-acetic acid methyl ester and 6-chloro-pyridin-3-ylmethylzinc chloride following a procedure analogous to that described in Step 6 of Intermediate 1. LC (method 4): $t_R$=1.17 min; Mass spectrum (ESI$^+$): m/z=475/477 [M+H]$^+$.

Intermediate 5

{(S)-6-[(R)-5-cyano-4-(3-methoxy-benzyl)-indan-1-yloxy]-2,3-dihydro-benzofuran-3-yl}-acetic acid methyl ester

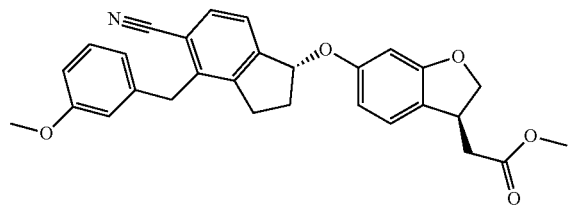

The title compound is prepared from {(S)-6-[(R)-4-bromo-5-cyano-indan-1-yloxy]-2,3-dihydro-benzofuran-3-yl}-acetic acid methyl ester and 3-methoxy-benzylzinc chloride following a procedure analogous to that described in Step 6 of Intermediate 1. LC (method 4): $t_R$=1.22 min; Mass spectrum (ESI$^+$): m/z=492 [M+Na]$^+$.

Intermediate 6

{(S)-6-[(R)-5-cyano-4-(4-methoxy-benzyl)-indan-1-yloxy]-2,3-dihydro-benzofuran-3-yl}-acetic acid methyl ester

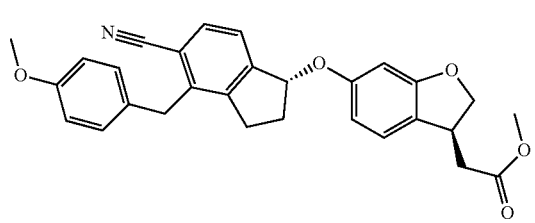 [SMILES: COC(=O)C[C@@H]1COc2cc(O[C@@H]3CCc4c3ccc(C#N)c4Cc3ccc(OC)cc3)ccc21]

The title compound is prepared from {(S)-6-[(R)-4-bromo-5-cyano-indan-1-yloxy]-2,3-dihydro-benzofuran-3-yl}-acetic acid methyl ester and 4-methoxy-benzylzinc chloride following a procedure analogous to that described in Step 6 of Intermediate 1. LC (method 4): $t_R$=1.22 min; Mass spectrum (ESI$^+$): m/z=492 [M+Na]$^+$.

Intermediate 7

{(S)-6-[(R)-5-cyano-4-(2,6-dimethyl-benzyl)-indan-1-yloxy]-2,3-dihydro-benzofuran-3-yl}-acetic acid methyl ester

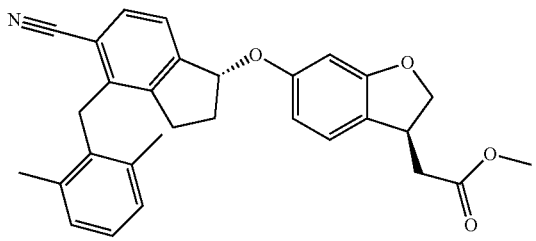 [SMILES: COC(=O)C[C@@H]1COc2cc(O[C@@H]3CCc4c3ccc(C#N)c4Cc3c(C)cccc3C)ccc21]

A flask charged with a stir bar and anhydrous LiCl (49 mg) is heated to 180° C. under high vacuum (ca. 1 mbar). After 30 min the flask is cooled to room temperature, filled with Ar, and Zn powder (84 mg) is added under Ar atmosphere. The flask is reevacuated (ca. 1 mbar) and heated to 180° C. After another 30 min the flask is cooled to room temperature and filled with Ar again. Tetrahydrofuran (dry, 0.5 mL) is added and the Zn is activated with 1,2-dibromoethane (2 μL) and trimethylsilyl chloride (1.5 μL) (for comparison see e.g. *Synthesis* 2009, 681-6). A solution of 2,6-dimethylbenzyl bromide (0.23 g) in tetrahydrofuran (dry, 2 mL) is added dropwise. The mixture is stirred for 30 min prior to addition of {(S)-6-[(R)-4-bromo-5-cyano-indan-1-yloxy]-2,3-dihydro-benzofuran-3-yl}-acetic acid methyl ester (0.10 g) in tetrahydrofuran (dry, 2 mL) and [1,3-bis(2,6-diisopropylphenyl)imidazol-2-ylidene]-(3-chloropyridyl)-palladium(II) dichloride (Pd-PEPPSI-IPr, 20 mg). The mixture is heated to 60° C. and stirred at this temperature overnight. After cooling to room temperature, aqueous NH$_4$Cl solution is added and the resulting mixture is extracted with ethyl acetate. The combined extracts are dried (MgSO$_4$) and concentrated. The residue is purified by HPLC on reversed phase (MeCN/water/NH$_4$OH) to give the title compound. LC (method 4): t$_R$=1.28 min; Mass spectrum (ESI$^+$): m/z=468 [M+H]$^+$.

Intermediate 8

{(S)-6-[(R)-5-cyano-4-(2-methyl-benzyl)-indan-1-yloxy]-2,3-dihydro-benzofuran-3-yl}-acetic acid methyl ester

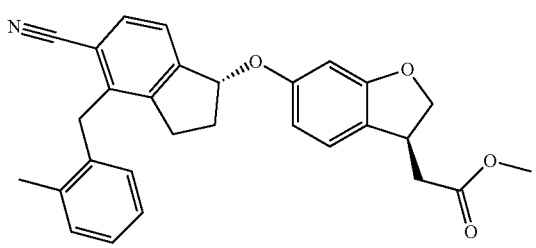 [SMILES: COC(=O)C[C@@H]1COc2cc(O[C@@H]3CCc4c3ccc(C#N)c4Cc3ccccc3C)ccc21]

The title compound is prepared from {(S)-6-[(R)-4-bromo-5-cyano-indan-1-yloxy]-2,3-dihydro-benzofuran-3-yl}-acetic acid methyl ester and 2-methyl-benzylzinc chloride following a procedure analogous to that described in Step 6 of Intermediate 1. LC (method 4): t$_R$=1.22 min; Mass spectrum (ESI$^+$): m/z=476 [M+Na]$^+$.

Intermediate 9

{(S)-6-[(R)-5-cyano-4-(4-methylsulfanyl-benzyl)-indan-1-yloxy]-2,3-dihydro-benzofuran-3-yl}-acetic acid methyl ester

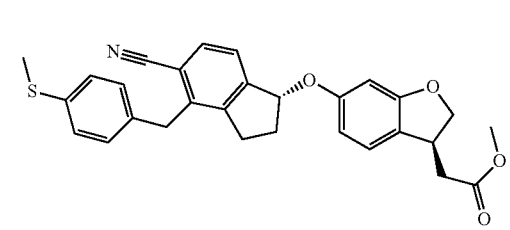 [SMILES: COC(=O)C[C@@H]1COc2cc(O[C@@H]3CCc4c3ccc(C#N)c4Cc3ccc(SC)cc3)ccc21]

The title compound is prepared from {(S)-6-[(R)-4-bromo-5-cyano-indan-1-yloxy]-2,3-dihydro-benzofuran-3-yl}-acetic acid methyl ester and 4-methylsulfanyl-benzyl bromide following a procedure analogous to that described for Intermediate 7. LC (method 4): t$_R$=1.12 min; Mass spectrum (ESI$^+$): m/z=508 [M+Na]$^+$.

Intermediate 10

{(S)-6-[(R)-5-cyano-4-(3-cyano-benzyl)-indan-1-yloxy]-2,3-dihydro-benzofuran-3-yl}-acetic acid methyl ester

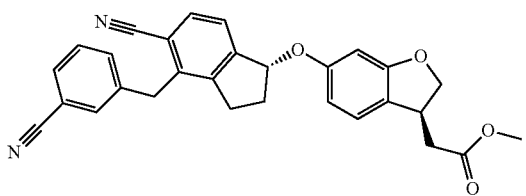 [SMILES: COC(=O)C[C@@H]1COc2cc(O[C@@H]3CCc4c3ccc(C#N)c4Cc3cccc(C#N)c3)ccc21]

The title compound is prepared from {(S)-6-[(R)-4-bromo-5-cyano-indan-1-yloxy]-2,3-dihydro-benzofuran-3-yl}-acetic acid methyl ester and 3-cyano-benzylzinc bromide following a procedure analogous to that described in Step 6 of Intermediate 1. LC (method 4): t$_R$=1.18 min; Mass spectrum (ESI$^+$): m/z=487 [M+Na]$^+$.

Intermediate 11

{(S)-6-[(R)-4-benzyl-5-trifluoromethyl-indan-1-yloxy]-2,3-dihydro-benzofuran-3-yl}-acetic acid methyl ester

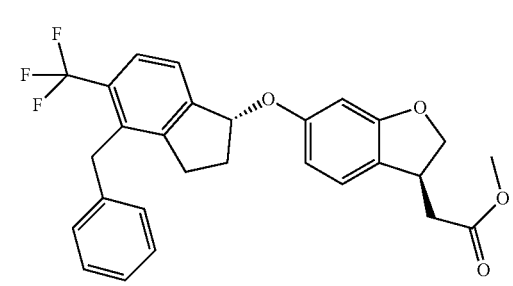 [SMILES: COC(=O)C[C@@H]1COc2cc(O[C@@H]3CCc4c3ccc(C(F)(F)F)c4Cc3ccccc3)ccc21]

The title compound is prepared from {(S)-6-[(R)-4-bromo-5-trifluoromethyl-indan-1-yloxy]-2,3-dihydro-benzofuran-3-yl}-acetic acid methyl ester and benzylzinc bromide following a procedure analogous to that described in Step 6 of Intermediate 1. LC (method 3): $t_R$=0.94 min; Mass spectrum (ESI$^+$): m/z=505 [M+Na]$^+$.

Intermediate 12

{(S)-6-[(R)-4-(4-Acetoxy-benzyl)-5-cyano-indan-1-yloxy]-2,3-dihydro-benzofuran-3-yl}-acetic acid methyl ester

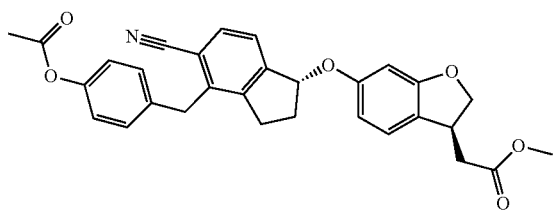 [SMILES: COC(=O)C[C@@H]1COc2cc(O[C@@H]3CCc4c3ccc(C#N)c4Cc3ccc(OC(C)=O)cc3)ccc21]

The title compound is prepared from {(S)-6-[(R)-4-bromo-5-cyano-indan-1-yloxy]-2,3-dihydro-benzofuran-3-yl}-acetic acid methyl ester and 4-acetoxy-benzyl bromide following a procedure analogous to that described for Intermediate 7.

Intermediate 13

{(S)-6-[(R)-7-Fluoro-4-(4-methoxy-benzyl)-indan-1-yloxy]-2,3-dihydro-benzofuran-3-yl}-acetic acid methyl ester

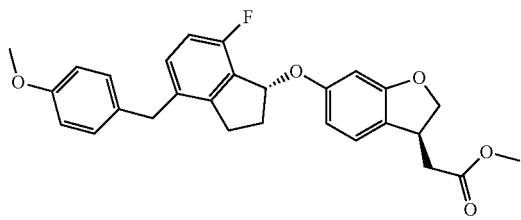

The title compound is prepared from {(S)-6-[(R)-4-bromo-7-fluoro-indan-1-yloxy]-2,3-dihydro-benzofuran-3-yl}-acetic acid methyl ester (84 mg), 4-methoxy-benzylzinc chloride (0.5 mol/L in tetrahydrofuran, 1.2 mL) and tetrakis(triphenylphosphine)-palladium (23 mg). Degassed tetrahydrofuran (1 mL) is added under Ar atmosphere, and the mixture is heated to 60° C. and shaken at this temperature overnight. After cooling to room temperature, the mixture is acidified with 4 N aqueous hydrochloric acid (1 mL) and then neutralized with saturated aqueous ammonia solution. The organic phase is separated, diluted with N,N-dimethylformamide (1 mL), and purified by HPLC on reversed phase (MeCN/water) to give the title compound. LC (method 6): $t_R$=1.16 min.

Intermediate 14

{(S)-6-[(R)-7-Fluoro-4-(3-methoxy-benzyl)-indan-1-yloxy]-2,3-dihydro-benzofuran-3-yl}-acetic acid methyl ester

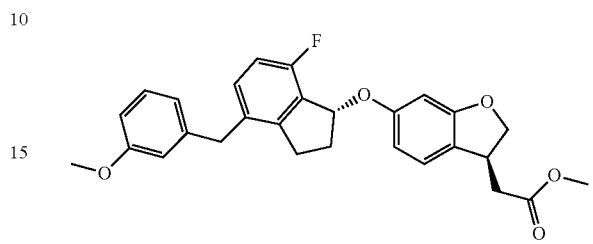

The title compound is prepared from {(S)-6-[(R)-4-bromo-7-fluoro-indan-1-yloxy]-2,3-dihydro-benzofuran-3-yl}-acetic acid methyl ester (84 mg), 3-methoxy-benzylzinc chloride (0.5 mol/L in tetrahydrofuran, 1.2 mL) and tetrakis(triphenylphosphine)-palladium (23 mg). Degassed tetrahydrofuran (1 mL) is added under Ar atmosphere, and the mixture is heated to 60° C. and shaken at this temperature overnight. The mixture is acidified with 4 N aqueous hydrochloric acid (1 mL) and then neutralized with saturated aqueous ammonia solution. The organic phase is separated, diluted with N,N-dimethylformamide (1 mL), and purified by HPLC on reversed phase (MeCN/water) to give the title compound. LC (method 6): $t_R$=1.17 min.

Intermediate 15

{(S)-6-[(R)-(6-Chloro-pyridin-3-ylmethyl)-7-fluoro-indan-1-yloxy]-2,3-dihydro-benzofuran-3-yl}-acetic acid methyl ester

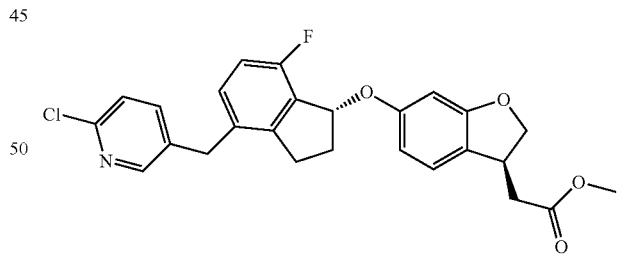

The title compound is prepared from {(S)-6-[(R)-4-bromo-7-fluoro-indan-1-yloxy]-2,3-dihydro-benzofuran-3-yl}-acetic acid methyl ester (84 mg), (2-chloro-pyrid-5-yl)methylzinc chloride (0.5 moL/L in tetrahydrofuran, 1.2 mL) and tetrakis(triphenylphosphine)palladium (23 mg). Degassed tetrahydrofuran (1 mL) is added under Ar atmosphere, and the mixture is heated to 60° C. and shaken at this temperature overnight. The mixture is acidified with 4 N aqueous hydrochloric acid (1 mL) and then neutralized with saturated aqueous ammonia solution. The organic phase is separated, diluted with N,N-dimethylformamide (1 mL), and purified by HPLC on reversed phase (MeCN/water) to give the title compound. LC (method 6): $t_R$=1.04 min.

Intermediate 16

{(S)-6-[(R)-4-Benzyl-7-fluoro-indan-1-yloxy]-2,3-dihydro-benzofuran-3-yl}-acetic acid methyl ester

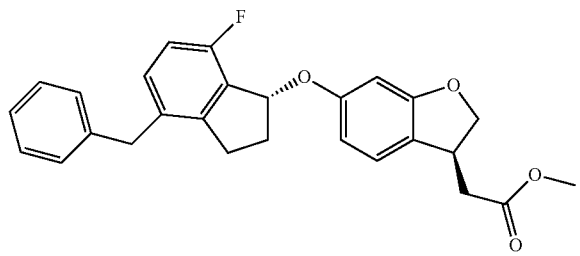 [SMILES: COC(=O)C[C@@H]1COc2cc(O[C@@H]3CCc4c(Cc5ccccc5)ccc(F)c43)ccc21]

The title compound is prepared from {(S)-6-[(R)-4-bromo-7-fluoro-indan-1-yloxy]-2,3-dihydro-benzofuran-3-yl}-acetic acid methyl ester (84 mg), benzylzinc bromide (0.5 mol/L in tetrahydrofuran, 1.2 ml) and tetrakis(triphenylphosphine) palladium (23 mg). Degassed tetrahydrofuran (1 mL) is added under Ar atmosphere, and the mixture is heated to 60° C. and shaken at this temperature overnight. The reaction mixture is acidified with 4 N aqueous hydrochloric acid (1 mL) and then neutralized with saturated aqueous ammonia solution. The organic phase is separated, diluted with N,N-dimethylformamide (1 mL), and purified by HPLC on reversed phase (MeCN/water) to give the title compound. LC (method 6): $t_R$=1.19 min.

Intermediate 17

{(S)-6-[(R)-4-(4-Methylsulfanyl-benzyl)-5-trifluoromethyl-indan-1-yloxy]-2,3-dihydro-benzofuran-3-yl}-acetic acid methyl ester

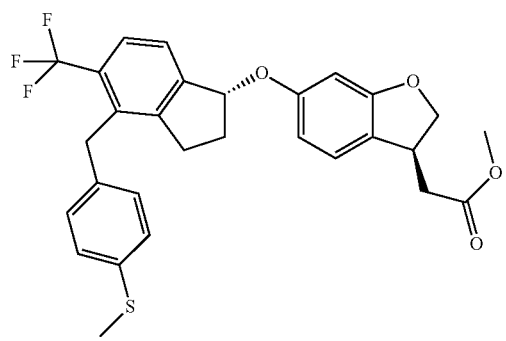 [SMILES: COC(=O)C[C@@H]1COc2cc(O[C@@H]3CCc4c3ccc(C(F)(F)F)c4Cc3ccc(SC)cc3)ccc21]

The title compound is prepared from {(S)-6-[(R)-4-bromo-5-trifluoromethyl-indan-1-yloxy]-2,3-dihydro-benzofuran-3-yl}-acetic acid methyl ester and 4-methylsulfanyl-benzyl bromide following a procedure analogous to that described for Intermediate 7.

Intermediate 18

{(S)-6-[(R)-4-(4-Methylsulfonyl-benzyl)-5-trifluoromethyl-indan-1-yloxy]-2,3-dihydro-benzofuran-3-yl}-acetic acid methyl ester

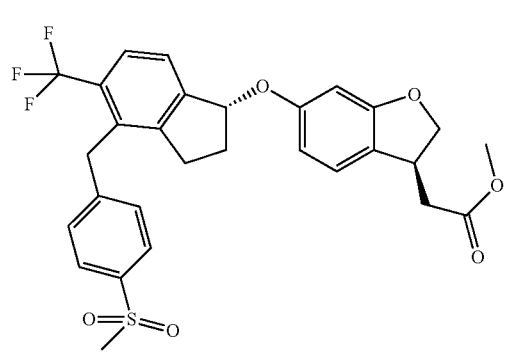 [SMILES: COC(=O)C[C@@H]1COc2cc(O[C@@H]3CCc4c3ccc(C(F)(F)F)c4Cc3ccc(S(C)(=O)=O)cc3)ccc21]

3-Chloro-peroxybenzoic acid (70%, 76 mg) is added to a solution of {(S)-6-[(R)-4-(4-methylsulfanyl-benzyl)-5-trifluoromethyl-indan-1-yloxy]-2,3-dihydro-benzofuran-3-yl}-acetic acid methyl ester (65 mg) in dichloromethane (2 mL) at room temperature. The solution is stirred at room temperature for 3 h and is then concentrated. The residue is taken up in methanol and chromatographed (HPLC, acetonitrile/water) to give the title compound. LC (method 3): $t_R$=0.65 min; Mass spectrum (ESI$^+$): m/z=583 [M+Na]$^+$.

Intermediate 19

{(S)-6-[(R)-4-(3,5-Difluoro-benzyl)-7-fluoro-indan-1-yloxy]-2,3-dihydro-benzofuran-3-yl}-acetic acid methyl ester

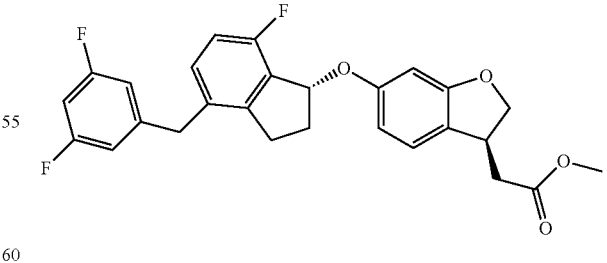

The title compound is prepared from {(S)-6-[(R)-4-bromo-7-fluoro-indan-1-yloxy]-2,3-dihydro-benzofuran-3-yl}-acetic acid methyl ester and 3,5-difluoro-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd- PEPPSI-IPr) is used as catalyst. LC (method 9): $t_R$=0.91 min; Mass spectrum (ESI$^+$): m/z=491 [M+Na]$^+$.

Intermediate 20

{(S)-6-[(R)-4-(2,6-Difluoro-benzyl)-7-fluoro-indan-1-yloxy]-2,3-dihydro-benzofuran-3-yl}-acetic acid methyl ester

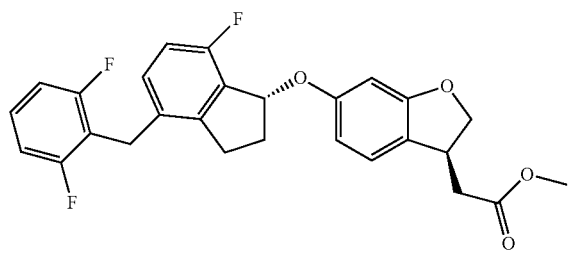 [SMILES: COC(=O)C[C@@H]1COc2cc(O[C@@H]3CCc4c(Cc5c(F)cccc5F)ccc(F)c43)ccc21]

The title compound is prepared from {(S)-6-[(R)-4-bromo-7-fluoro-indan-1-yloxy]-2,3-dihydro-benzofuran-3-yl}-acetic acid methyl ester and 2,6-difluoro-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 9): $t_R$=0.91 min; Mass spectrum (ESI$^+$): m/z=491 [M+Na]$^+$.

Intermediate 21

{(S)-6-[(R)-4-(4-Cyano-benzyl)-7-fluoro-indan-1-yloxy]-2,3-dihydro-benzofuran-3-yl}-acetic acid methyl ester

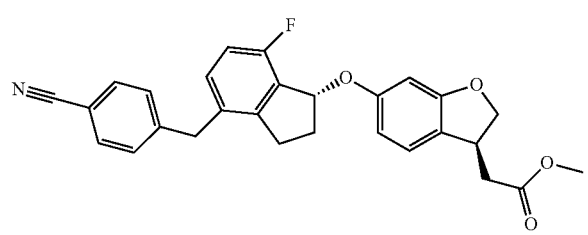 [SMILES: COC(=O)C[C@@H]1COc2cc(O[C@@H]3CCc4c(Cc5ccc(C#N)cc5)ccc(F)c43)ccc21]

The title compound is prepared from {(S)-6-[(R)-4-bromo-7-fluoro-indan-1-yloxy]-2,3-dihydro-benzofuran-3-yl}-acetic acid methyl ester and 4-cyano-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 9): $t_R$=0.74 min; Mass spectrum (ESI$^+$): m/z=458 [M+H]$^+$.

Intermediate 22

{(S)-6-[(R)-4-(2,4-Difluoro-benzyl)-7-fluoro-indan-1-yloxy]-2,3-dihydro-benzofuran-3-yl}-acetic acid methyl ester

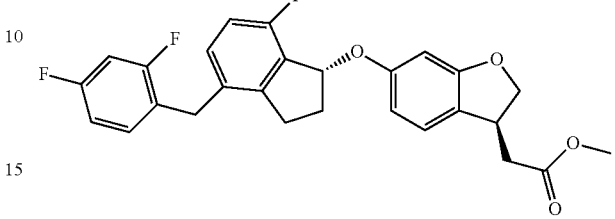

The title compound is prepared from {(S)-6-[(R)-4-bromo-7-fluoro-indan-1-yloxy]-2,3-dihydro-benzofuran-3-yl}-acetic acid methyl ester and 2,4-difluoro-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 9): $t_R$=0.91 min; Mass spectrum (ESI$^+$): m/z=491 [M+Na]$^+$.

Intermediate 23

{(S)-6-[(R)-5-Cyano-4-(2-fluoro-benzyl)-indan-1-yloxy]-2,3-dihydro-benzofuran-3-yl}-acetic acid methyl ester

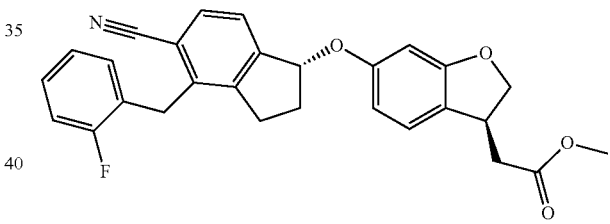

The title compound is prepared from {(S)-6-[(R)-4-bromo-5-cyano-indan-1-yloxy]-2,3-dihydro-benzofuran-3-yl}-acetic acid methyl ester and 2-fluoro-benzyl bromide following a procedure analogous to that described for Intermediate 7. LC (method 6): $t_R$=1.19 min; Mass spectrum (ESI$^+$): m/z=458 [M+H]$^+$.

Intermediate 24

{(S)-6-[(R)-5-Cyano-4-(4-fluoro-benzyl)-indan-1-yloxy]-2,3-dihydro-benzofuran-3-yl}-acetic acid methyl ester

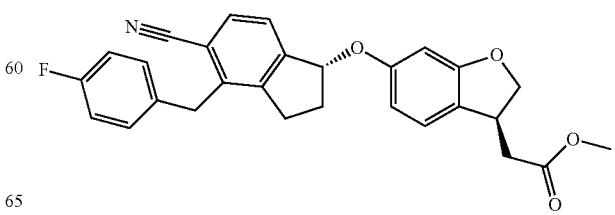

The title compound is prepared from {(S)-6-[(R)-4-bromo-5-cyano-indan-1-yloxy]-2,3-dihydro-benzofuran-3-yl}-acetic acid methyl ester and 4-fluoro-benzyl bromide following a procedure analogous to that described for Intermediate 7. LC (method 6): $t_R$=1.18 min; Mass spectrum (ESI$^+$): m/z=458 [M+H]$^+$.

Intermediate 25

{(S)-6-[(R)-5-Cyano-4-(3-fluoro-benzyl)-indan-1-yloxy]-2,3-dihydro-benzofuran-3-yl}-acetic acid methyl ester

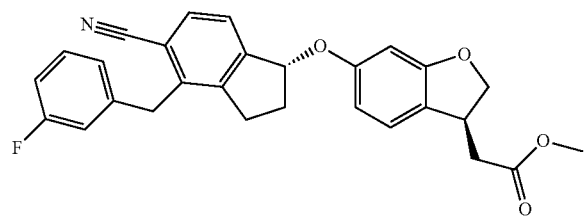 [SMILES: COC(=O)C[C@@H]1COc2cc(O[C@@H]3CCc4c3ccc(C#N)c4Cc3cccc(F)c3)ccc21]

The title compound is prepared from {(S)-6-[(R)-4-bromo-5-cyano-indan-1-yloxy]-2,3-dihydro-benzofuran-3-yl}-acetic acid methyl ester and 3-fluoro-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 4): $t_R$=1.22 min; Mass spectrum (ESI$^+$): m/z=458 [M+H]$^+$.

Intermediate 26

{(S)-6-[(R)-4-(4-Acetoxy-benzyl)-5-trifluoromethyl-indan-1-yloxy]-2,3-dihydro-benzofuran-3-yl}-acetic acid methyl ester

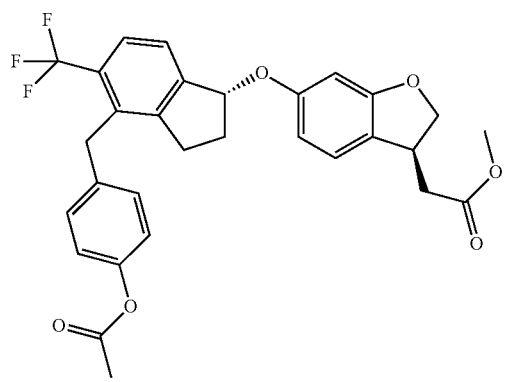 [SMILES: COC(=O)C[C@@H]1COc2cc(O[C@@H]3CCc4c3ccc(C(F)(F)F)c4Cc3ccc(OC(C)=O)cc3)ccc21]

The title compound is prepared from {(S)-6-[(R)-4-bromo-5-trifluoromethyl-indan-1-yloxy]-2,3-dihydro-benzofuran-3-yl}-acetic acid methyl ester and 4-acetoxy-benzyl bromide following a procedure analogous to that described for Intermediate 7. LC (method 8): $t_R$=1.27 min; Mass spectrum (ESI$^+$): m/z=541 [M+H]$^+$.

Intermediate 27

{(S)-6-[(R)-4-(4-Hydroxy-benzyl)-5-trifluoromethyl-indan-1-yloxy]-2,3-dihydro-benzofuran-3-yl}-acetic acid methyl ester

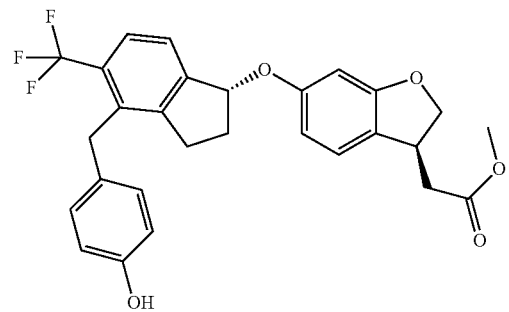 [SMILES: COC(=O)C[C@@H]1COc2cc(O[C@@H]3CCc4c3ccc(C(F)(F)F)c4Cc3ccc(O)cc3)ccc21]

A mixture of {(S)-6-[(R)-4-(4-acetoxy-benzyl)-5-trifluoromethyl-indan-1-yloxy]-2,3-dihydro-benzofuran-3-yl}-acetic acid methyl ester (0.19 g), K$_2$CO$_3$ (0.08 g), and methanol (5 ml) is stirred at room temperature for 2 h. The solution is neutralized with 1 N aqueous HCl solution and concentrated. Water is added to the residue, and the resulting mixture is extracted with ethyl acetate. The combined extract is dried (MgSO$_4$) and concentrated. The residue is chromatographed on silica gel (cyclohexane/ethyl acetate) to give the title compound. LC (method 8): $t_R$=1.22 min; Mass spectrum (ESI$^+$): m/z=521 [M+Na]$^+$.

Intermediate 28

{(S)-6-[(R)-4-(2,4-Difluoro-benzyl)-5-trifluoromethyl-indan-1-yloxy]-2,3-dihydro-benzofuran-3-yl}-acetic acid methyl ester

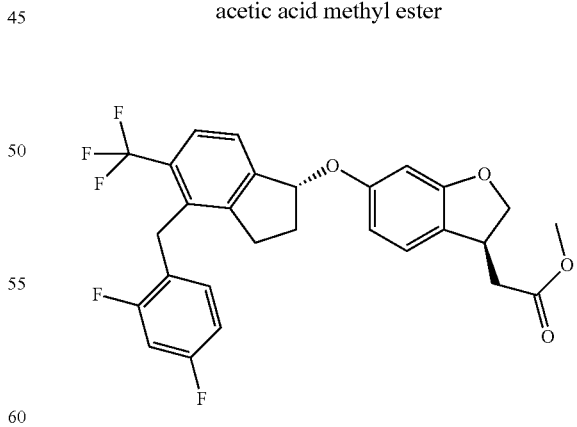

The title compound is prepared from {(S)-6-[(R)-4-bromo-5-trifluoromethyl-indan-1-yloxy]-2,3-dihydro-benzofuran-3-yl}-acetic acid methyl ester and 2,4-difluoro-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 3): $t_R$=0.98 min; Mass spectrum (ESI$^+$): m/z=541 [M+Na]$^+$.

Intermediate 29

{(S)-6-[(R)-4-(3-Methoxy-benzyl)-5-trifluoromethyl-indan-1-yloxy]-2,3-dihydro-benzofuran-3-yl}-acetic acid methyl ester

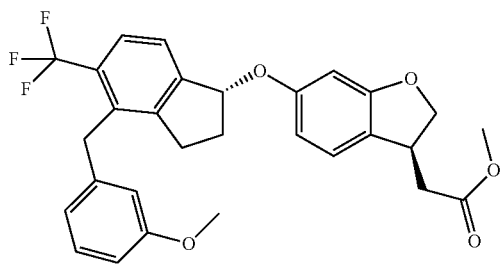

The title compound is prepared from {(S)-6-[(R)-4-bromo-5-trifluoromethyl-indan-1-yloxy]-2,3-dihydro-benzofuran-3-yl}-acetic acid methyl ester and 3-methoxy-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 8): $t_R$=1.30 min; Mass spectrum (ESI$^+$): m/z=535 [M+Na]$^+$.

Intermediate 30

{(S)-6-[(R)-5-Cyano-4-(2,6-difluoro-benzyl)-indan-1-yloxy]-2,3-dihydro-benzofuran-3-yl}-acetic acid methyl ester

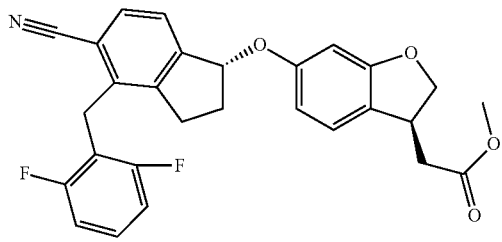 [SMILES: COC(=O)C[C@@H]1COc2cc(O[C@@H]3CCc4c3ccc(C#N)c4Cc3c(F)cccc3F)ccc21]

The title compound is prepared from {(S)-6-[(R)-4-bromo-5-cyano-indan-1-yloxy]-2,3-dihydro-benzofuran-3-yl}-acetic acid methyl ester and 2,6-difluoro-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 4): $t_R$=1.22 min; Mass spectrum (ESI$^+$): m/z=476 [M+H]$^+$.

Intermediate 31

{(S)-6-[(R)-4-(3-Fluoro-benzyl)-5-trifluoromethyl-indan-1-yloxy]-2,3-dihydro-benzofuran-3-yl}-acetic acid methyl ester

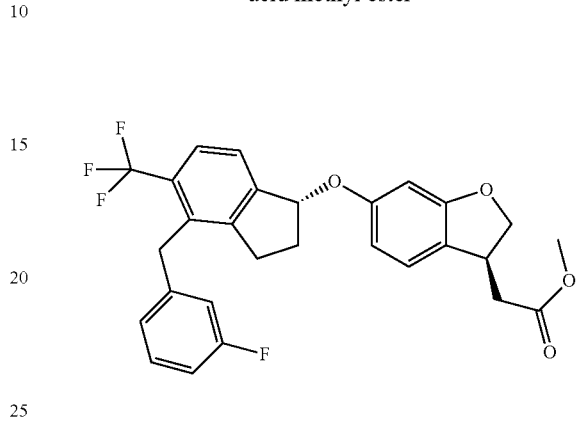

The title compound is prepared from {(S)-6-[(R)-4-bromo-5-trifluoromethyl-indan-1-yloxy]-2,3-dihydro-benzofuran-3-yl}-acetic acid methyl ester and 3-fluoro-benzylzinc chloride following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 7): $t_R$=0.98 min; Mass spectrum (ESI$^+$): m/z=523 [M+Na]$^+$.

Intermediate 32

{(S)-6-[(R)-4-(4-Fluoro-benzyl)-5-trifluoromethyl-indan-1-yloxy]-2,3-dihydro-benzofuran-3-yl}-acetic acid methyl ester

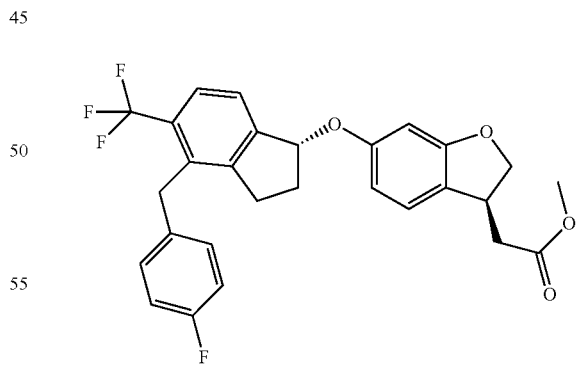

The title compound is prepared from {(S)-6-[(R)-4-bromo-5-trifluoromethyl-indan-1-yloxy]-2,3-dihydro-benzofuran-3-yl}-acetic acid methyl ester and 4-fluoro-benzylzinc chloride following a procedure analogous to that described in Step 6 of Intermediate 1; [1,3-bis(2,6-diisopropylphenyl)imidazol-2-ylidene]-(3-chloropyridyl)-palladium(II) dichloride

Intermediate 33

{(S)-6-[(R)-4-(2-Fluoro-benzyl)-5-trifluoromethyl-indan-1-yloxy]-2,3-dihydro-benzofuran-3-yl}-acetic acid methyl ester

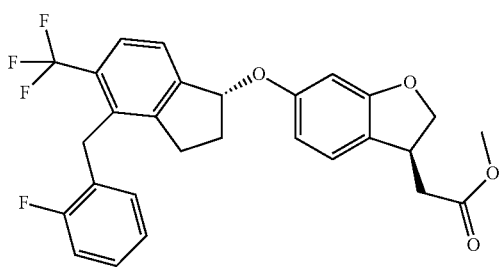 [SMILES: COC(=O)C[C@@H]1COc2cc(O[C@@H]3CCc4c3ccc(C(F)(F)F)c4Cc3ccccc3F)ccc21]

The title compound is prepared from {(S)-6-[(R)-4-bromo-5-trifluoromethyl-indan-1-yloxy]-2,3-dihydro-benzofuran-3-yl}-acetic acid methyl ester and 2-fluoro-benzylzinc chloride following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 6): $t_R$=1.29 min; Mass spectrum (ESI$^+$): m/z=501 [M+H]$^+$.

Intermediate 34

{(S)-6-[(R)-5-Cyano-4-(2,3-difluoro-benzyl)-indan-1-yloxy]-2,3-dihydro-benzofuran-3-yl}-acetic acid methyl ester

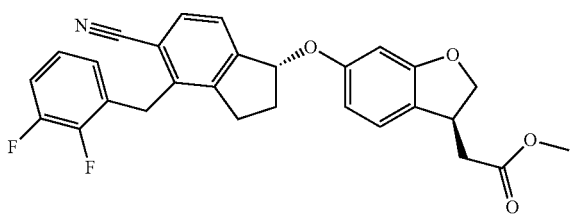 [SMILES: COC(=O)C[C@@H]1COc2cc(O[C@@H]3CCc4c3ccc(C#N)c4Cc3cccc(F)c3F)ccc21]

The title compound is prepared from {(S)-6-[(R)-4-bromo-5-cyano-indan-1-yloxy]-2,3-dihydro-benzofuran-3-yl}-acetic acid methyl ester and 2,3-difluoro-benzyl bromide following a procedure analogous to that described for Intermediate 7. LC (method 4): $t_R$=1.25 min; Mass spectrum (ESI$^+$): m/z=476 [M+H]$^+$.

Intermediate 35

{(S)-6-[(R)-4-(4-Methoxy-benzyl)-5-trifluoromethyl-indan-1-yloxy]-2,3-dihydro-benzofuran-3-yl}-acetic acid methyl ester

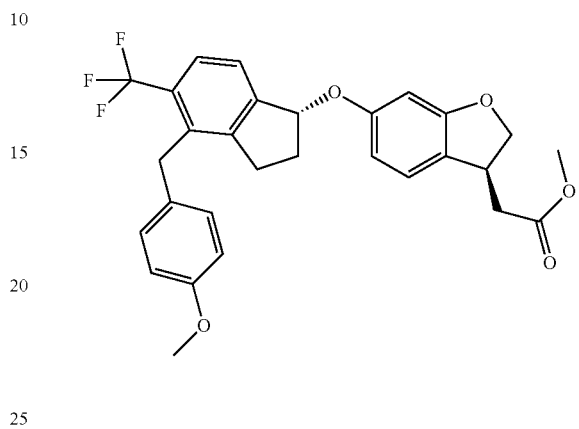

Iodomethane (8 μL) is added to a mixture of {(S)-6-[(R)-4-(4-hydroxy-benzyl)-5-trifluoromethyl-indan-1-yloxy]-2,3-dihydro-benzofuran-3-yl}-acetic acid methyl ester (30 mg), $K_2CO_3$ (15 mg), and N,N-dimethylformamide (1 mL) at room temperature. The mixture is stirred at room temperature overnight. The mixture is filtered and then chromatographed (HPLC; acetonitrile/water) to give the title compound. LC (method 6): $t_R$=1.26 min; Mass spectrum (ESI$^+$): m/z=535 [M+Na]$^+$.

Intermediate 36

{(S)-6-[(R)-4-(3-Cyano-benzyl)-5-trifluoromethyl-indan-1-yloxy]-2,3-dihydro-benzofuran-3-yl}-acetic acid methyl ester

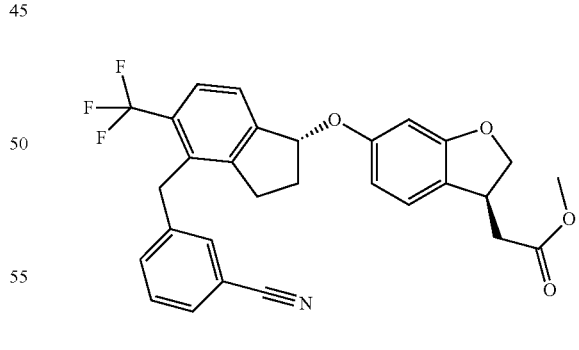

The title compound is prepared from {(S)-6-[(R)-4-bromo-5-trifluoromethyl-indan-1-yloxy]-2,3-dihydro-benzofuran-3-yl}-acetic acid methyl ester and 3-cyano-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 6): $t_R$=1.23 min; Mass spectrum (ESI$^+$): m/z=508 [M+H]$^+$.

Intermediate 37

{(S)-6-[(R)-4-(2-Methyl-benzyl)-5-trifluoromethyl-indan-1-yloxy]-2,3-dihydro-benzofuran-3-yl}-acetic acid methyl ester

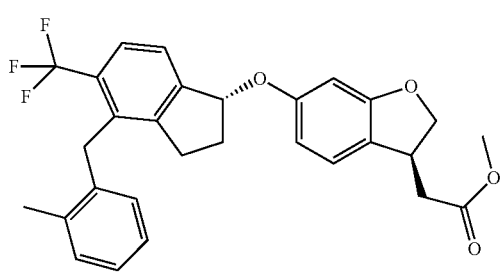 [SMILES: COC(=O)C[C@@H]1COc2cc(O[C@@H]3CCc4c3ccc(C(F)(F)F)c4Cc3ccccc3C)ccc21]

The title compound is prepared from {(S)-6-[(R)-4-bromo-5-trifluoromethyl-indan-1-yloxy]-2,3-dihydro-benzofuran-3-yl}-acetic acid methyl ester and 2-methyl-benzylzinc chloride following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 6): $t_R$=1.29 min; Mass spectrum (ESI$^+$): m/z=497 [M+H]$^+$.

Intermediate 38

{(S)-6-[(R)-4-(2-Cyano-benzyl)-5-trifluoromethyl-indan-1-yloxy]-2,3-dihydro-benzofuran-3-yl}-acetic acid methyl ester

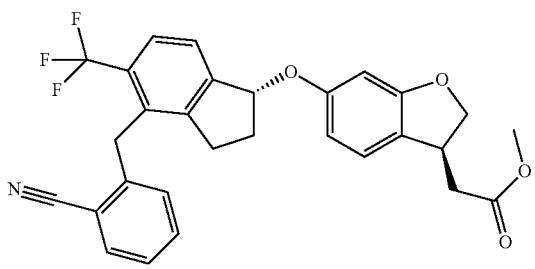 [SMILES: COC(=O)C[C@@H]1COc2cc(O[C@@H]3CCc4c3ccc(C(F)(F)F)c4Cc3ccccc3C#N)ccc21]

The title compound is prepared from {(S)-6-[(R)-4-bromo-5-trifluoromethyl-indan-1-yloxy]-2,3-dihydro-benzofuran-3-yl}-acetic acid methyl ester and 2-cyano-benzylzinc bromide following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 6): $t_R$=1.23 min; Mass spectrum (ESI$^+$): m/z=508 [M+H]$^+$.

Intermediate 39

{(S)-6-[(R)-4-(4-Chloro-benzyl)-5-trifluoromethyl-indan-1-yloxy]-2,3-dihydro-benzofuran-3-yl}-acetic acid methyl ester

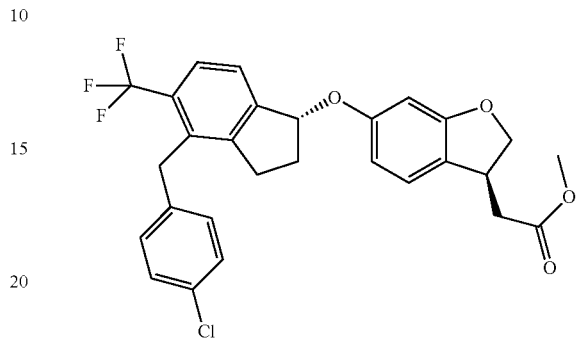

The title compound is prepared from {(S)-6-[(R)-4-bromo-5-trifluoromethyl-indan-1-yloxy]-2,3-dihydro-benzofuran-3-yl}-acetic acid methyl ester and 4-chloro-benzylzinc chloride following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 3): $t_R$=1.01 min.

Intermediate 40

{(S)-6-[(R)-5-Trifluoromethyl-4-vinyl-indan-1-yloxy]-2,3-dihydro-benzofuran-3-yl}-acetic acid methyl ester

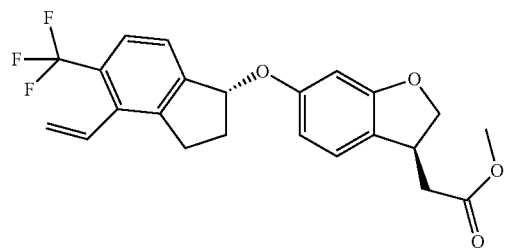 [SMILES: C=Cc1c(C(F)(F)F)ccc2c1CC[C@H]2Oc1ccc2c(c1)OC[C@H]2CC(=O)OC]

A flask charged with a stir bar, {(S)-6-[(R)-4-bromo-5-trifluoromethyl-indan-1-yloxy]-2,3-dihydro-benzofuran-3-yl}-acetic acid methyl ester (1.00 g), vinylboronic acid pinacol ester (0.39 g), K$_3$PO$_4$ (1.80 g), toluene (8 mL) and water (0.8 mL) is purged with Ar for 10 min. Palladium(II) acetate (24 mg) and dicyclohexyl-(2',6'-dimethoxybiphenyl-2-yl)-phosphine (S-Phos, 87 mg) are added, the flask is sealed, and the mixture is heated to 100° C. The mixture is stirred at this temperature overnight. After cooling to room temperature, water is added and the mixture is extracted with ethyl acetate. The combined extract is washed with brine, dried (charcoal/Na$_2$SO$_4$), and concentrated. The crude product is submitted to the next reaction step without further purification. LC (method 2): $t_R$=1.26 min; Mass spectrum (ESI$^+$): m/z=457 [M+Na]$^+$.

Intermediate 41

{(S)-6-[(R)-4-Formyl-5-trifluoromethyl-indan-1-yloxy]-2,3-dihydro-benzofuran-3-yl}-acetic acid methyl ester

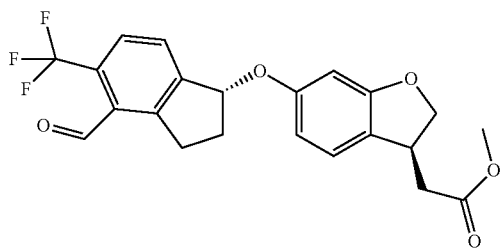 [SMILES: COC(=O)C[C@@H]1COc2cc(O[C@@H]3CCc4c3ccc(C(F)(F)F)c4C=O)ccc21]

NaIO$_4$ (1.80 g) and OsO$_4$ (4% in water, 50 μL) are added to a mixture of {(S)-6-[(R)-5-trifluoromethyl-4-vinyl-indan-1-yloxy]-2,3-dihydro-benzofuran-3-yl}-acetic acid methyl ester (1.25 g), tetrahydrofuran (16 mL), and water (4 mL) at room temperature. The mixture is stirred at 50° C. overnight. After cooling to room temperature, water is added and the mixture is extracted with ethyl acetate. The combined extract is washed with brine, dried (Na$_2$SO$_4$), and concentrated. The residue is chromatographed on silica gel (cyclohexane/ethyl acetate) to give the title compound. LC (method 2): $t_R$=1.19 min; Mass spectrum (ESI$^+$): m/z=421 [M+H]$^+$.

Intermediate 42

{(S)-6-[(R)-4-Hydroxymethyl-5-trifluoromethyl-indan-1-yloxy]-2,3-dihydro-benzofuran-3-yl}-acetic acid methyl ester

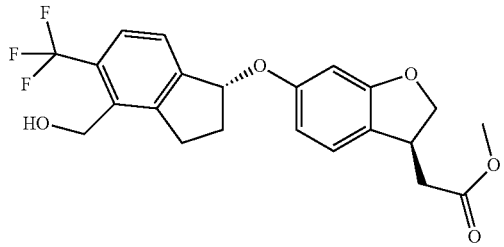 [SMILES: COC(=O)C[C@@H]1COc2cc(O[C@@H]3CCc4c3ccc(C(F)(F)F)c4CO)ccc21]

NaBH$_4$ (18 mg) is added to a solution of {(S)-6-[(R)-4-formyl-5-trifluoromethyl-indan-1-yloxy]-2,3-dihydro-benzofuran-3-yl}-acetic acid methyl ester (0.20 g) in tetrahydrofuran (4 mL) and water (1 mL) at room temperature. The mixture is stirred at room temperature for 30 min. 1 N aqueous HCl solution is added and the mixture is extracted with ethyl acetate. The combined extract is washed with brine, dried (Na$_2$SO$_4$), and concentrated to give the title compound. The crude product is submitted to the next reaction step without further purification. LC (method 2): $t_R$=1.19 min; Mass spectrum (ESI$^+$): m/z=421 [M+H]$^+$.

Intermediate 43

{(S)-6-[(R)-4-Bromomethyl-5-trifluoromethyl-indan-1-yloxy]-2,3-dihydro-benzofuran-3-yl}-acetic acid methyl ester

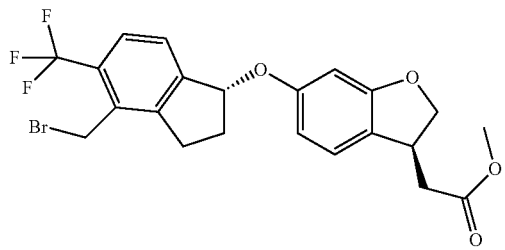 [SMILES: COC(=O)C[C@@H]1COc2cc(O[C@@H]3CCc4c3ccc(C(F)(F)F)c4CBr)ccc21]

Methylsulfonyl bromide (0.96 mL) is added to a solution of {(S)-6-[(R)-4-hydroxymethyl-5-trifluoromethyl-indan-1-yloxy]-2,3-dihydro-benzofuran-3-yl}-acetic acid methyl ester (2.00 g) and triethylamine (1.98 mL) in dichloromethane (20 mL) chilled in an ice bath. The cooling bath is removed, and the solution is stirred at room temperature overnight. More dichloromethane is added, and the resulting solution is washed with aqueous NaHCO$_3$ solution and brine, dried (Na$_2$SO$_4$), and concentrated. The residue is chromatographed on silica gel (cyclohexane/ethyl acetate) to give the title compound. LC (method 2): $t_R$=1.24 min.

Intermediate 44

{(S)-6-[(R)-4-(2-Methoxy-pyridin-5-yl)-5-trifluoromethyl-indan-1-yloxy]-2,3-dihydro-benzofuran-3-yl}-acetic acid methyl ester

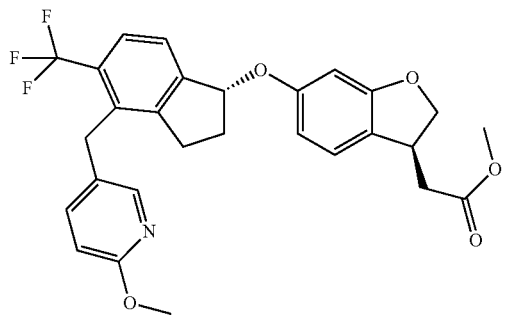 [SMILES: COC(=O)C[C@@H]1COc2cc(O[C@@H]3CCc4c3ccc(C(F)(F)F)c4Cc3ccc(OC)nc3)ccc21]

A flask charged with a stir bar, 2 M aqueous Na$_2$CO$_3$ solution (0.13 mL), {(S)-6-[(R)-4-bromomethyl-5-trifluoromethyl-indan-1-yloxy]-2,3-dihydro-benzofuran-3-yl}-acetic acid methyl ester (50 mg), 2-methoxy-pyridine-5-boronic acid (16 mg), and N,N-dimethylformamide (1 mL) is purged with Ar for 5 min. [1,1'-Bis(diphenylphosphino)-ferrocene]-dichloropalladium(II)*CH$_2$Cl$_2$ complex (5 mg) is added and the mixture is heated to 65° C. The mixture is stirred at 65° C. overnight and then cooled to room temperature. Water is added and the resulting mixture is extracted with ethyl acetate. The combined extract is washed with brine, dried (MgSO$_4$), and concentrated. The residue is chromatographed (HPLC; acetonitrile/water/ammonia) to give the title compound. LC (method 2): $t_R$=1.23 min; Mass spectrum (ES$^+$): m/z=514 [M+H]$^+$.

Intermediate 45

{(S)-6-[(R)-4-(2-Fluoro-pyridin-5-yl)-5-trifluoromethyl-indan-1-yloxy]-2,3-dihydro-benzofuran-3-yl}-acetic acid methyl ester

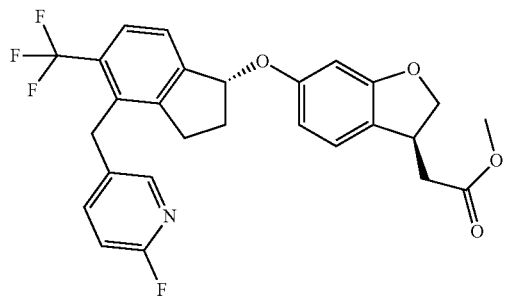 [SMILES: COC(=O)C[C@@H]1COc2cc(O[C@@H]3CCc4c3ccc(C(F)(F)F)c4Cc3ccc(F)nc3)ccc21]

A flask charged with a stir bar, 2 M aqueous Na$_2$CO$_3$ solution (85 µL), {(S)-6-[(R)-4-bromomethyl-5-trifluoromethyl-indan-1-yloxy]-2,3-dihydro-benzofuran-3-yl}-acetic acid methyl ester (40 mg), 2-fluoro-pyridine-5-boronic acid (12 mg), ethanol (0.25 mL), and toluene (1 mL) is purged with Ar for 5 min. Tetrakis(triphenylphosphine)-palladium(0) (5 mg) is added and the mixture is heated to 80° C. The mixture is stirred at 80° C. overnight and then cooled to room temperature. Water is added and the resulting mixture is extracted with ethyl acetate. The combined extract is washed with brine, dried (MgSO$_4$), and concentrated. The residue is chromatographed on silica gel (cyclohexane/ethyl acetate) to give the title compound. LC (method 2): $t_R$=1.00 min; Mass spectrum (ESI$^+$): m/z=502 [M+H]$^+$.

Intermediate 46

{(S)-6-[(R)-4-(2,5-Dimethoxy-benzyl)-5-trifluoromethyl-indan-1-yloxy]-2,3-dihydro-benzofuran-3-yl}-acetic acid methyl ester

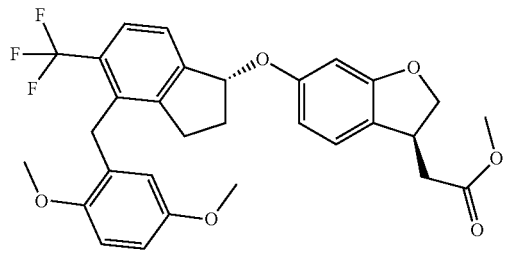 [SMILES: COC(=O)C[C@@H]1COc2cc(O[C@@H]3CCc4c3ccc(C(F)(F)F)c4Cc3cc(OC)ccc3OC)ccc21]

The title compound is prepared from {(S)-6-[(R)-4-bromo-5-trifluoromethyl-indan-1-yloxy]-2,3-dihydro-benzofuran-3-yl}-acetic acid methyl ester and 2,5-dimethoxy-benzylzinc chloride following a procedure analogous to that described in Step 6 of Intermediate 1; [1,3-bis(2,6-diisopropylphenyl)imidazol-2-ylidene]-(3-chloropyridyl)-palladium(II) dichloride (Pd-PEPPSI-IPr) is used as catalyst. LC (method 3): $t_R$=0.94 min; Mass spectrum (ESI$^+$): m/z=565 [M+Na]$^+$.

Example 1

{(S)-6-[(R)-4-Benzyl-5-cyano-indan-1-yloxy]-2,3-dihydro-benzofuran-3-yl}-acetic acid

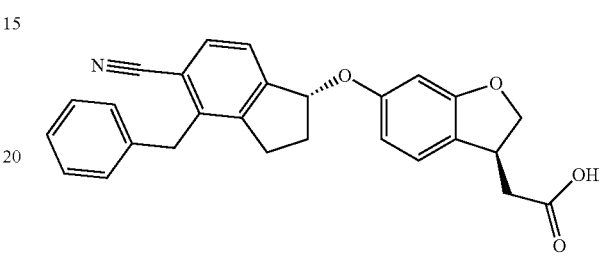

1 M aqueous NaOH solution (0.60 mL) is added to a solution of {(S)-6-[(R)-4-benzyl-5-cyano-indan-1-yloxy]-2,3-dihydro-benzofuran-3-yl}-acetic acid methyl ester (0.10 g) in methanol (3 mL) at room temperature. The mixture is stirred at 40° C. for 1 h. The mixture is diluted with water and neutralized with 1 M aqueous HCl solution. The resulting mixture is extracted with ethyl acetate, and the combined extract is washed with brine and dried (MgSO$_4$). The solvent is evaporated and the residue is chromatographed on silica gel (cyclohexane/ethyl acetate 50:50→0:100) to give the title compound. In case the product is insufficiently pure after this procedure the product is submitted to HPLC on reversed phase (MeCN/water). LC (method 4): $t_R$=1.14 min; Mass spectrum (ESI$^+$): m/z=424 [M+H]$^+$.

Example 2

{(S)-6-[(R)-4-(6-Chloro-pyridin-3-ylmethyl)-5-cyano-indan-1-yloxy]-2,3-dihydro-benzofuran-3-yl}-acetic acid

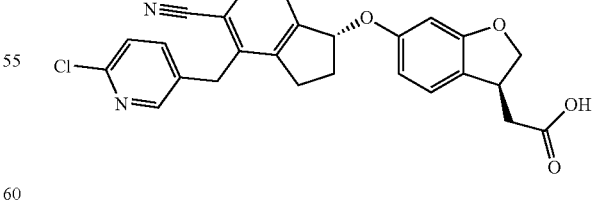

The title compound is prepared from {(S)-6-[(R)-4-(6-chloro-pyridin-3-ylmethyl)-5-cyano-indan-1-yloxy]-2,3-dihydro-benzofuran-3-yl}-acetic acid methyl ester following a procedure analogous to that described for Example 1. LC (method 4): $t_R$=1.07 min; Mass spectrum (ESI$^+$): m/z=461/463 (Cl) [M+H]$^+$.

Example 3

{(S)-6-[(R)-5-Cyano-4-(3-methoxy-benzyl)-indan-1-yloxy]-2,3-dihydro-benzofuran-3-yl}-acetic acid

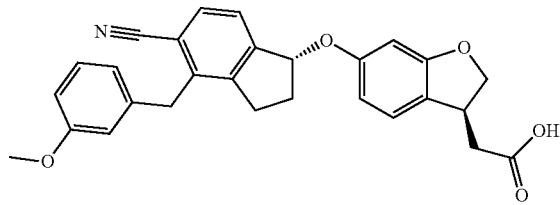 [SMILES: COc1cccc(Cc2c(C#N)ccc3c2CC[C@H]3Oc2ccc3c(c2)OC[C@H]3CC(=O)O)c1]

The title compound is prepared from {(S)-6-[(R)-5-cyano-4-(3-methoxy-benzyl)-indan-1-yloxy]-2,3-dihydro-benzofuran-3-yl}-acetic acid methyl ester following a procedure analogous to that described for Example 1. LC (method 4): $t_R$=1.12 min; Mass spectrum (ESI+): m/z=456 [M+H]+.

Example 4

{(S)-6-[(R)-5-Cyano-4-(4-methoxy-benzyl)-indan-1-yloxy]-2,3-dihydro-benzofuran-3-yl}-acetic acid

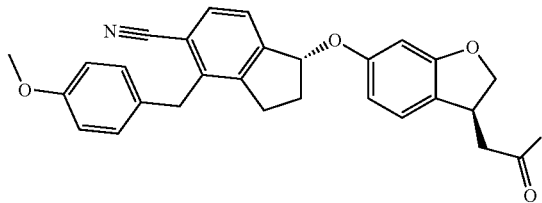

The title compound is prepared from {(S)-6-[(R)-5-cyano-4-(4-methoxy-benzyl)-indan-1-yloxy]-2,3-dihydro-benzofuran-3-yl}-acetic acid methyl ester following a procedure analogous to that described for Example 1. LC (method 4): $t_R$=1.12 min; Mass spectrum (ESI+): m/z=456 [M+H]+.

Example 5

{(S)-6-[(R)-5-Cyano-4-(2,6-dimethyl-benzyl)-indan-1-yloxy]-2,3-dihydro-benzofuran-3-yl}-acetic acid

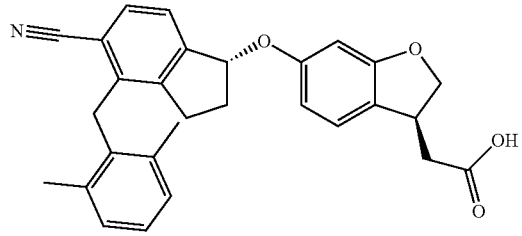 [SMILES: Cc1cccc(C)c1Cc1c(C#N)ccc2c1CC[C@H]2Oc1ccc2c(c1)OC[C@H]2CC(=O)O]

The title compound is prepared from {(S)-6-[(R)-5-cyano-4-(2,6-dimethyl-benzyl)-indan-1-yloxy]-2,3-dihydro-benzofuran-3-yl}-acetic acid methyl ester following a procedure analogous to that described for Example 1. LC (method 4): $t_R$=1.20 min; Mass spectrum (ESI-): m/z=452 [M-H]-.

Example 6

{(S)-6-[(R)-5-Cyano-4-(2-methyl-benzyl)-indan-1-yloxy]-2,3-dihydro-benzofuran-3-yl}-acetic acid

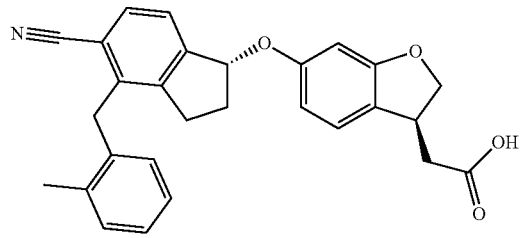 [SMILES: Cc1ccccc1Cc1c(C#N)ccc2c1CC[C@H]2Oc1ccc2c(c1)OC[C@H]2CC(=O)O]

The title compound is prepared from {(S)-6-[(R)-5-cyano-4-(2-methyl-benzyl)-indan-1-yloxy]-2,3-dihydro-benzofuran-3-yl}-acetic acid methyl ester following a procedure analogous to that described for Example 1. LC (method 4): $t_R$=1.16 min; Mass spectrum (ESI-): m/z=438 [M-H]-.

Example 7

{(S)-6-[(R)-5-Cyano-4-(4-methylsulfanyl-benzyl)-indan-1-yloxy]-2,3-dihydro-benzofuran-3-yl}-acetic acid

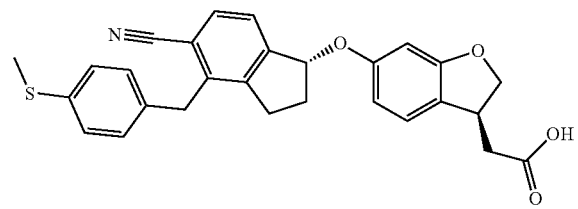 [SMILES: CSc1ccc(Cc2c(C#N)ccc3c2CC[C@H]3Oc2ccc3c(c2)OC[C@H]3CC(=O)O)cc1]

The title compound is prepared from {(S)-6-[(R)-5-cyano-4-(4-methylsulfanyl-benzyl)-indan-1-yloxy]-2,3-dihydro-benzofuran-3-yl}-acetic acid methyl ester following a procedure analogous to that described for Example 1. LC (method 4): $t_R$=1.02 min; Mass spectrum (ESI-): m/z=470 [M-H]-.

Example 8

{(S)-6-[(R)-5-Cyano-4-(4-methylsulfonyl-benzyl)-indan-1-yloxy]-2,3-dihydro-benzofuran-3-yl}-acetic acid

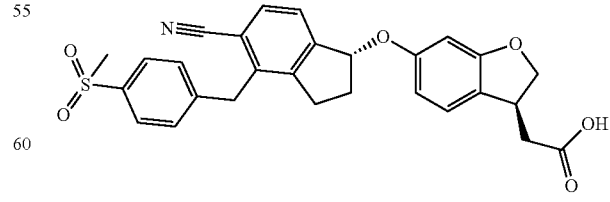

3-Chloroperoxybenzoic acid (26 mg) is added to a solution of {(S)-6-[(R)-5-cyano-4-(4-methylsulfanyl-benzyl)-indan-1-yloxy]-2,3-dihydro-benzofuran-3-yl}-acetic acid (20 mg) in dichloromethane (1 mL) at room temperature. The mixture is stirred at room temperature for 3 h and then concentrated. The residue is purified by HPLC on reversed phase (MeCN/water) to give the title compound. LC (method 4): $t_R$=1.01 min; Mass spectrum (ESI$^-$): m/z=502 [M−H]$^-$.

Example 9

{(S)-6-[(R)-5-Cyano-4-(3-cyano-benzyl)-indan-1-yloxy]-2,3-dihydro-benzofuran-3-yl}-acetic acid

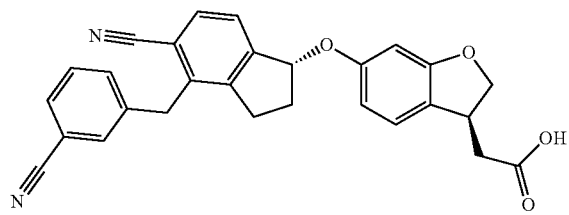 [SMILES: N#Cc1cccc(Cc2c(C#N)ccc3c2CC[C@H]3Oc2ccc3c(c2)OC[C@H]3CC(=O)O)c1]

The title compound is prepared from {(S)-6-[(R)-5-cyano-4-(3-cyano-benzyl)-indan-1-yloxy]-2,3-dihydro-benzofuran-3-yl}-acetic acid methyl ester following a procedure analogous to that described for Example 1. LC (method 4): $t_R$=1.08 min; Mass spectrum (ESI$^-$): m/z=449 [M−H]$^-$.

Example 10

{(S)-6-[(R)-4-Benzyl-5-trifluoromethyl-indan-1-yloxy]-2,3-dihydro-benzofuran-3-yl}-acetic acid

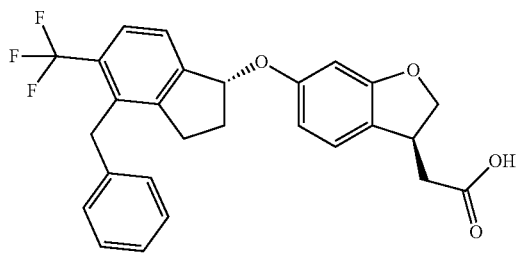 [SMILES: O=C(O)C[C@@H]1COc2cc(O[C@@H]3CCc4c3ccc(C(F)(F)F)c4Cc3ccccc3)ccc21]

The title compound is prepared from {(S)-6-[(R)-4-benzyl-5-trifluoromethyl-indan-1-yloxy]-2,3-dihydro-benzofuran-3-yl}-acetic acid methyl ester following a procedure analogous to that described for Example 1. LC (method 3): $t_R$=0.75 min; Mass spectrum (ESI$^-$): m/z=467 [M−H]$^-$.

Example 11

{(S)-6-[(R)-5-Cyano-4-(4-hydroxy-benzyl)-indan-1-yloxy]-2,3-dihydro-benzofuran-3-yl}-acetic acid

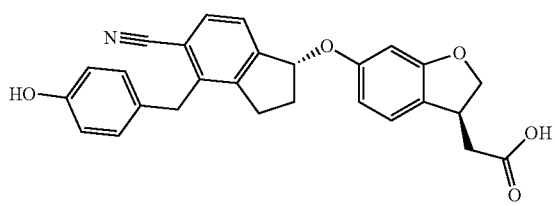 [SMILES: N#Cc1ccc2c(c1Cc1ccc(O)cc1)CC[C@H]2Oc1ccc2c(c1)OC[C@H]2CC(=O)O]

The title compound is prepared from {(S)-6-[(R)-4-(4-acetoxy-benzyl)-5-cyano-indan-1-yloxy]-2,3-dihydro-benzofuran-3-yl}-acetic acid methyl ester following a procedure analogous to that described for Example 1. LC (method 4): $t_R$=1.16 min; Mass spectrum (ESI$^-$): m/z=440 [M−H]$^-$.

Example 12

{(S)-6-[(R)-5-Cyano-4-(4-methylsulfinyl-benzyl)-indan-1-yloxy]-2,3-dihydro-benzofuran-3-yl}-acetic acid

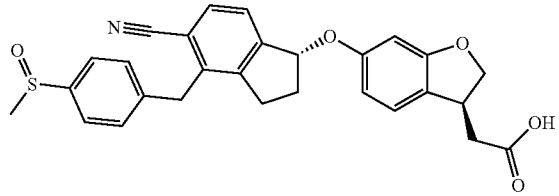 [SMILES: CS(=O)c1ccc(Cc2c(C#N)ccc3c2CC[C@H]3Oc2ccc3c(c2)OC[C@H]3CC(=O)O)cc1]

Aqueous hydrogen peroxide (35%, 5 μL) is added to a solution of {(S)-6-[(R)-5-cyano-4-(4-methylsulfanyl-benzyl)-indan-1-yloxy]-2,3-dihydro-benzofuran-3-yl}-acetic acid (120 mg) in 1,1,1,3,3,3-hexafluoro-2-propanol (1.5 mL) at room temperature. The mixture is stirred at room temperature for 2 h and then diluted with ethyl acetate. The resulting mixture is washed with aqueous $Na_2S_2O_3$ solution, 1 M aqueous HCl solution, and brine, and dried ($Na_2SO_4$). The solvent is evaporated to give the title compound. LC (method 4): $t_R$=0.98 min; Mass spectrum (ESI$^+$): m/z=488 [M+H]$^+$.

Example 13

{(S)-6-[(R)-7-Fluoro-4-(4-methoxybenzyl)-indan-1-yloxy]-2,3-dihydrobenzofuran-3-yl}acetic acid

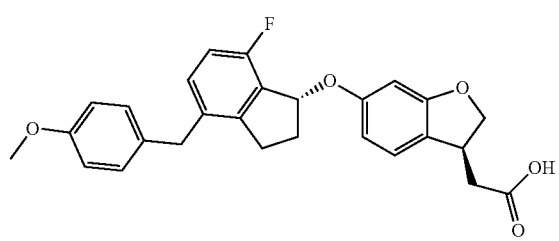 [SMILES: COc1ccc(Cc2ccc(F)c3c2CC[C@H]3Oc2ccc3c(c2)OC[C@H]3CC(=O)O)cc1]

{(S)-6-[(R)-7-Fluoro-4-(4-methoxybenzyl)-indan-1-yloxy]-2,3-dihydrobenzofuran-3-yl}acetic acid methyl ester (40.9 mg) is dissolved in tetrahydrofuran (4 mL) and 1N aqueous sodium hydroxide solution (0.4 mL) is added. The mixture is stirred at room temperature overnight and then acidified with aqueous 1 N hydrochloric acid (0.4 mL). The solution is submitted to HPLC on reversed phase (MeCN/water) to give the title compound. LC (method 6): $t_R$=0.71 min; Mass spectrum (ESI$^-$): m/z=447 [M−H]$^-$.

Example 14

{(S)-6-[(R)-7-Fluoro-4-(3-methoxybenzyl)-indan-1-yloxy]-2,3-dihydrobenzofuran-3-yl}-acetic acid

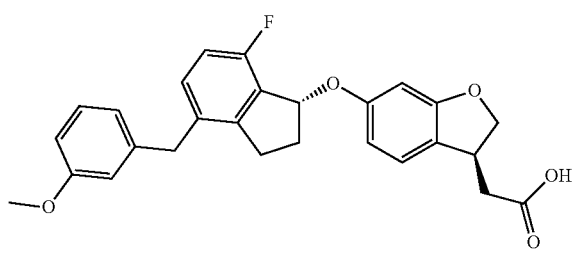 [SMILES: COc1cccc(Cc2ccc(F)c3c2CC[C@H]3Oc2ccc3c(c2)OC[C@H]3CC(=O)O)c1]

{(S)-6-[(R)-7-Fluoro-4-(3-methoxybenzyl)-indan-1-yloxy]-2,3-dihydrobenzofuran-3-yl}-acetic acid methyl ester (30 mg) is dissolved in tetrahydrofuran (4 mL) and 1 N aqueous sodium hydroxide solution (0.4 mL) is added. The mixture is stirred at room temperature overnight and then acidified with 1 N aqueous hydrochloric acid (0.4 mL). The solution is submitted to HPLC on reversed phase (MeCN/water) to give the title compound. LC (method 6): $t_R$=0.71 min; Mass spectrum (ESI$^-$): m/z=447 [M−H]$^-$.

Example 15

{(S)-6-[(R)-(6-Chloro-pyridin-3-ylmethyl)-7-fluoro-indan-1-yloxy]-2,3-dihydro-benzofuran-3-yl}-acetic acid

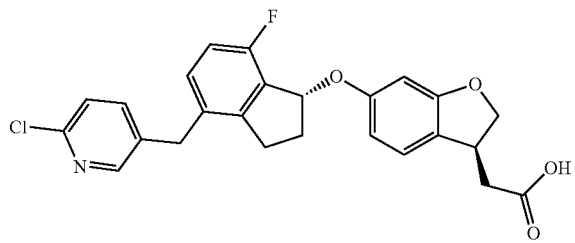 [SMILES: O=C(O)C[C@@H]1COc2cc(O[C@@H]3CCc4c(Cc5ccc(Cl)nc5)ccc(F)c43)ccc21]

{(S)-6-[(R)-(6-Chloro-pyridin-3-ylmethyl)-7-fluoro-indan-1-yloxy]-2,3-dihydro-benzo-furan-3-yl}-acetic acid methyl ester (18.6 mg) is dissolved in tetrahydrofuran (4 mL) and 1N aqueous sodium hydroxide solution (0.4 mL) is added. The mixture is stirred at room temperature overnight and then acidified with 1N aqueous hydrochloric acid (0.4 mL). The solution is submitted to HPLC on reversed phase (MeCN/water) to give the title compound. LC (method 6): $t_R$=0.66 min; Mass spectrum (ESI$^-$): m/z=452/454 (Cl) [M−H]$^-$.

Example 16

{(S)-6-[(R)-4-Benzyl-7-fluoro-indan-1-yloxy]-2,3-dihydrobenzofuran-3-yl}-acetic acid

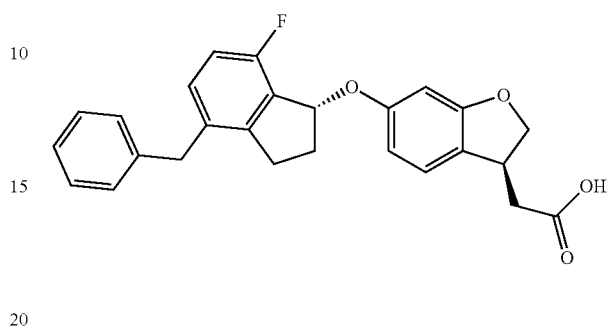

{(S)-6-[(R)-4-Benzyl-7-fluoro-indan-1-yloxy]-2,3-dihydrobenzofuran-3-yl}-acetic acid methyl ester (18.6 mg) is dissolved in tetrahydrofuran (4 mL) and 1N aqueous sodium hydroxide solution (0.4 mL) is added. The mixture is stirred at room temperature overnight and then acidified with 1N aqueous hydrochloric acid (0.4 mL). The solution is submitted to HPLC on reversed phase (MeCN/water) to give the title compound. LC (method 6): $t_R$=0.72 min; Mass spectrum (ESI$^-$): m/z=417 [M−H]$^-$.

Example 17

{(S)-6-[(R)-4-(4-Methylsulfonyl-benzyl)-5-trifluoromethyl-indan-1-yloxy]-2,3-dihydro-benzofuran-3-yl}-acetic acid

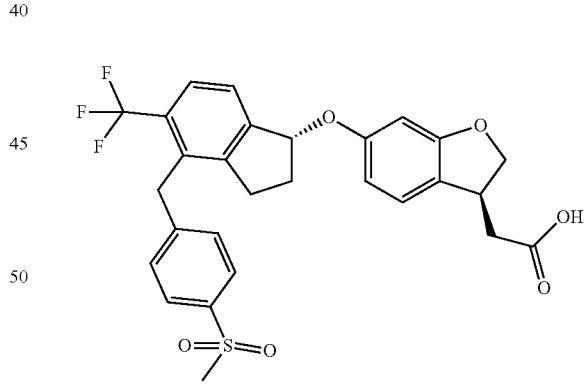

The title compound is prepared from {(S)-6-[(R)-4-(4-methylsulfonyl-benzyl)-5-trifluoromethyl-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 3): $t_R$=0.33 min; Mass spectrum (ESI$^-$): m/z=545 [M−H]$^-$.

Example 18

{(S)-6-[(R)-4-(3,5-Difluoro-benzyl)-7-fluoro-indan-1-yloxy]-2,3-dihydrobenzofuran-3-yl}-acetic acid

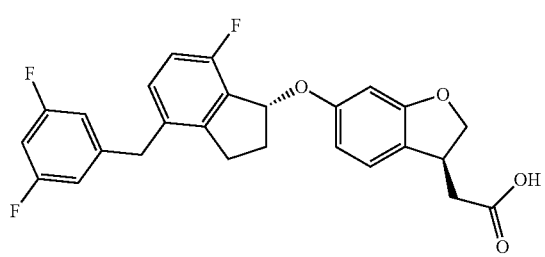 [SMILES: O=C(O)C[C@@H]1COc2cc(O[C@@H]3CCc4c(Cc5cc(F)cc(F)c5)ccc(F)c43)ccc21]

The title compound is prepared from {(S)-6-[(R)-4-(3,5-difluoro-benzyl)-7-fluoro-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 9): $t_R$=0.70 min; Mass spectrum (ESI−): m/z=453 [M−H]−.

Example 19

{(S)-6-[(R)-4-(2,6-Difluoro-benzyl)-7-fluoro-indan-1-yloxy]-2,3-dihydrobenzofuran-3-yl}-acetic acid

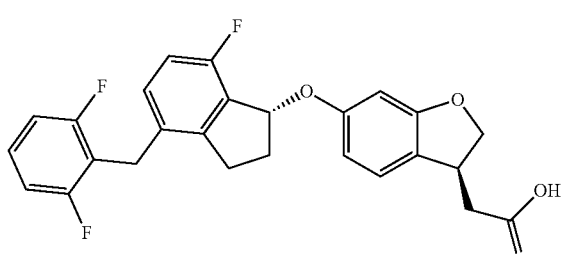

The title compound is prepared from {(S)-6-[(R)-4-(2,6-difluoro-benzyl)-7-fluoro-indan-1-yloxy]-2,3-dihydro-benzofuran-3-yl}-acetic acid methyl ester following a procedure analogous to that described for Example 1. LC (method 9): $t_R$=0.70 min; Mass spectrum (ESI−): m/z=453 [M−H]−.

Example 20

{(S)-6-[(R)-4-(4-Cyano-benzyl)-7-fluoro-indan-1-yloxy]-2,3-dihydrobenzofuran-3-yl}-acetic acid

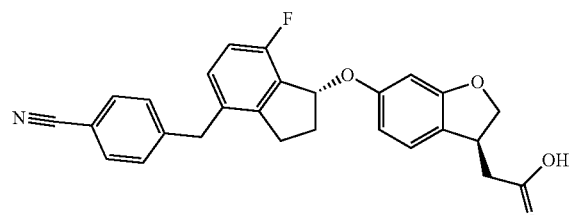

The title compound is prepared from {(S)-6-[(R)-4-(4-cyano-benzyl)-7-fluoro-indan-1-yloxy]-2,3-dihydro-benzofuran-3-yl}-acetic acid methyl ester following a procedure analogous to that described for Example 1. LC (method 9): $t_R$=0.46 min; Mass spectrum (ESI−): m/z=442 [M−H]−.

Example 21

{(S)-6-[(R)-4-(2,4-Difluoro-benzyl)-7-fluoro-indan-1-yloxy]-2,3-dihydrobenzofuran-3-yl}-acetic acid

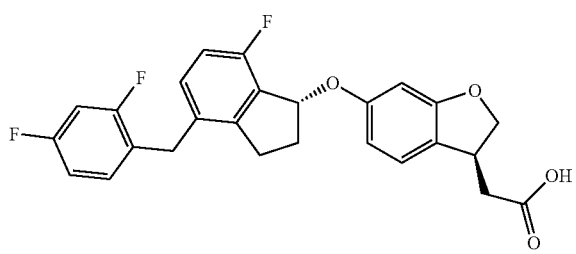 [SMILES: O=C(O)C[C@@H]1COc2cc(O[C@@H]3CCc4c(Cc5ccc(F)cc5F)ccc(F)c43)ccc21]

The title compound is prepared from {(S)-6-[(R)-4-(2,4-difluoro-benzyl)-7-fluoro-indan-1-yloxy]-2,3-dihydro-benzofuran-3-yl}-acetic acid methyl ester following a procedure analogous to that described for Example 1. LC (method 9): $t_R$=0.70 min; Mass spectrum (ESI−): m/z=453 [M−H]−.

Example 22

{(S)-6-[(R)-5-Cyano-4-(2-fluoro-benzyl)-indan-1-yloxy]-2,3-dihydro-benzofuran-3-yl}-acetic acid

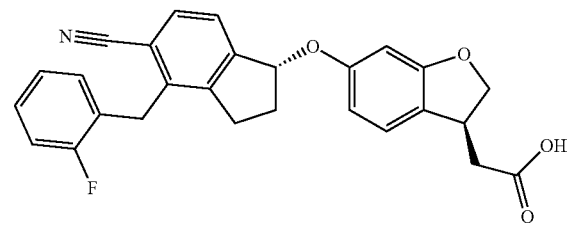 [SMILES: N#Cc1ccc2c(c1Cc1ccccc1F)CC[C@H]2Oc1ccc2c(c1)OC[C@H]2CC(=O)O]

The title compound is prepared from {(S)-6-[(R)-5-cyano-4-(2-fluoro-benzyl)-indan-1-yloxy]-2,3-dihydro-benzofuran-3-yl}-acetic acid methyl ester following a procedure analogous to that described for Example 1; the crude product is purified by HPLC (acetonitrile/water/trifluoroacetic acid). LC (method 2): $t_R$=1.13 min; Mass spectrum (ESI⁻): m/z=442 [M−H]⁻.

Example 23

{(S)-6-[(R)-5-Cyano-4-(4-fluoro-benzyl)-indan-1-yloxy]-2,3-dihydro-benzofuran-3-yl}-acetic acid

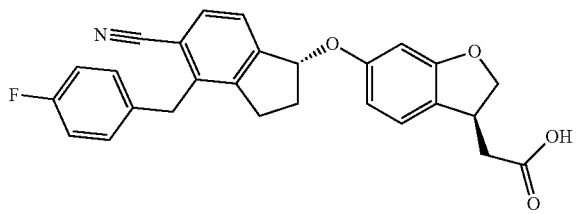 [SMILES: N#Cc1ccc2c(c1Cc1ccc(F)cc1)CC[C@H]2Oc1ccc2c(c1)OC[C@H]2CC(=O)O]

The title compound is prepared from {(S)-6-[(R)-5-cyano-4-(4-fluoro-benzyl)-indan-1-yloxy]-2,3-dihydro-benzofuran-3-yl}-acetic acid methyl ester following a procedure analogous to that described for Example 1; the crude product is purified by HPLC (acetonitrile/water/trifluoroacetic acid). LC (method 6): $t_R$=0.80 min; Mass spectrum (ESI⁻): m/z=442 [M−H]⁻.

Example 24

{(S)-6-[(R)-5-Cyano-4-(3-fluoro-benzyl)-indan-1-yloxy]-2,3-dihydro-benzofuran-3-yl}-acetic acid

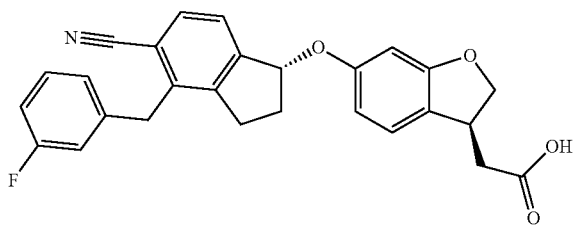 [SMILES: N#Cc1ccc2c(c1Cc1cccc(F)c1)CC[C@H]2Oc1ccc2c(c1)OC[C@H]2CC(=O)O]

The title compound is prepared from {(S)-6-[(R)-5-cyano-4-(3-fluoro-benzyl)-indan-1-yloxy]-2,3-dihydro-benzofuran-3-yl}-acetic acid methyl ester following a procedure analogous to that described for Example 1; the crude product is purified by HPLC (acetonitrile/water/trifluoroacetic acid). LC (method 8): $t_R$=1.16 min; Mass spectrum (ESI⁻): m/z=442 [M−H]⁻.

Example 25

{(S)-6-[(R)-4-(4-Hydroxy-benzyl)-5-trifluoromethyl-indan-1-yloxy]-2,3-dihydrobenzofuran-3-yl}-acetic acid

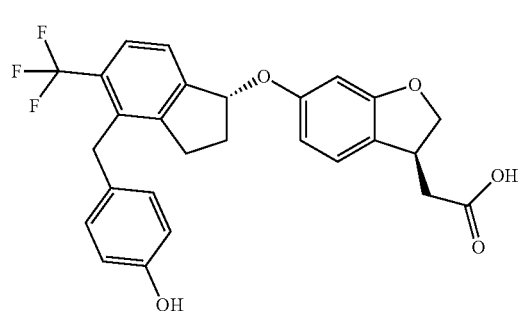 [SMILES: O=C(O)C[C@@H]1COc2cc(O[C@@H]3CCc4c3ccc(C(F)(F)F)c4Cc3ccc(O)cc3)ccc21]

The title compound is prepared from {(S)-6-[(R)-4-(4-hydroxy-benzyl)-7-fluoro-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 8): $t_R$=1.14 min; Mass spectrum (ESI⁻): m/z=483 [M−H]⁻.

Example 26

{(S)-6-[(R)-4-(2,4-Difluoro-benzyl)-5-trifluoromethyl-indan-1-yloxy]-2,3-dihydrobenzofuran-3-yl}-acetic acid

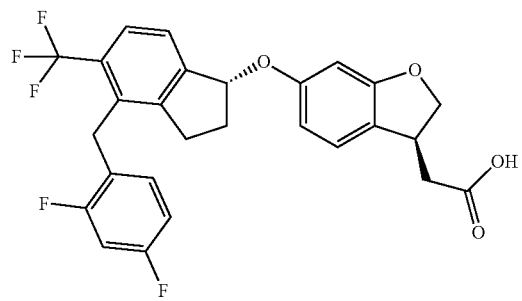 [SMILES: O=C(O)C[C@@H]1COc2cc(O[C@@H]3CCc4c3ccc(C(F)(F)F)c4Cc3ccc(F)cc3F)ccc21]

The title compound is prepared from {(S)-6-[(R)-4-(2,4-difluoro-benzyl)-5-trifluoromethyl-indan-1-yloxy]-2,3-dihydro-benzofuran-3-yl}-acetic acid methyl ester following a procedure analogous to that described for Example 1; the crude product is purified by HPLC (acetonitrile/water/trifluoroacetic acid). LC (method 3): $t_R$=0.81 min; Mass spectrum (ESI⁻): m/z=503 [M−H]⁻.

Example 27

{(S)-6-[(R)-4-(3-Methoxy-benzyl)-5-trifluoromethyl-indan-1-yloxy]-2,3-dihydrobenzofuran-3-yl}-acetic acid

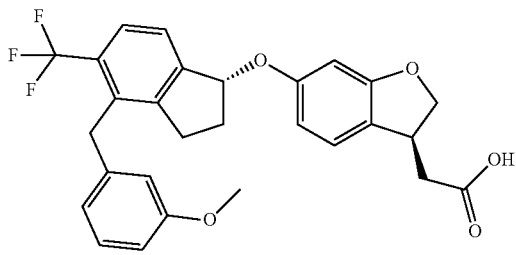 [SMILES: COc1cccc(Cc2c(C(F)(F)F)ccc3c2CC[C@H]3Oc2ccc3c(c2)OC[C@H]3CC(=O)O)c1]

The title compound is prepared from {(S)-6-[(R)-4-(3-methoxy-benzyl)-5-trifluoromethyl-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 8): $t_R$=1.24 min; Mass spectrum (ESI⁻): m/z=497 [M−H]⁻.

Example 28

{(S)-6-[(R)-5-Cyano-4-(2,6-difluoro-benzyl)-indan-1-yloxy]-2,3-dihydro-benzofuran-3-yl}-acetic acid

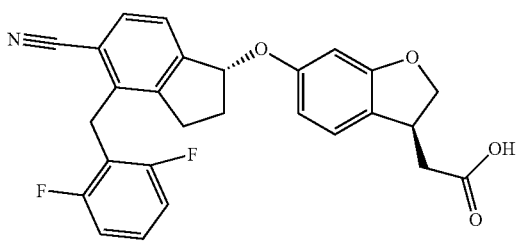 [SMILES: N#Cc1ccc2c(c1Cc1c(F)cccc1F)CC[C@H]2Oc1ccc2c(c1)OC[C@H]2CC(=O)O]

The title compound is prepared from {(S)-6-[(R)-5-cyano-4-(2,6-difluoro-benzyl)-indan-1-yloxy]-2,3-dihydro-benzofuran-3-yl}-acetic acid methyl ester following a procedure analogous to that described for Example 1. LC (method 4): $t_R$=1.15 min; Mass spectrum (ESI⁻): m/z=460 [M−H]⁻.

Example 29

{(S)-6-[(R)-4-(3-Fluoro-benzyl)-5-trifluoromethyl-indan-1-yloxy]-2,3-dihydrobenzofuran-3-yl}-acetic acid

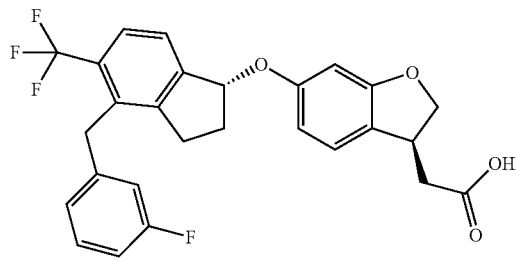 [SMILES: O=C(O)C[C@@H]1COc2cc(O[C@@H]3CCc4c3ccc(C(F)(F)F)c4Cc3cccc(F)c3)ccc21]

The title compound is prepared from {(S)-6-[(R)-4-(3-fluoro-benzyl)-5-trifluoromethyl-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 8): $t_R$=1.26 min; Mass spectrum (ESI⁻): m/z=485 [M−H]⁻.

Example 30

{(S)-6-[(R)-4-(4-Fluoro-benzyl)-5-trifluoromethyl-indan-1-yloxy]-2,3-dihydrobenzofuran-3-yl}-acetic acid

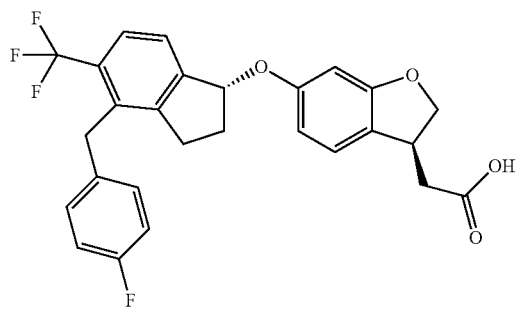 [SMILES: O=C(O)C[C@@H]1COc2cc(O[C@@H]3CCc4c3ccc(C(F)(F)F)c4Cc3ccc(F)cc3)ccc21]

The title compound is prepared from {(S)-6-[(R)-4-(4-fluoro-benzyl)-5-trifluoromethyl-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the

Example 31

{(S)-6-[(R)-4-(2-Fluoro-benzyl)-5-trifluoromethyl-indan-1-yloxy]-2,3-dihydrobenzofuran-3-yl}-acetic acid

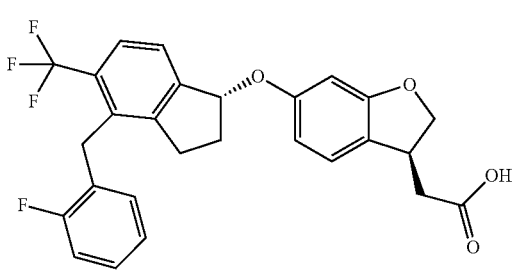 [SMILES: O=C(O)C[C@@H]1COc2cc(O[C@@H]3CCc4c3ccc(C(F)(F)F)c4Cc3ccccc3F)ccc21]

The title compound is prepared from {(S)-6-[(R)-4-(2-fluoro-benzyl)-5-trifluoromethyl-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 6): $t_R$=0.89 min; Mass spectrum (ESI$^-$): m/z=485 [M–H]$^-$.

Example 32

{(S)-6-[(R)-5-Cyano-4-(2,3-difluoro-benzyl)-indan-1-yloxy]-2,3-dihydro-benzofuran-3-yl}-acetic acid

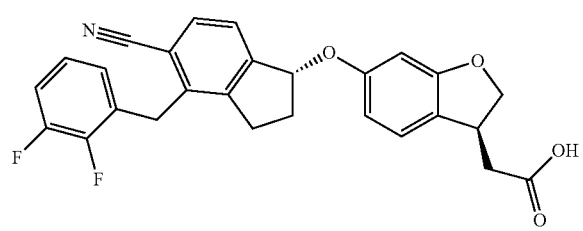 [SMILES: N#Cc1ccc2c(c1Cc1cccc(F)c1F)CC[C@H]2Oc1ccc2c(c1)OC[C@H]2CC(=O)O]

The title compound is prepared from {(S)-6-[(R)-5-cyano-4-(2,3-difluoro-benzyl)-indan-1-yloxy]-2,3-dihydro-benzofuran-3-yl}-acetic acid methyl ester following a procedure analogous to that described for Example 1; the crude product is purified by HPLC (acetonitrile/water/trifluoroacetic acid). LC (method 4): $t_R$=1.16 min; Mass spectrum (ESI$^-$): m/z=460 [M–H]$^-$.

Example 33

{(S)-6-[(R)-4-(4-Methoxy-benzyl)-5-trifluoromethyl-indan-1-yloxy]-2,3-dihydrobenzofuran-3-yl}-acetic acid

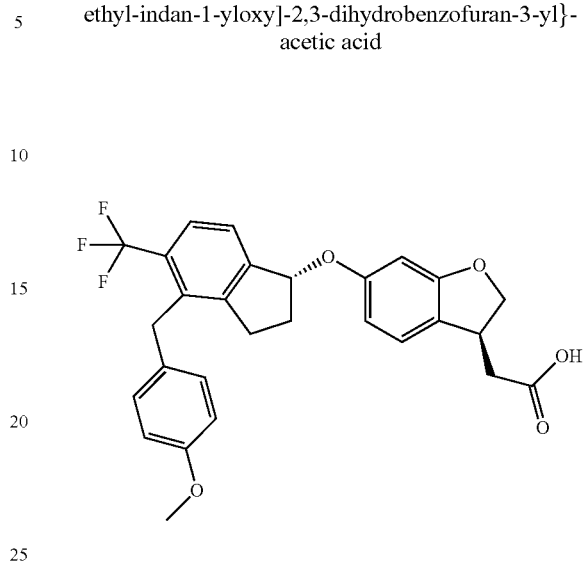

The title compound is prepared from {(S)-6-[(R)-4-(4-methoxy-benzyl)-5-trifluoromethyl-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 6): $t_R$=0.89 min; Mass spectrum (ESI$^-$): m/z=497 [M–H]$^-$.

Example 34

{(S)-6-[(R)-4-(3-Cyano-benzyl)-5-trifluoromethyl-indan-1-yloxy]-2,3-dihydrobenzofuran-3-yl}-acetic acid

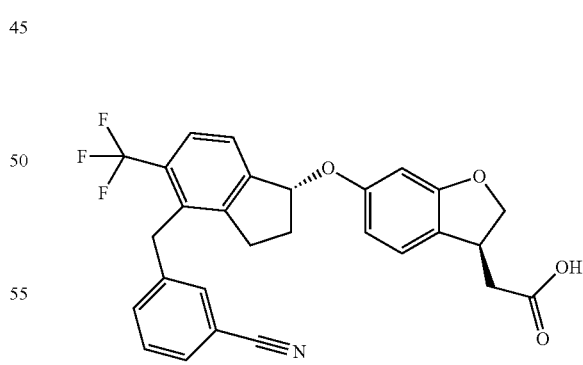

The title compound is prepared from {(S)-6-[(R)-4-(3-cyano-benzyl)-5-trifluoromethyl-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the

Example 35

{(S)-6-[(R)-4-(2-Methyl-benzyl)-5-trifluoromethyl-indan-1-yloxy]-2,3-dihydrobenzofuran-3-yl}-acetic acid

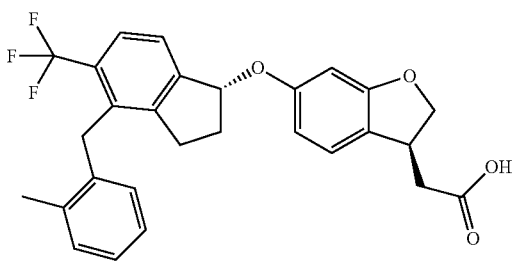 [SMILES: Cc1ccccc1Cc1c(C(F)(F)F)ccc2c1CC[C@H]2Oc1ccc2c(c1)OC[C@H]2CC(=O)O]

The title compound is prepared from {(S)-6-[(R)-4-(2-methyl-benzyl)-5-trifluoromethyl-indan-1-yloxy]-2,3-dihydrobenzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 6): $t_R$=0.91 min; Mass spectrum (ESI$^-$): m/z=481 [M−H]$^-$.

Example 36

{(S)-6-[(R)-4-(2-Cyano-benzyl)-5-trifluoromethyl-indan-1-yloxy]-2,3-dihydrobenzofuran-3-yl}-acetic acid

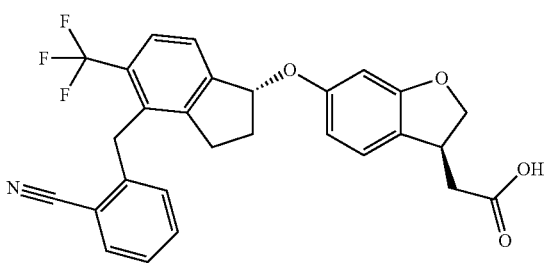 [SMILES: N#Cc1ccccc1Cc1c(C(F)(F)F)ccc2c1CC[C@H]2Oc1ccc2c(c1)OC[C@H]2CC(=O)O]

The title compound is prepared from {(S)-6-[(R)-4-(2-cyano-benzyl)-5-trifluoromethyl-indan-1-yloxy]-2,3-dihydrobenzofuran-3-yl}-acetic acid methyl ester following a procedure analogous to that described for Example 1; the crude product is purified by HPLC (acetonitrile/water/ammonia). LC (method 6): $t_R$=0.84 min; Mass spectrum (ESI$^+$): m/z=494 [M+H]$^+$.

Example 37

{(S)-6-[(R)-4-(4-Chloro-benzyl)-5-trifluoromethyl-indan-1-yloxy]-2,3-dihydrobenzofuran-3-yl}-acetic acid

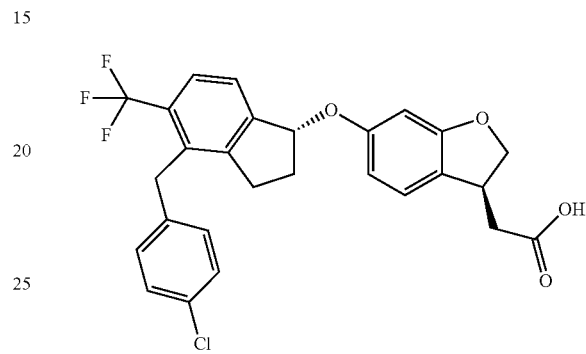

The title compound is prepared from {(S)-6-[(R)-4-(4-chloro-benzyl)-5-trifluoromethyl-indan-1-yloxy]-2,3-dihydro-benzofuran-3-yl}-acetic acid methyl ester following a procedure analogous to that described for Example 1; the crude product is purified by HPLC (acetonitrile/water/trifluoroacetic acid). LC (method 3): $t_R$=0.89 min; Mass spectrum (ESI$^-$): m/z=501/503 (Cl) [M−H]$^-$.

Example 38

{(S)-6-[(R)-4-(2-Methoxy-pyridin-5-yl)-5-trifluoromethyl-indan-1-yloxy]-2,3-dihydrobenzofuran-3-yl}-acetic acid

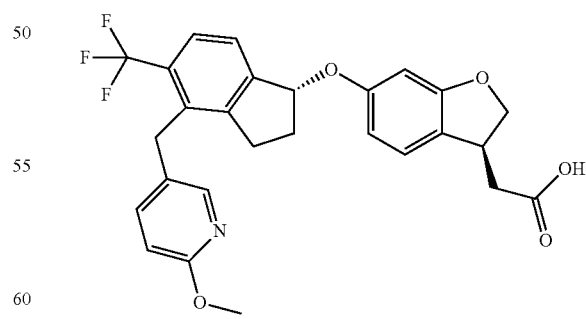

The title compound is prepared from {(S)-6-[(R)-4-(2-methoxy-pyridin-5-yl)-5-trifluoromethyl-indan-1-yloxy]-2,3-dihydro-benzofuran-3-yl}-acetic acid methyl ester following a procedure analogous to that described for Example 1; the crude product is purified by HPLC (acetonitrile/water/ trifluoroacetic acid). LC (method 2): $t_R$=1.13 min; Mass spectrum (ESI$^+$): m/z=500 [M+H]$^+$.

Example 39

{(S)-6-[(R)-4-(2-Fluoro-pyridin-5-yl)-5-trifluoromethyl-indan-1-yloxy]-2,3-dihydrobenzofuran-3-yl}-acetic acid

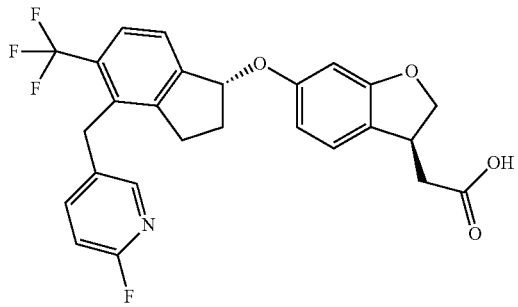 [SMILES: O=C(O)C[C@@H]1COc2cc(O[C@@H]3CCc4c3ccc(C(F)(F)F)c4Cc3ccc(F)nc3)ccc21]

The title compound is prepared from {(S)-6-[(R)-4-(2-fluoro-pyridin-5-yl)-5-trifluoromethyl-indan-1-yloxy]-2,3-dihydro-benzofuran-3-yl}-acetic acid methyl ester following a procedure analogous to that described for Example 1; the crude product is purified by HPLC (acetonitrile/water/trifluoroacetic acid). LC (method 2): $t_R$=1.14 min; Mass spectrum (ESI$^+$): m/z=488 [M+H]$^+$.

Example 40

{(S)-6-[(R)-4-(2,5-Dimethoxy-benzyl)-5-trifluoromethyl-indan-1-yloxy]-2,3-dihydrobenzofuran-3-yl}-acetic acid

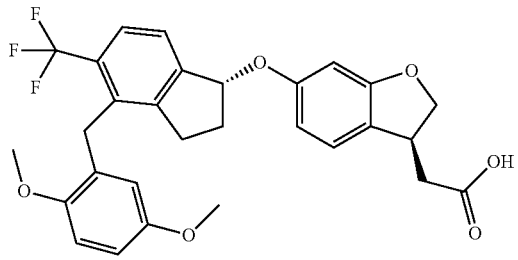 [SMILES: COc1ccc(OC)c(Cc2c(C(F)(F)F)ccc3c2CC[C@H]3Oc2ccc3c(c2)OC[C@H]3CC(=O)O)c1]

The title compound is prepared from {(S)-6-[(R)-4-(2,5-dimethoxy-benzyl)-5-trifluoromethyl-indan-1-yloxy]-2,3-dihydro-benzofuran-3-yl}-acetic acid methyl ester following a procedure analogous to that described for Example 1; after saponification of the ester the organic solvents are evaporated, water is added to the residue, and the resulting mixture is neutralized with 1N aqueous HCl solution. Upon stirring the aqueous solution, the title compound precipitates from the solution, the precipitate is collected and dried. LC (method 3): $t_R$=0.75 min; Mass spectrum (ESI$^+$): m/z=529 [M+H]$^+$.

The invention claimed is:

1. A compound of formula (I)

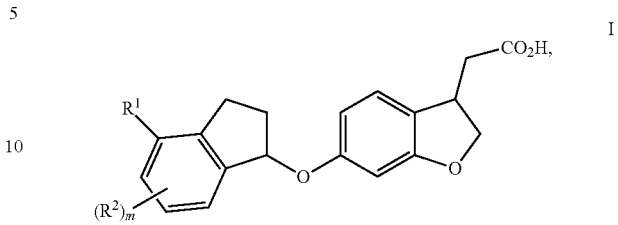

wherein:

$R^1$ is phenyl-CH$_2$— or heteroaryl-CH$_2$—, wherein the phenyl ring and the heteroaryl ring thereof are optionally independently substituted with 1 to 5 $R^3$ groups, and both —CH$_2$— moieties are optionally substituted with 1 or 2 H$_3$C— groups, wherein heteroaryl is a 5-membered heteroaromatic ring which contains 1 —NH— group, 1 —O—, or 1 —S— atom, or a 5-membered heteroaromatic ring which contains 1 —NH— group, 1 —O— or —S— atom and additionally 1 or 2 =N— atoms, or a 6-membered heteroaromatic ring which contains 1, 2, or 3 =N— atoms;

$R^2$ is F, Cl, Br, NC—, F$_2$HC—, F$_3$C—, F$_2$HC—O—, or F$_3$C—O—;

$R^3$ is F, Cl, Br, I, NC—, O$_2$N—, H$_2$N—, C$_{1-4}$-alkyl-NH—, (C$_{1-4}$-alkyl)$_2$N—, C$_{1-4}$-alkyl, C$_{2-4}$-alkenyl, C$_{2-4}$-alkinyl, HO—, HO—C$_{1-4}$-alkyl, C$_{1-4}$-alkyl-O—, C$_{1-4}$-alkyl-O—C$_{1-4}$-alkyl, C$_{1-4}$-alkyl-S—, C$_{1-4}$-alkyl-S(=O)—, C$_{1-4}$-alkyl-S(=O)$_2$—, —C$_{3-6}$ cycloalkyl-, or C$_{3-6}$-cycloalkyl-O—, wherein any alkyl and cycloalkyl group or submoiety is optionally substituted with 1 to 5 fluorine atoms; and m is 1 or 2;

wherein any alkyl group or sub-group is straight-chained or branched unless otherwise specified, or a salt thereof.

2. The compound according to claim 1, wherein:

$R^1$ is phenyl-CH$_2$— or heteroaryl-CH$_2$, wherein the phenyl ring is optionally independently substituted with 1 to 5 $R^3$ groups, the heteroaryl ring is optionally independently substituted with 1 to 3 groups $R^3$ groups, and both —CH$_2$— moieties are optionally substituted with 1 or 2 H$_3$C— groups, and wherein heteroaryl is a 5-membered heteroaromatic ring which contains 1 —NH— group, 1 —O— or —S— atom and additionally 1 or 2 =N— atoms, or a 6-membered heteroaromatic ring which contains 1 or 2 =N— atoms, or a salt thereof.

3. The compound according to claim 1, wherein $R^2$ is F, Cl, F$_3$C—, NC—, or F$_3$C—O—, or a salt thereof.

4. The compound according to claim 1, wherein $R^3$ is F, Cl, Br, NC—, C$_{1-4}$-alkyl-NH—, (C$_{1-4}$-alkyl)$_2$N—, C$_{1-4}$-alkyl, F$_2$HC—, F$_3$C—, HO—, HO—C$_{1-4}$-alkyl, C$_{1-4}$ alkyl-O—, F$_2$HC—O—, F$_3$C—O—, C$_{1-4}$-alkyl-O—C$_{1-4}$-alkyl, C$_{1-4}$-alkyl-S—, C$_{1-4}$-alkyl-S(=O)—, C$_{1-4}$-alkyl-S(=O)$_2$—, C$_{3-6}$-cycloalkyl-, or C$_{3-6}$-cycloalkyl-O—, or a salt thereof.

5. The compound according to claim 1, wherein:
$R^1$ is

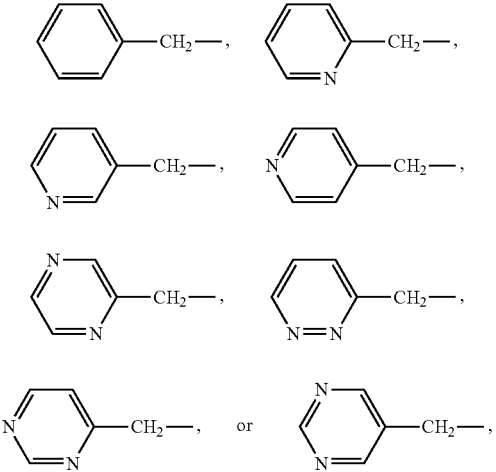

wherein the phenyl group and each heteroaromatic group is optionally independently substituted with 1 to 3 $R^3$ groups, and each —$CH_2$— moiety is optionally substituted with 1 or 2 $H_3C$— groups;

$R^2$ is F, Cl, $F_3C$—, NC—, or $F_3C$—O—;

$R^3$ is F, Cl, NC—, $C_{1-4}$-alkyl, $F_2HC$—, $F_3C$—, HO—, HO—$C_{1-4}$-alkyl, $C_{1-4}$-alkyl-O—, $F_2HC$—O—, $F_3C$—O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl-, or $C_{4-6}$-cycloalkyl-O—; and m is 1 or 2, or a salt thereof.

6. The compound according to claim 1, wherein:
$R^1$ is

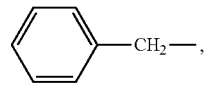

wherein the phenyl group is optionally independently substituted with 1 to 3 $R^3$ groups, and the —$CH_2$— moiety is optionally substituted with 1 or 2 $H_3C$— groups;

$R^2$ is F, $F_3C$—, or NC—;

$R^3$ is F, Cl, NC—, $C_{1-4}$-alkyl, $F_2HC$—, $F_3C$—, HO—, HO—$C_{1-4}$-alkyl, $C_{1-4}$-alkyl-O—, $F_2HC$—O—, $F_3C$—O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl-, or $C_{4-6}$-cycloalkyl-O—; and m is 1 or 2, or a salt thereof.

7. A pharmaceutically acceptable salt of the compound according to claim 1.

8. A pharmaceutical composition comprising the compound according to claim 1 or a pharmaceutically acceptable salt thereof, and an inert carrier or diluent.

9. A method for treating diabetes in a patient in need thereof, comprising administering a compound according to claim 1 or a pharmaceutically acceptable salt thereof to the patient.

10. A method for treating insulin resistance, obesity, cardiovascular disease, or dyslipidemia in a patient in need thereof, comprising administering a compound according to claim 1 or a pharmaceutically acceptable salt thereof to the patient.

11. The pharmaceutical composition according to claim 8, further comprising an additional therapeutic agent.

12. The pharmaceutical composition according to claim 11, wherein the additional therapeutic agent is an antidiabetic agent, agent for the treatment of overweight and/or obesity, or an agent for the treatment of high blood pressure, heart failure, and/or atherosclerosis.

* * * * *